US007638323B2

(12) United States Patent
Holgersson et al.

(10) Patent No.: US 7,638,323 B2
(45) Date of Patent: Dec. 29, 2009

(54) FUSION PROTEINS AND METHODS OF PRODUCING SAME

(75) Inventors: Jan Holgersson, Huddinge (SE); Jining Liu, Stockholm (SE); Anki Gustafsson, Stockholm (SE)

(73) Assignee: Recopharma AB, Stockholm (SE)

( * ) Notice: Subject to any disclaimer, the term of this patent is extended or adjusted under 35 U.S.C. 154(b) by 727 days.

(21) Appl. No.: 10/638,820

(22) Filed: Aug. 11, 2003

(65) Prior Publication Data
US 2004/0137580 A1 Jul. 15, 2004

Related U.S. Application Data

(60) Provisional application No. 60/402,211, filed on Aug. 9, 2002.

(51) Int. Cl.
*C12N 15/00* (2006.01)
*C12P 21/06* (2006.01)

(52) U.S. Cl. ............... 435/320.1; 435/69.7; 435/70.1; 435/71.1; 435/71.2; 435/328; 435/329; 435/358; 435/365

(58) Field of Classification Search .................. None
See application file for complete search history.

(56) References Cited

U.S. PATENT DOCUMENTS

| | | | |
|---|---|---|---|
| 5,225,538 A | 7/1993 | Capon et al. |
| 5,428,130 A | 6/1995 | Capon et al. |
| 5,455,165 A | 10/1995 | Capon et al. |
| 5,514,582 A | 5/1996 | Capon et al. |
| 5,516,964 A | 5/1996 | Umansky et al. |
| 5,714,147 A | 2/1998 | Capon et al. |
| 6,136,310 A | 10/2000 | Hanna et al. |

OTHER PUBLICATIONS

GenBank Accession No. NP_033177 (Jul. 2008).
GenBank Accession No. AJ417818 (Jun. 2002).
GenBank Accession No. XM_140694 (Oct. 2002).
GenBank Accession No. XP_140694 (Oct. 2002).
GenBank Accession No. XM_006867 (Aug. 2002).
GenBank Accession No. XP_006867 (Aug. 2002).
GenBank Accession No. NP_663625 (Mar. 2008).
GenBank Accession No. NM_145650 (Mar. 2008).
GenBank Accession No. CAD10625 (Apr. 2005).
GenBank Accession No. BAB66024 (May 2007).
GenBank Accession No. CAA79610 (Nov. 1995).
GenBank Accession No. AAA73558 (Jul. 1995).
GenBank Accession No. BAB30163 (Oct. 2006).
GenBank Accession No. P50127 (Jun. 2008).
GenBank Accession No. NM_009151 (Jul. 2008).
GenBank Accession No. Z19550 (Nov. 1995).
GenBank Accession No. AK016248 (Oct. 2006).
GenBank Accession No. L36152 (Jul. 1995).
Dorling et al., "Prospects for xenografting", *Curr. Opin. Immunol.*, 6(5):765-769 (1994).

Ye et al., "The pig as a potential organ donor for man. A study of potentially transferable disease from donor pig to recipient man.", *Transplantation*, 57(5):694-703 (1994).
Michaels et al., "Xenotransplant-associated zoonoses. Strategies for prevention", *Transplantation*, 57(1):1-7 (1994).
Calne, R.Y., "Organ transplantation between widely disparate species.", *Transplant. Proc.*, 2(4):550-556 (1970).
Bach et al., "Endothelial cell activation and thromboregulation during xenogrdt rejection", *Immunol. Rev.*, 141:5-30 (1994).
Magee, et al., "Xenograft rejection - molecular mechanisms and therapeutic implications", *Therap. Immunol.*, 1(1):45-58 (1994).
Platt et al., "Endothelial cell antigens recognized by xenoreactive human natural antibodies", *Transplantation*, 50(5):817-822 (1990).
Good et al., "Identification of carbohydrate structures that bind human antiporcine antibodies: implications for discordant xenografting in humans", *Transplant. Proc.*, 24(2):559-562 (1992).
Holgersson et al., "Carbohydrate specificity of human immunoglobulinM antibodies with pig lymphocytotoxic activity", *Transplant. Proc.*, 24(2):605-608 (1992).
Oriol et al., "Carbohydrate antigens of pig tissues reacting with human natural antibodies as potential targets for hyperacute vascular rejection in pig-to-man organ xenotransplantation", *Transplantation*, 56(6):1433-1442 (1993).
Galili, U., "Interaction of the natural anti-Gal antibody with alpha-galactosyl epitopes: a major obstacle for xenotransplantation in humans", *Immunol. Today*, 14 (10):480-482 (1993).
Sandrin et al., "Anti-pig IgM antibodies in human serum react predominantly with Gal($\alpha$1-3)Gal epitopes", *Proc. Natl. Acad Sci. USA*, 90(23):11391-11395 (1993).
Cairns et al., "Xenografts - future prospects for clinical transplantation", *Immunol. Lett.*, 29(1-2):167-170 (1991).
Rydberg et al., "Studies on the removal of anti-pig xenoantibodies in the human by plasmapheresis/immunoadsorption",*Xenotransp/antation*, 2:253-263 (1995).
Soares et al., "In vivo depletion of xenoreactive natural antibodies with an anti-µ monoclonal antibody", *Transplantation*, 56(6):1427-1433 (1993).
Soares et al., "In vivo IgM depletion by anti-µ monoclonal antibody therapy. The role of IgM in hyperacute vascular rejection of discordant xenografts", *Transplantation*, 57(7):1003-1009 (1994).
Leventhal et al., "Removal of baboon and human antiporcine IgG and IgM natural antibodies by immunoadsorption. Results of in vitro and in vivo studies", *Transplantation*, 59(2):294-300 (1995).
Geller et al., "Evidence that polyreactive antibodies are deposited in rejected discordant xenografts", *Transplantation*, 55(1):168-172 (1993).
Koren et al., "Murine monoclonal anti-idiotypic antibodies directed against human anti-αGal antibodies prevent rejection of pig cells in culture: implications for pig-to-human organ xenotransplantation", *Transplant. Proc.*, 28(2):559 (1996).

(Continued)

*Primary Examiner*—Eileen B O'Hara
*Assistant Examiner*—F. Pierre VanderVegt
(74) *Attorney, Agent, or Firm*—Cynthia A. Kozakiewicz; Ivor R. Elrifi; Mintz, Levin, Cohn, Ferris, Glovsky and Popeo, P.C.

(57) ABSTRACT

The present invention provides compositions and methods for treating or preventing hyperacute rejection.

13 Claims, 14 Drawing Sheets

OTHER PUBLICATIONS

Leventhal et al., "The synergistic effect of combined antibody and complement depletion on discordant cardiac xenograft survival in nonhuman primates", *Transplantation*, 57(6):974-978 (1994).

Pruitt et al. "The effect of soluble complement receptor type 1 on hyperacute rejection of porcine xenografts", *Transplantation*, 57(3):363-370 (1994).

Neethling et al., "Immunoadsorption of natural antibodies from human serum by affinity chromatography using specific carbohydrates protects pig cells from cytotoxic destruction", *Transplant. Proc.*, 26(3):1378 (1994).

Neethling et al., "Protection of pig kidney (PK15) cells from the cytotoxic effect of anti-pig antibodies by α-galactosyl oligosaccharides", *Transplantation*, 57(6):959-963 (1994).

Li et al., "Inhibition of human anti-αGal IgQ by oligosaccharides derived from porcine stomach mucin", *Xenotransplantation*, 2:279-288 (1995).

Cooper et al., "Specific intravenous carbohydrate therapy: a new approach to the inhibition of antibody-mediated rejection following ABO-incompatible allografting and discordant xenografting", *Transplant. Proc.*, 25(1):377-378 (1993).

Sandrin et al., "Enzymatic remodelling of the carbohydrate surface of a xenogenic cell substantially reduces human antibody binding and complement-mediated cytolysis",*Nat. Med.*, 1(12):1261-1267 (1995).

Sharma et al., "Reduction in the level of Gal(α1,3)Gal in transgenic mice and pigs by the expression of an α(1,2)fucosyltransferase", *Proc. Natl. Acad Sci. USA*, 93(14):7190-7195 (1996).

Koike et al., "Introduction of α(1,2)-fucosyltransferase and its effect on αGal epitopes in transgenic pig", *Xenotransplantation*, 3:81-86 (1996).

Blakely et al., "Activation of intragraft endothelial and mononuclear cells during discordant xenograft rejection", *Transplantation*, 58(10):1059-1066 (1994).

Seebach et al., "Xenogeneic human anti-pig cytotoxicity mediated by activated natural killer cells", *Xenotransplantation*, 3:188-197 (1996).

Chou et al., "Identication of α-galactose (α-fucose)-asialo-$G_{M1}$ glycolipid expressed by subsets of rat dorsal root ganglion neurons", *J. Biol. Chem.*, 264(6):3409-3415 (1989).

Fujiwara et al., "Structure and distribution of N-linked oligosaccharide chains on various domains of mouse tumour laminin", *Biochem. J.*, 252(2):453-461 (1988).

Dasgupta et al., "Branched monosialo gangliosides of the lacto-series isolated from bovine erythrocytes: characterization of a novel ganglioside, NeuGc-isooctaosylceramide", *Arch. Biochem. Biophys.*, 310(2):373-384 (1994).

Wong, CH, "Enzymatic and Chemo-Enzymatic Synthesis of Carbohydrates", *Pure Appl. Chem.*, 67(10):1609-1616 (1995).

Seed, B., "An LFA-3 cDNA encodes a phospholipid-linked membrane protein homobgous to its receptor CD2", *Nature*, 329(6142):840-842 (1987).

Khodadoust et al., "PEC-A: An immortalized porcine aortic endothelial cell",*Xenotransplantation*, 2:79-87 (1995).

Dabkowski et al., "Characterisation of a cDNA clone encoding the pig α1,3 galactosyltransferase: implications for xenotransplantation", *Transplant. Proc.*, 25(5):2921 (1993).

Dabkowski et al., "Isolation of a cDNA clone encoding the pig α 1,3 galactosyltransferase", *Transplant. Proc.*, 26(3):1335 (1994).

Gustafsson et al., "α 1,3galactosyltransferase: a target for in vivo genetic manipulation in xenotransplantation", *Immunol. Rev.*, 141:59-70 (1994).

Sako et al., "Expression cloning of a functional glycoprotein ligand for P-selectin", *Cell*, 75(6):1179-1186 (1993).

Laemmli, U.K., "Cleavage of structural proteins during the assembly of the head of bacteriophage T4", *Nature*, 227:680-685 (1970).

Towbin et al., "Electrophoretic transfer of proteins from polyacrylamide gels to nitrocellulose sheets: procedure and some applications", *Proc. Natl. Acad. Sci. USA*, 76(9):4350-4354 (1979).

Carraway et al., "Cell surface mucin-type glycoproteins and mucin like domains", *Glycobiology*, 1(2):131-138 (1991).

Shimizu et al., "Mucins in the mainstream",*Nature*, 366:630-631 (1993).

Galili et al., "Human natural anti-α-galactosyl IgG. II. The specific recognition of α(1→3)-linked galactose residues", *J. Exp. Med.*, 162:573-582 (1985).

Platt et al., "Immunopathology of hyperacute xenograft rejection in a swineto-primate model", *Transplantation*, 52(2):214-220 (1991).

Cooper et al., "Specific intravenous carbohydrate therapy. A new concept in inhibiting antibody mediated rejection-experience with ABO-incompatible cardiac allografting in the baboon", *Transplantation*, 56(4):769-777 (1993).

Romano et al., "Preliminary human study of synthetic trisaccharide representing blood substance A", *Transplant. Proc.*, 19(6):4475-4478 (1987).

Ye et al., "Evidence that intravenously administered α-galactosyl carbohydrates reduce baboon serum cytotoxicity to pig kidney cells (PK15) and transplanted pig hearts", *Transplantation*, 58(3):330-337 (1994).

Vaughan et al., "Recognition of an octapeptide sequence by multiple Galα(1,3)Gal-biding proteins", *Xenotransplantation*, 3:18-23 (1996).

Kooyman et al., "Identification and characterization of a galactosyl peptide mimetic: Implications for use in removing xenoreactive anti-α Gal antibodies", *Transplantation*, 61(6):851-855 (1996).

Koren et al., "Monoclonal antiidiotypic antibodies neutralize cytotoxic effects of anti-αGal antibodies", *Transplantation*, 62(6):837-843 (1996).

Fodor et al., "Expression of a functional human complement inhbitor in a transgenic pig as a model for the prevention of xenogeneic hyperacute organ rejection",*Proc. Natl. Acad. Sci. USA*, 91(23):11153-11157 (1994).

Rosengard et al., "Tissue expression of human complement inhibitor, decay-accelarating factor, in transgenic pigs. A potential approach for preventing xenograft rejection", *Transplantation*, 59(9):1325-1333 (1995).

Diamond et al., "Characterization of transgenic pigs expressing functionally active human CD59 on cardiac endothelium", *Transplantation*, 61(8):1241-1249 (1996).

Kroshus et al., "Expression of human CD59 in transgenic pig organs enhances organ survival in an ex vivo xenogeneic perfusion model", *Transplantation*, 61(10):1513-1521 (1996).

Pascher et al., "Human decay accelerating factor expressed on endothelial cells of transgenic pigs affects complement activation in an ex vivo liver perfusion model",*Transplant. Proc.*, 28(2):754-755 (1996).

Schmoeckel et al., "Prevention of hyperacute rejection by human decay accelerating factor in xenogeneic perfused working hearts", *Transplantation*, 62(6):729-734 (1996).

Rosen et al., "Leukocyte adhesion: Two selectins converge on sulphate", *Curr. Biol.*, 6(3):261-264 (1996).

Asa et al., "The P-Selectin Glycoprotein Ligand Functions as a Common Human Leukocyte Ligand For P- and E-Selectins", *J. Biol. Chem.*, 270(19):11662-11670 (1995).

Schaapherder et al., "Human complement activation via the alternative pathway on porcine endothelium initiated by IgA antibodies", *Transplantation*, 60(3):287-291 (1995).

Gauldie et al., "Fc receptors for IgA and other immunoglobulins on resident and activated alveolar macrophages", *Mol. Immunol.*, 20(9):1029-1037 (1983).

Monteiro et al., "Cellular distribution, regulation, and biochemical nature of an Fcα receptor in humans", *J. Exp. Med.*, 171:597-613 (1990).

Auchincloss et al., "Xenogeneic transplantation",*Annu. Rev. Immunol.*, 16:433-470 (1998).

Bhatia et al., "Protein glycosylation: implications for in vivo functions and therapeutic applicatons", *Adv. Biochem, Eng. Biotechnol.*, 64:155-201 (1998).

Bierhuizen et al., "Expression cloning of a cDNA encoding UDP-GlcNAc:Galβ1-3-GalNAc-R (GlcNAc to GalNAc) β1-6GlcNAc transferase by gene transfer into CHO cells expressing polyoma large tumor antigen", *Proc. Natl. Acad. Sci. U.S.A.*, 89:9326-9330 (1992).

Bouhours et al., "Simultaneous expression by porcine aorta endothelial cells of glycosphingolipids bearing the major epitope for human xenoreactive antibodies (Galα1-3Gal), blood group H determinant and N-glycolylneuraminic acid", *Glycoconj. J.*, 13:947-953 (1996).

Boussif et al., "A versatile vector for gene and oligonucleotide transfer into cells in culture and in vivo: polyethylenimine",*Proc. Natl. Acad. Sci. U.S.A.*, 92:7297-7301 (1995).

Cairns et al., "Thomsen-Friedenreich and P$^K$ antigens in pig-to-human xenotransplantation", *Transplant. Proc.*, 28(2):795-796 (1996).

Carlstedt et al., "Characterization of two different glycosylated domains from the insoluble mucin complex of rat small intestine",*J. Biol. Chem.*, 268(25):18771-18781 (1993).

Ciucanu et al., "A simple and rapid method for the permethylation of carbohydrates",*Carbohydr. Res.*, 131:209-217 (1984).

Corzana et al., "Solution structure of two xenoantigens: αGal-LacNAc and αGal-Lewis X", *Glycobiology*, 12(4):241-250 (2002).

Dennis, J.W., "Core 2 GlcNAc-transferase and polylactosamine expression in O-glycans", *Glycobiology*, 3(2):91-96 (1993).

Gervais et al., "Glycosylation of human recombinant gonadotrophins: characterization and batch-to-batch consistency", *Glycobiology*, 13(3):179-189 (2003).

Hansson et al., "Gas chromatography and gas chromatography mass spectrometry of glycoprotein oligosaccharides", *Meth. Mol. Biol.*, Chapter 4, 14:47-54 (1993).

He et al., "The in vitro activity and specificity of human endothelial cell-specific promoters in porcine cells", *Xenotransplantation*, 8:202-212 (2001).

Hokke et al., "Structural analysis of the sialylated N- and O-linked carbohydrate chains of recombinant human erythropoietin expressed in Chinese hamster ovary cells. Sialylation patterns and branch location of dimeric N-acetyllactosamine units", *Eur. J. Biochem.*, 228:981-1008 (1995).

Imberty et al., "Computer simulation of histo-blood group oligosaccharides: energy maps of all constituting disaccharides and potential energy surfaces of 14 ABH and Lewis carbohydrate antigens", *Glycoconj. J.*, 12:331-349 (1995).

Imberty et al., "How do antibodies and lectins recognize histo-blood group antigens? A 3D-QSAR study by comparative molecular field analysis (CoMFA)",*Bioorg. Med. Chem.*, 4(11):1979-1988 (1996).

Imberty et al., "Flexibility in a tetrasaccharide fragment from the high mannose type of Nlinked oligosaccharides", *Int. J. Biol. Macromol.*, 15:17-23 (1993).

Itoh et al., "Structural analysis of a glycoprotein by liquid chromatography-mass spectrometry and liquid chromatography with tandem mass spectrometry. Application to recombinant human thrombomodulin", *J. Chromatogr. A.*, 978:141-152 (2002).

Joziasse et al., "Characterization of an α1→3-galactosyltransferase homologue on human chromosome 12 that is organized as a processed pseudogene",*J. Biol. Chem.*, 266(11):6991-6998 (1991).

Khodadoust et al., "PEC-A: an immortalized porcine aortic endothelial cell",*Xenotransplantation*, 2:79-87 (1995).

Kitov et al., "Shiga-like toxins are neutralized by tailored multivalent carbohydrate ligands",*Nature*, 403:669-672 (2000).

Kumar et al., "Core2 β-1,6-N-acetylglucosaminyltransferase enzyme activity is critical for P-selectin glycoprotein ligand-1 binding to P-selectin", *Blood*, 88(10):3872-3879 (1996).

Lee et al., "Affinity enhancement by multivalent lectiricarbohydrate interaction", *Glycoconj. J.*, 17:543-551 (2000).

Lindhorst et al., "Inhibition of the type 1 fimbriae-mediated adhesion of *Escherichia coli* to erythrocytes by multiantennary α-mannosyl clusters: the effect of multivalency",*Glycoconj. J.*, 15:605-613 (1998).

Liu et al., "Removal of xenoreactive human anti-pig antibodies by absorption on recombinant mucin-containing glycoproteins carrying the Galα1,3Gal epitope", *Transplantation*, 63(11):1673-1682 (1997).

Liu et al., "Multivalent Galα1,3Gal-substitution makes recombinant mucin-immunoglobulins efficient absorbers of anti-pig antibodies", *Xenotransplantation*, 10:149-163 (2003).

Löfling et al., "Absorption of anti-blood group A antibodies on P-selectin glycoprotein ligand-1/immunoglobulin chimeras carrying blood group A determinants: core saccharide chain specificity of the Se and H gene encoded α1,2 fucosyltransferases in different host cells", *Glycobiology*, 12(3):173-182 (2002).

Maaheimo et al., "Synthesis of a divalent sialyl Lewis x O-glycan, a potent inhibitor of lymphocyte-endothelium adhesion. Evidence that multivalency enhances the saccharide binding to L-selectin", *Eur. J. Biochem.*, 234:616-625 (1995).

Malykh et al., "Regulation of N-glycolylneuraminic acid biosynthesis in developing pig small intestine", *Biochem. J.*, 370:601-607 (2003).

Malykh et al., "Distribution and localization of CMP-N-acetylneuraminic acid hydroxylase and N-glycolylneuraminic acid-containing glycoconjugates in porcine lymph node and peripheral blood lymphocytes", *Eur. J. Cell. Biol.*, 80:48-58 (2001).

Mammen et al., "Polyvalent interactions in biological systems: implications for design and use of multivalent ligands and inhibitors",*Angew. Chem. Int. Ed.*, 37:2754-2794 (1998).

McEver et al., "Leukocyte trafficking mediated by selectin-carbohydrate interactions", *J. Biol. Chem.*, 270(19): 11025-11028 (1995).

Mitoma et al., "Extended core 1 and core 2 branched O-glycans differentially modulate sialyl Lewis X-type L-selectin ligand activity", *J. Biol. Chem.*, 278(11):9953-9961 (2003).

Miyata et al., "Xeno—still stuck without αGal", *Nat. Biotechnol.*, 21:359-360 (2003).

Moore et al., "The P-selectin glycoprotein ligand from human neutrophils displays sialylated, fucosylated, O-linked poly-N-acetyllactosamine", *J. Biol. Chem.*, 269(37):23318-23327 (1994).

Pascher et al., "Immunoapheresis, an advanced technique for depleting human anti-porcine antibodies, delays hyperacute rejection of xenogeneic perfused pig livers", *Transplant. Proc.*, 29:962-963 (1997).

Phelps et al., "Production of α1,3-galactosyltransferase-deficient pigs", *Science*, 299:411-414 (2003).

Renkonen et al., "Synthesis of a new nanomolar saccharide inhibitor of lymphocyte adhesion: different polylactosamine backbones present multiple sialyl Lewis x determinants to L-selectin in high-affinity mode", *Glycobiology*, 7(4):453-461 (1997).

Rydberg et al., "α-Gal epitopes in animal tissue glycoproteins and glycolipids",*Subcell. Biochem.*, Chapter 5, 32:107-125 (1999).

Sako et al., "Expression cloning of a functional glycoprotein ligand for P-selectin", *Cell*, 75:1179-1186 (1993).

Sako et al., "A sulfated peptide segment at the amino terminus of PSGL-1 is critical for P-selectin binding", *Cell*, 83:323-331 (1995).

Schachter, H., "The joys of HexNAc. The synthesis and function of N- and O-glycan branches", *Glycoconj. J.*, 17:465-483 (2000).

Sharma et al., "Pig cells that lack the gene for α1-3 galactosyltransferase express low levels of the gal antigen", *Transplantation*, 75(4):430-436 (2003).

Sheeley et al., "Characterization of monoclonal antibody glycosylation: comparison of expression systems and identification of terminal α-linked galactose", *Anal. Biochem.*, 247:102-110 (1997).

Silverman et al., "The contribution of tandem repeat number of the O-glycosylation of mucins", *Glycobiology*, 13(4):265-277 (2003).

Skrincoslcy et al., "Altered golgi localization of core 2β-1,6-N-acetylglucosaminyltransferase leads to decrease synthesis of branched O-glycans", *J. Biol. Chem.*, 272(36):22695-22702 (1997).

Ten Hagen et al., "All in the family: the UDP-GalNAc:polypeptide N-acetylgalactosaminyltransferases", *Glycobiology*, 13(1):1R-16R (2003).

Totani et al., "Chemoenzymatic synthesis and application of glycopolymers containing multivalent sialyloligosaccharides with a poly(L-glutamic acid) backbone for inhibition of infection by influenza viruses", *Glycobiology*, 13(5):315-326 (2003).

Van den Nieuwenhof et al., "Recombinant glycodelin carrying the same type of glycan structures as contraceptive glycodelin-A can be produced in human kidney 293 cells but not in Chinese hamster ovary cells", *Eur. J. Biochem.*, 267:4753-4762 (2000).

Varki, A., "N-glycolylneuraminic acid deficiency in humans",*Biochimie*, 83:615-622 (2001).

Yan et al., "Novel Asn-linked oligosaccharides terminating in GalNAcjS(1-*4)[Fuca(1-*3)]GlcNAc /3 (1<<) are present in recombinant human protein C expressed in human kidney 293 cells", *Glycobiology*, 3(6):597-608 (1993).

Yeh et al., "Molecular cloning and expression of a novel β-1, 6-N-acetylglucosaminyltransferase that forms core 2, core 4, and I branches", *J. Biol. Chem.*, 274(5):3215-3221 (1999).

Zhu et al., "Anti-N-glycolylneuraminic acid antibodies identified in healthy human serum", *Xenotransplantation*, 9:376-381 (2002).

FUSION PROTEINS AND METHODS OF PRODUCING SAME

RELATED APPLICATIONS

This application claims priority to U.S. Ser. No. 60/402,211, filed Aug. 9, 2002, the contents of which is incorporated herein by reference in its entirety.

FIELD OF THE INVENTION

The invention relates to generally to compositions and methods for treating or preventing hyperacute rejection and more particularly to compositions including fusion polypeptides comprising the carbohydrate epitope, Galα1,3Gal.

BACKGROUND OF THE INVENTION

The chronic lack of donor organs for allotransplantation may be solved if transplantation of organs or tissues from animal to man, i.e. xenotransplantation, could be performed. The pig is considered to be the most suitable donor species for human xenotransplantations, but several problems need to be solved before it can be used on a routine basis. The initial immunological barrier is caused by xenoreactive, natural antibodies (XNAb) in humans, apes and Old world monkeys, that are specific for a carbohydrate epitope, Galα1,3Gal (α-Gal), present in other mammals including pigs. The binding of XNAbs to α-Gal epitopes on pig endothelial cells, initiates a series of events, which leads to graft loss within minutes to hours (Galili, U., 1993; Oriol, R. et al., 1993).

SUMMARY OF THE INVENTION

The invention is based in part in the discovery that the carbohydrate epitope Galα1, 3Gal (αGal) can be specifically expressed at high density and by different core saccharides chains on mucin-type protein backbones. This higher density of αGal epitopes results in an increased binding or removal (i.e., absorption) of anti-αGal antibodies as compared to free saccharides, or αGal determinants linked to solid phase. The polypeptides, are referred to herein as αGal fusion polypeptides.

The invention features a fusion polypeptide which binds a Gal α1,3Gal specific antibody. The fusion polypeptide includes a mucin polypeptide and an immunoglobulin polypeptide. The mucin polypeptide has a glycan repertoire including the following sequence Hex-HexNol-HexN-Hex-Hex; NeuAc-Hex-HexNol-HexN-Hex-Hex and NeuGc-Hex-HexNol-HexN-Hex-Hex.

The invention also features a fusion polypeptide that includes a first polypeptide, having at least a region of a mucin polypeptide, glycosylated by an α1,3 galactosyltranserase and a β 1,6, N-acetylglucosaminyltransferase linked to a second polypeptide.

Also provided by the invention are methods of producing a fusion polypeptide. Fusion polypeptides are produced by providing a cell containing a nucleic acid encoding a mucin polypeptide operably linked to a nucleic acid encoding at least a portion of an immunoglobulin polypeptide; a nucleic acid encoding an α1,3 galactosyltransferase polypeptide; and a nucleic acid encoding a β 1,6,-N-acetylglucosaminyltransferase polypeptide. Alternatively, fusion polypeptides are produced by introducing to a cell (e.g., transfection or transformation) a nucleic acid encoding a mucin polypeptide operably linked to a nucleic acid encoding at least a portion of an immunoglobulin polypeptide; a nucleic acid encoding an α1,3 galactosyltransferase polypeptide; and a nucleic acid encoding a β 1,6,-N-acetylglucosaminyltransferase polypeptide. The cell is cultured under conditions that permit production of the fusion polypeptide and the fusion polypeptide is isolated from the culture. Fusion polypeptides are isolated by methods known in the art. For example, the fusion polypeptides are isolated using Protein A or Protein G chromatography.

The cell is a eukarotic cell, or a prokaryotic cell, e.g. a bacterial cell. A eukarotic cell is, for example, a mammalian cell, an insect cell or a yeast cell. Exemplary eukarotic cells include a CHO cell, a COS cell or a 293 cell.

The mucin polypeptide is for example PSGL-1. Preferably, the mucin polypeptide is the extracellular portion of PSGL-1. In preferred embodiments, the second polypeptide comprises at least a region of an immunoglobulin polypeptide. For example, the second polypeptide comprises a region of a heavy chain immunoglobulin polypeptide. Alternatively, the second polypeptide comprises the FC region of an immunoglobulin heavy chain.

The fusion polypeptide is a mutimer. Preferably, the fusion polypeptide is a dimer.

Also included in the invention is a nucleic acid encoding an αGal fusion polypeptide, as well as a vector containing an αGal fusion polypeptide-encoding nucleic acids described herein, and a cell containing the vectors or nucleic acids described herein. Alternatively the vector further comprises a nucleic acid encoding a an α1,3 galactosyltransferase and/or a core 2 β1,6-N-acetylglusosaminyltransferase. The invention also includes host cell, e.g. CHO cells genetically engineered to express the αGal fusion polypeptide.

In another aspect, the invention provides a method of treating antibody-mediated rejection in a subject, e.g., hyperacute rejection. The method includes contacting a biological sample, e.g., whole blood or plasma from a subject with the αGal fusion polypeptide of the invention to form an fusion polypeptide-antibody complex. The complex is removed from the biological sample and the biological sample is refused into the subject.

Also included in the invention is a method of removing an antibody from a sample by contacting the sample with the αGal fusion peptide of the invention to form an antibody-fusion peptide complex and removing the complex from the biological sample.

Also included in the invention are pharmaceutical compositions that include the αGal fusion polypeptides.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION OF THE INVENTION

The invention is based in part in the discovery that the carbohydrate epitope Galα1,3Gal (αGal) can be specifically expressed at high density and by different core saccharides chains on mucin-type protein backbones. More particularly, the invention is based upon the surprising discovery that expression of αGal epitopes of mucin-type protein backbones is dependent upon the cell line expressing the polypeptide. Moreover, the glycan repertoire of the mucin can be modified by co-expresion of exogenous α1,3 galactosyltransferase and a core 2 branching enzyme. This modification results in a higher density of αGal eptiopes and an increased binding or removal (i.e., absorption) of anti-αGal antibodies as compared to free saccharides, αGal determinants linked to solid phase, or cells transfected with α1,3 galactosyltransferase alone.

Transient transfection of a PSGL-1/mIgG$_{2b}$ fusion protein and porcine α1,3galactosyltransferase (α1,3GalT) in COS cells results in a dimeric fusion protein heavily substituted with α-Gal epitopes. The fusion protein has approximately terminal α-Gal epitopes per dimmer and a xenoreactive natural antibodies (XNAb) adsorption efficiency 20 times higher (on a carbohydrate molar basis) than pig thyroglobulin immobilized on agarose beads, and 5,000 and 30,000 times higher than Galα1,3Gal-conjugated agarose and macroporous glass beads, respectively.

Figure 2:
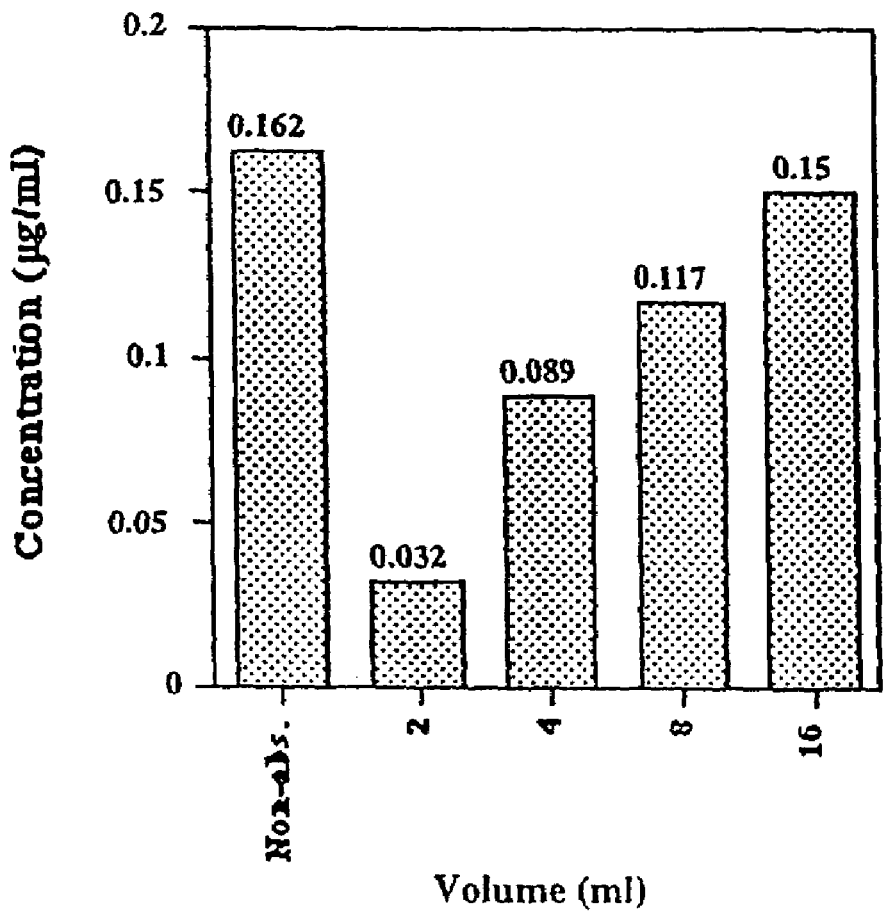
FIG. 2A is a bar chart showing quantification by anti-mouse IgG Fc ELISA of the PSGL1/mIgG$_{2b}$ fusion protein concentration in increasing volumes of transfected COS cell supernatants before and after absorption on 50 µl of anti-mouse IgG agarose beads. Triplicate samples were analyzed.
FIG. 2B is a photograph of a gel showing the PSGL1/mIgG$_{2b}$ fusion protein concentration in increasing volumes of transfected COS cell supernatants FIG. 3. is a line graph showing Antibody-dependent, complement-mediated PEC-A cell cytotoxicity by different volumes of human AB serum following absorption on 50 µl of anti-mouse IgG agarose beads carrying approximately 300 ng of Galα1,3Gal- or non-substituted PSGL1/mIgG$_{2b}$ as estimated in a $^{51}$Cr-release assay.
Figure 2:
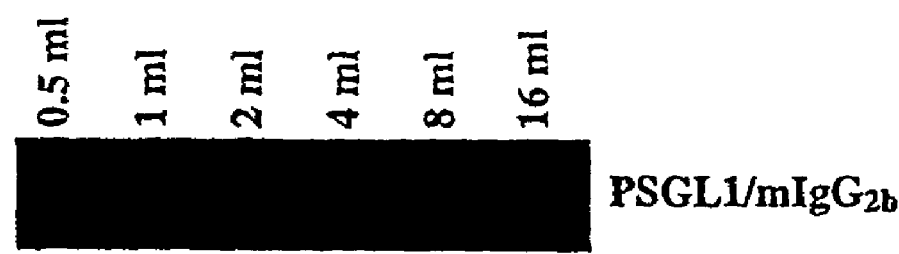

To investigate the importance of the host cell for α-Gal epitope density on, and anti-pig antibody adsorption efficacy of, PSGL-1/mIgG$_{2b}$, the protein, together with the porcine α1,3GalT, was stably expressed in CHO, COS and 293T cells. The level of α-Gal substitution on PSGL-1/mIgG$_{2b}$ and its anti-pig antibody adsorption capacity were dependent on the host cell. PSGL-1/mIgG$_{2b}$ made in COS cells exhibited a 5.3-fold increase in the relative O.D. (GSA-reactivity/anti-mouse IgG reactivity) compared to PSGL-1/mIgG$_{2b}$ made in COS without the α1,3GalT (FIG. 2). Similarly, PSGL-1/mIgG$_{2b}$ made in 293T cells exhibited a 3.1-fold increase in the relative O.D. In contrast, PSGL-1/mIgG$_{2b}$ made in CHO cells exhibited only a 1.8-fold increase (FIG. 2). The anti-pig antibody adsorption efficacy of PSGL-1/mIgG$_{2b}$ made in different host cells correlated to its degree of α-Gal substitution.

Figure 7:
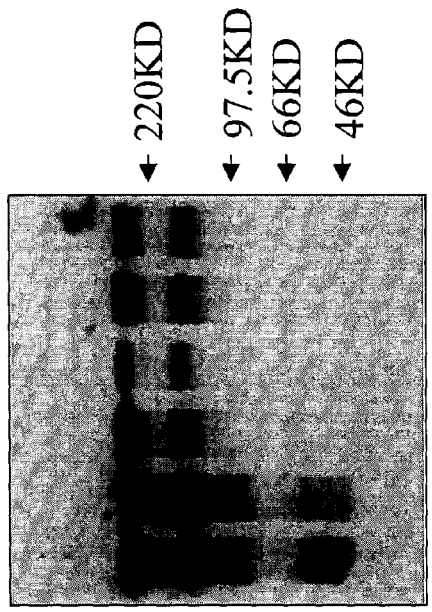
FIG. 7 is a photograph of a Western blot depicting PSGL-1/mIgG$_{2b}$ fusion proteins immunoaffinity purified from supernatants of CHO-K1, COS and 293T cells stably transfected with the PSGL-1/mIgG$_{2b}$ cDNA alone (−) or together with the porcine α1,3 galactosyltransferase cDNA (+).
Figure 7:
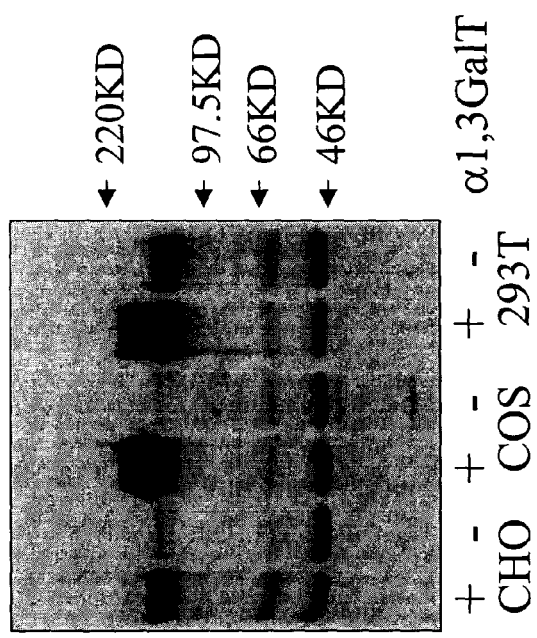
Figure 8:
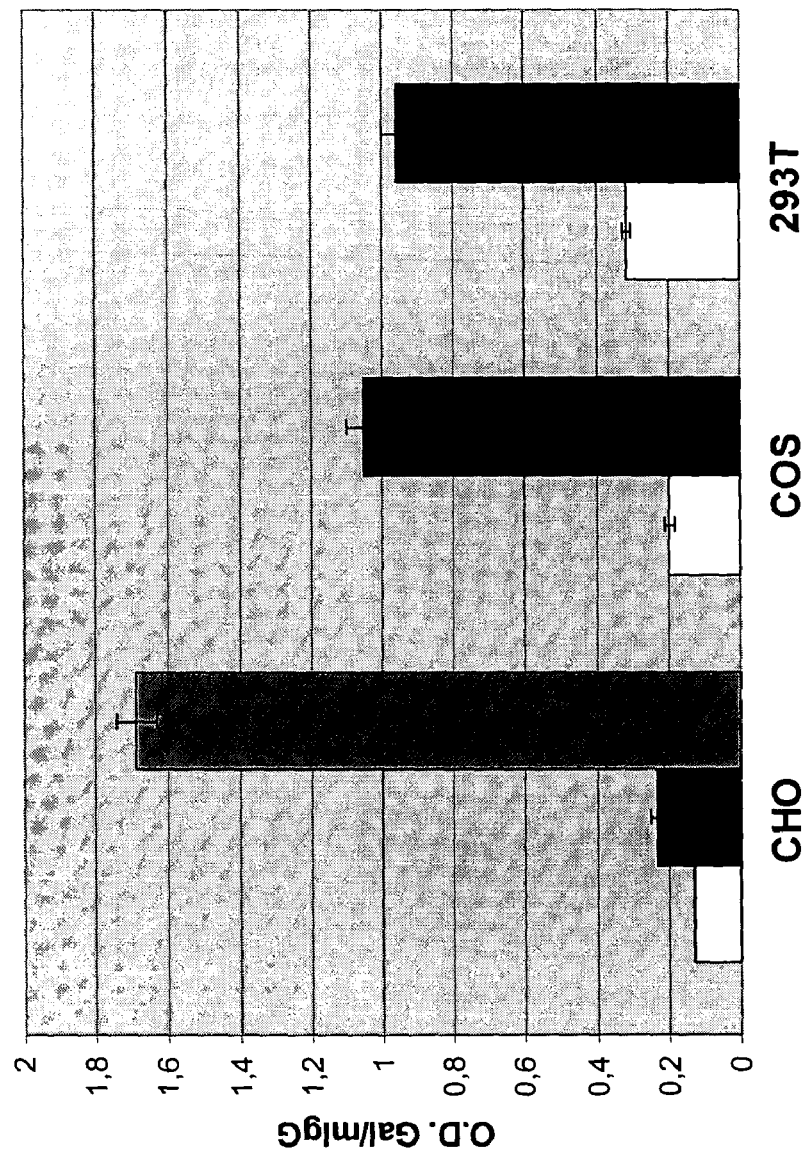
FIG. 8. is a bar chart showing the relative α-Gal epitope density on PSGL-1/mIgG$_{2b}$ expressed by CHO-K1, COS, and 293T cells. The relative α-Gal epitope density on P-selectin glycoprotein ligand-1 —mouse immunoglobulin Fc fusion proteins (PSGL-1/mIgG$_{2b}$) produced in CHO-K1, COS or 293T without (white bars) or with (black bars) co-expression of the pig α1,3galactosyltransferase (GalT) and, for CHO-K1, the core 2 β1,6 N-acetylglucosaminyl transferase (C2 GnT1) (grey bar).

Surprisingly, co-expression of a core 2 β1,6 GlcNAc transferase (C2 GnT1) in CHO cells improved PSGL-1/mIgG$_{2b}$ α-Gal epitope density and anti-pig antibody adsorption efficacy. Moreover, PSGL-1/mIgG$_{2b}$ expressed in CHO cells together with the porcine α1,3GalT and the C2 GnT1 carried three different O-glycans with sequences consistent with terminal Gal-Gal. (Table 2) In contrast, no terminal Gal-Gal epitopes were detected on O-glycans on PSGL-1/mIgG$_{2b}$ expressed in CHO cels without the C2 GnT1. As shown in FIG. 2, the level of α-Gal epitopes on the fusion protein produced in CHO cells expressing both exogenous C2 GnT1 and α1,3GalT was strikingly increased, exceeding the α-Gal epitope levels on the fusion protein made in COS and 293T cells expressing only exogenous α1,3GalT. Additionally, the anti-pig antibody adsorption capacity of the fusion protein was increased (FIG. 3) in CHO cells as compared to COS and 293T cells. Mass spectrometry confirmed that, the increased α-Gal epitope density was due to core 2 branching and lactosamine extensions on O-glycans of PSGL-1/mIgG$_{2b}$ made in CHO cells engineered to express both C2 GnT1 and α1,3GalT (FIGS. 7, 8 and Table II).

The binding of an antibody to a carbohydrate epitope is dependent on the conformation of the presented saccharide. Histo-blood group antigens have been shown to adopt different conformations in solution (Imberty, A. et al., 1995) and anti-blood group antibodies to recognize different areas of the carbohydrate determinant, the so called micro-epitopes, that were conformation-dependent (Imberty, A. et al., 1996). Studies have also shown that a receptor can induce a less energetically favourable conformation when bound to the ligand (Imberty, A. et al., 1993). Studies on two xenoantigens, the α-Gal-LacNAc and α-Gal-Lewis x, revealed that even though the fucose residue of the latter epitope induced a conformational restraint on the lactosamine structure, the terminal Galα1,3Gal disaccharide was rather flexible (Corzana, F. et al., 2002). Accordingly, histo-blood group antigens as well as xenoantigens, both recognized by so called natural antibodies, can adopt several different conformations and it might be difficult to predict the conformation of the epitope that these antibodies recognize. Furthermore, the inner core structure of an oligosaccharide has been shown to influence the binding affinity of the protein-carbohydrate complex although it was most likely not directly involved in the binding (Maaheimo, H. et al., 1995). The structural analysis of the O-glycans expressed on CHO cells co-expressing the α1,3GalT and the C2 GnT1 showed that the α-Gal epitope was expressed on three different oligosaccharides (FIG. 7 and Table II). Thus apart from the effect of the core 2 and lactosamine structure, the N-acetyl- and N-glycolyl neuraminic acid situated on the core 1 branch in two of these oligosaccharides might influence the conformations adopted by these xenoantigens. Also, the sialic acids may be part of the binding epitope. Thus a portion of the xenoreactive antibody repertoire recognizes these branched epitopes with a different binding specificity than the ones recognizing the Galili antigen (Galili, U. et al., 1985). Furthermore, N-glycolyl-neuraminic acid is expressed in pigs (Bouhours, D. et al., 1996; Malykh, Y. N. et al., 2003; Malykh, Y. N. et al., 2001) but not in humans (Varki, A., 2001), and has been shown to be recognized by human xenoreactive antibodies (Zhu, A. et al., 2002). It is therefore possible that glycans containing N-glycolyl neuraminic acid bind yet another group of xenoreactive antibodies.

The invention provides mucin-immunoglobulin fusion proteins (refered to herein as "αGal fusion proteins") containing multiple αGal epitopes that are useful as an absorber for anti-αGal antibodies. For example, the αGal fusion protein are useful in eliminating recipient anti-αGal antibodies from blood or plasma prior to a xenotransplantation. The αGal fusion protein absorbs 10%, 25%, 50%, 60%, 70%, 80%, 90%, 95%, 98% or 100% of anti-αGal antibodies from recipient blood or plasma.

The αGal fusion peptide is more efficient on a carbohydrate molar basis in removing or binding anti-blood group antibodies as compared free saccharides of wild type αGal determinants. The αGal fusion peptide binds 2, 4, 6, 10, 20, 50, 80, 100 or more-fold greater number of anti-αGal antibodies as compared to an equivalent amount of free saccharrides of wild type αGal determinants.

Fusion Polypeptides

In various aspects the invention provides fusion proteins that include a first polypeptide containing at least a portion of a glycoprotein, e.g., a mucin polypeptide linked to a second polypeptide. As used herein, a "fusion protein" or "chimeric protein" includes at least a portion of a mucin polypeptide operatively linked to a non-mucin polypeptide. A "non-mucin polypeptide" refers to a polypeptide of which at least less than 40% of its mass is due to glycans.

A "mucin polypeptide" refers to a polypeptide having a mucin domain. The mucin polypeptide has one, two, three, five, ten, twenty or more mucin domains. The mucin polypeptide is any glycoprotein characterized by a amino acid sequence subsitited with O-glycans. For example a mucin polypeptide has every second or third amino acid being a serine or threonine. The mucin polypeptide is a secreted protein. Alternatively, the mucin polypeptide is a cell surface protein.

Mucin domains are rich in the amino acids threonine, serine and proline, where the oligosaccharides are linked via N-acetylgalactosamine to the hydroxy amino acids (O-glycans). A mucin domain comprises or alternatively consists of an O-linked glycosylation site. A mucin domain has 1, 2, 3, 5, 10, 20, 50, 100 or more O-linked glycosylation sites. Alternatively, the mucin domain comprises or alternatively consists of a N-linked glycosylation site. A mucin polypeptide has 50%, 60%, 80%, 90%, 95% or 100% of its mass due to the glycan. A mucin polypeptide is any polypeptide encode for by a MUC genes (i.e., MUC1, MUC2, MUC3, MUC4, MUC5a, MUC5b, MUC5c, MUC6, MUC11, MUC12,etc.). Alternatively, a mucin polypeptide is P-selectin glycoprotein ligand 1 (PSGL-1), CD34, CD43, CD45, CD96, GlyCAM-1, MAdCAM, red blood cell glycophorins, glycocalicin, glycophorin, sialophorin, leukosialin, LDL-R, ZP3, and epiglycanin. Preferably, the mucin is PSGL-1. PSGL-1 is a homodimeric glycoprotein with two disulfide-bonded 120 kDa subunits of type 1 transmembrane topology, each containing 402 amino acids. In the extracellular domain there are 15 repeats of a 10-amino acid consensus sequence A Q(M) T T P(Q)P(LT) A A(PG) T(M) E that contains 3 or 4 potential sites for addition of O-linked oligosaccharides. PSGL-1 is predicted to have more than 53 sites for O-linked glycosylation and 3 sites for N-linked glycosylation in each monomer.

The mucin polypeptide contains all or a portion of the mucin protein. Alternatively, the mucin protein includes the extracellular portion of the polypeptide. For example, the mucin polypeptide includes the extracellular portion of PSGL-1 or a portion thereof (e.g., amino acids 19-319 disclosed in GenBank Accession No. A57468). The mucin polypeptide also includes the signal sequence portion of PSGL-1 (e.g., amino acids 1-18), the transmembrane domain (e.g., amino acids 320-343), and the cytoplamic domain (e.g., amino acids 344-412).

Within an αGal fusion protein of the invention the mucin polypeptide corresponds to all or a portion of a mucin protein. For example, an αGal fusion protein contains at least a portion of a mucin protein. "At least a portion" is meant that the mucin polypeptide contains at least one mucin domain (e.g., an O-linked glycosylation site). Optionally, the mucin protein comprises the extracellular portion of the polypeptide. For example, the mucin polypeptide comprises the extracellular portion of PSGL-1.

The mucin polypeptide is decorated with a glycan repertoire as shown in Table. 2. For example the mucin polypeptide has one, two, three, four, five or more the carbohydrate sequences recited in Table 2. For example the mucin polypeptide has the glycan repertoire including Hex-HexNol-HexN-Hex-Hex; NeuAc-Hex-HexNol-HexN-Hex-Hex; and NeuGc-Hex-HexNol-HexN-Hex-Hex. The mucin polypeptide has one, two, three, four, five or more terminal αGal sugars. Preferably, the terminal sugars are expressed on two, three, four, five or more different oligosaccharides. Optionally, the mucin includes N-acetyl neuraminic acid, N-glycolyl neuraminic acid, and/or sialic acid. Additionally, the oligosaccharides of the mucin includes core 2 braching, core 1 branching, and lactosamoine extentions.

The first polypeptide is glycosylated by one or transferases. The transferase is exogenous. Alternatively, the transferase is endogenous. The first polypeptide is glycosylated by 2, 3, 5 or more transferases. Glycosylation is sequential or consecutive. Alternatively glycosylation is concurrent or random, i.e., in no particular order. For example the first polypeptide is glycosylated by an α1,3 galactosyltransferase. Suitable sources for α1,3 galactosyltransferase include GenBank Accession Nos. AAA73558, L36150, BAB30163, AK016248, E46583 or P50127 and are incorporated herein by reference in their entirety. Alternatively, the first polypeptide is glycosylated by core 2 branching enzyme or an N acetylglucosaminyltransferase such as a β 1,6 N-acetylglucosaminyltransferase. Suitable sources for a β1,6 N-acetylglucosaminyltransferase include GenBank Accession Nos. CAA79610, Z19550, BAB66024 or AP001515. Preferably, the first polypeptide is glycosylated by both an 1,3 galactosyltransferase and a β1,6 N-acetylglucosaminyltransferase.

Within the fusion protein, the term "operatively linked" is intended to indicate that the first and second polypeptides are chemically linked (most typically via a covalent bond such as a peptide bond) in a manner that allows for O-linked glycosylation of the first polypeptide. When used to refer to nucleic acids encoding a fusion polypeptide, the term operatively linked means that a nucleic acid encoding the mucin polypeptide and the non-mucin polypeptide are fused in-frame to each other. The non-mucin polypeptide can be fused to the N-terminus or C-terminus of the mucin polypeptide.

Optionally, the αGal fusion protein is linked to one or more additional moieties. For example, the αGal fusion protein is additionally be linked to a GST fusion protein in which the αGal fusion protein sequences are fused to the C-terminus of the GST (i.e., glutathione S-transferase) sequences. Such fusion proteins can facilitate the purification of αGal fusion protein. Alternatively, the αGal fusion protein is additionally be linked to a solid support. Various solid support are know to those skilled in the art. Such compositions can facilitate removal of anti-αGal antibodies. For example, the αGal fusion protein is linked to a particle made of, e.g., metal compounds, silica, latex, polymeric material; a microtiter plate; nitrocellulose, or nylon or a combination thereof. The αGal fusion proteins linked to a solid support are used as an absorber to remove anti-αGal antibodies from a biological sample, such as blood or plasma.

The fusion protein includes a heterologous signal sequence (i.e., a polypeptide sequence that is not present in a polypeptide encoded by a mucin nucleic acid) at its N-terminus. For example, the native mucin signal sequence can be removed and replaced with a signal sequence from another protein. In certain host cells (e.g., mammalian host cells), expression and/or secretion of polypeptide can be increased through use of a heterologous signal sequence.

An chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al. (eds.) CURRENT PROTOCOLS IN MOLECULAR BIOLOGY, John Wiley & Sons, 1992). Moreover, many expression vectors are commercially available that encode a fusion moiety (e.g., an Fc region of an immunoglobulin heavy chain). A PSGL-1 encoding nucleic acid can be cloned into such an expression vector such that the fusion moiety is linked in-frame to the immunoglobulin protein. An exemplary PSGL-1 expression vector include SEQ ID NO:21

An αGal fusion polypeptides exist as oligomers, such as dimers, trimers or pentamers. Preferably, the αGal fusion polypeptide is a dimer.

The first polypeptide, and/or nucleic acids encoding the first polypeptide, is constructed using mucin encoding sequences are known in the art. Suitable sources for mucin polypeptides and nucleic acids encoding mucin polypeptides include GenBank Accession Nos. NP663625 and NM145650, CAD10625 and AJ417815, XP140694 and XM140694, XP006867 and XM006867 and NP00331777 and NM009151 respectively, and are incorporated herein by reference in their entirety.

Alternatively, the mucin polypeptide moiety is provided as a variant mucin polypeptide having a mutation in the naturally-occurring mucin sequence (wild type) that results in increased carbohydrate content (relative to the non-mutated sequence). For example, the variant mucin polypeptide comprised additional O-linked glycosylation sites compared to the wild-type mucin. Alternatively, the variant mucin polypeptide comprises an amino acid sequence mutations that results in an increased number of serine, threonine or proline residues as compared to a wild type mucin polypeptide. This increased carbohydrate content can be assessed by determining the protein to carbohydrate ratio of the mucin by methods know to those skilled in the art.

In some embodiments, the mucin polypeptide moiety is provided as a variant mucin polypeptide having mutations in the naturally-occurring mucin sequence (wild type) that results in a mucin sequence more resistant to proteolysis (relative to the non-mutated sequence).

The first polypeptide includes full-length PSGL-1. Alternatively, the first polypeptide comprise less than full-length PSGL-1 polypeptide such as the extracellular portion of PSGL-1. For example the first polypeptide less than 400 amino acids in length, e.g., less than or equal to 300, 250, 150, 100, 50, or 25 amino acids in length. Exemplary PSGL-1 polypeptide and nucleic acid sequences include GenBank Access No: XP006867; XM006867; XP140694 and XM140694.

The second polypeptide is preferably soluble. The second polypeptide includes a sequence that facilitates association of the αGal fusion polypeptide with a second mucin polypeptide. Preferably, the second polypeptide includes at least a region of an immunoglobulin polypeptide. "At least a region" is meant to include any portion of an immunoglobulin molecule, such as the light chain, heavy chain, FC region, Fab region, Fv region or any fragment thereof. Immunoglobulin fusion polypeptide are known in the art and are described in e.g., U.S. Pat. Nos. 5,516,964; 5,225,538; 5,428,130; 5,514, 582; 5,714,147; and 5,455,165.

The second polypeptide comprises a full-length immunoglobulin polypeptide. Alternatively, the second polypeptide comprise less than full-length immunoglobulin polypeptide, e.g., a heavy chain, light chain, Fab, Fab$_2$, Fv, or Fc. Preferably, the second polypeptide includes the heavy chain of an immunoglobulin polypeptide. More preferably the second polypeptide includes the Fc region of an immunoglobulin polypeptide.

In another aspect of the invention the second polypeptide has less effector function that the effector function of a Fc region of a wild-type immunoglobulin heavy chain. Fc effector function includes for example, Fc receptor binding, complement fixation and T cell depleting activity. (see for example, U.S. Pat. No. 6,136,310) Methods of assaying T cell depleting activity, Fc effector function, and antibody stability are known in the art. In one embodiment the second polypeptide has low or no affinity for the Fc receptor. In an alternative embodiment, the second polypeptide has low or no affinity for complement protein C1q.

Another aspect of the invention pertains to vectors, preferably expression vectors, containing a nucleic acid encoding mucin polypeptides, or derivatives, fragments, analogs or homologs thereof. In various aspects the vector contains a nucleic acid encoding a mucin polypeptide operably linked to an nucleic acid encoding an immunoglobulin polypeptide, or derivatives, fragments analogs or homologs thereof. Additionally, the vector comprises a nucleic acid encoding a α1,3 galactosyltransferase, a core 1,6,-N-actetylglucosaminyltransferase or any combination thereof. The transferase facilitates the addition of αGal determinants on the peptide backbone of the mucin portion of the αGal fusion protein. Exemplary vectors include SEQ ID NO:1, 11 or 21. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to includes promoters, enhancers and other expression control elements (e.g., polyadenylation signals). Such regulatory sequences are described, for example, in Goeddel, GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., ABO fusion polypeptides, mutant forms of ABO fusion polypeptides, etc.).

The recombinant expression vectors of the invention can be designed for expression of αGal fusion polypeptides in prokaryotic or eukaryotic cells. For example, αGal fusion polypeptides can be expressed in bacterial cells such as *Escherichia coli*, insect cells (using baculovirus expression vectors) yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988. *Gene* 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) *Gene* 69:301-315) and pET 11d (Studier et al., GENE EXPRESSION TECHNOLOGY: METHODS IN ENZYMOLOGY 185, Academic Press, San Diego, Calif. (1990) 60-89).

One strategy to maximize recombinant protein expression in *E. coli* is to express the protein in a host bacteria with an impaired capacity to proteolytically cleave the recombinant protein. See, e.g., Gottesman, GENE EXPRESSION TECHNOLOGY: METHODS IN ENZYMOLOGY 185, Academic Press, San Diego, Calif. (1990) 119-128. Another strategy is to alter the nucleic acid sequence of the nucleic acid to be inserted into an expression vector so that the individual codons for each amino acid are those preferentially utilized in *E. coli* (see, e.g., Wada, et al., 1992. *Nucl. Acids Res.* 20: 2111-2118). Such alteration of nucleic acid sequences of the invention can be carried out by standard DNA synthesis techniques.

In another embodiment, the αGal fusion polypeptide expression vector is a yeast expression vector. Examples of vectors for expression in yeast *Saccharomyces cerivisae* include pYepSec1 (Baldari, et al., 1987. *EMBO J.* 6: 229-234), pMFa (Kurjan and Herskowitz, 1982. *Cell* 30: 933-943), pJRY88 (Schultz et al., 1987. *Gene* 54: 113-123), pYES2 (Invitrogen Corporation, San Diego, Calif.), and picZ (InVitrogen Corp, San Diego, Calif.).

Alternatively, αGal fusion polypeptide can be expressed in insect cells using baculovirus expression vectors. Baculovirus vectors available for expression of proteins in cultured insect cells (e.g., SF9 cells) include the pAc series (Smith, et al., 1983. *Mol. Cell. Biol.* 3: 2156-2165) and the pVL series (Lucklow and Summers, 1989. *Virology* 170: 31-39).

In yet another embodiment, a nucleic acid of the invention is expressed in mammalian cells using a mammalian expression vector. Examples of mammalian expression vectors include pCDM8 (Seed, 1987. *Nature* 329: 840) and pMT2PC (Kaufman, et al., 1987. *EMBO J.* 6: 187-195). When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, αGal fusion polypeptides is expressed in bacterial cells such as *E. coli*, insect cells, yeast or mammalian cells (such as human, Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding glycoprotein Ibα fusion polypeptides or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) αGal fusion polypeptides. Accordingly, the invention further provides methods for producing αGal fusion polypeptides using the host cells of the invention. In one embodiment, the method comprises culturing the host cell of invention (into which a recombinant expression vector encoding αGal fusion polypeptides has been introduced) in a suitable medium such that αGal fusion polypeptides is produced. In another embodiment, the method further comprises isolating αGal polypeptide from the medium or the host cell.

The αGal fusion polypeptides may be isolated and purified in accordance with conventional conditions, such as extraction, precipitation, chromatography, affinity chromatography, electrophoresis or the like. For example, the immunoglobulin fusion proteins may be purified by passing a solution through a column which contains immobilized protein A or protein G which selectively binds the Fc portion of the fusion protein. See, for example, Reis, K. J., et al., J. Immunol. 132:3098-3102 (1984); PCT Application, Publication No. WO87/00329. The fusion polypeptide may the be eluted by treatment with a chaotropic salt or by elution with aqueous acetic acid (1 M).

Alternatively, an αGal fusion polypeptides according to the invention can be chemically synthesized using methods known in the art. Chemical synthesis of polypeptides is described in, e.g., A variety of protein synthesis methods are common in the art, including synthesis using a peptide synthesizer. See, e.g., *Peptide Chemistry, A Practical Textbook*, Bodansky, Ed. Springer-Verlag, 1988; Merrifield, *Science* 232: 241-247 (1986); Barany, et al, *Intl. J. Peptide Protein Res.* 30: 705-739 (1987); Kent, *Ann. Rev. Biochem.* 57:957-989 (1988), and Kaiser, et al, *Science* 243: 187-198 (1989). The polypeptides are purified so that they are substantially free of chemical precursors or other chemicals using standard peptide purification techniques. The language "substantially free of chemical precursors or other chemicals" includes preparations of peptide in which the peptide is separated from chemical precursors or other chemicals that are involved in the synthesis of the peptide. In one embodiment, the language "substantially free of chemical precursors or other chemicals" includes preparations of peptide having less than about 30% (by dry weight) of chemical precursors or non-peptide chemicals, more preferably less than about 20% chemical precursors or non-peptide chemicals, still more preferably less than about 10% chemical precursors or non-peptide chemicals, and most preferably less than about 5% chemical precursors or non-peptide chemicals.

Chemical synthesis of polypeptides facilitates the incorporation of modified or unnatural amino acids, including D-amino acids and other small organic molecules. Replacement of one or more L-amino acids in a peptide with the corresponding D-amino acid isoforms can be used to increase the resistance of peptides to enzymatic hydrolysis, and to enhance one or more properties of biologically active peptides, i.e., receptor binding, functional potency or duration of action. See, e.g., Doherty, et al., 1993. *J. Med. Chem.* 36: 2585-2594; Kirby, et al., 1993. *J. Med. Chem.* 36:3802-3808; Morita, et al., 1994. *FEBS Lett.* 353: 84-88; Wang, et al., 1993. *Int. J. Pept. Protein Res.* 42: 392-399; Fauchere and Thiunieau, 1992. *Adv. Drug Res.* 23: 127-159.

Introduction of covalent cross-links into a peptide sequence can conformationally and topographically constrain the polypeptide backbone. This strategy can be used to develop peptide analogs of the fusion polypeptides with increased potency, selectivity and stability. Because the conformational entropy of a cyclic peptide is lower than its linear counterpart, adoption of a specific conformation may occur with a smaller decrease in entropy for a cyclic analog than for an acyclic analog, thereby making the free energy for binding more favorable. Macrocyclization is often accomplished by forming an amide bond between the peptide N- and C-termini, between a side chain and the N- or C-terminus [e.g., with $K_3Fe(CN)_6$ at pH 8.5] (Samson et al., *Endocrinology*, 137: 5182-5185 (1996)), or between two amino acid side chains. See, e.g., DeGrado, *Adv Protein Chem*, 39: 51-124 (1988). Disulfide bridges are also introduced into linear sequences to reduce their flexibility. See, e.g., Rose, et al., *Adv Protein Chem*, 37: 1-109 (1985); Mosberg et al., *Biochem Biophys Res Commun*, 106: 505-512 (1982). Furthermore, the replacement of cysteine residues with penicillamine (Pen, 3-mercapto-(D) valine) has been used to increase the selectivity of some opioid-receptor interactions. Lipkowski and Carr, *Peptides: Synthesis, Structures, and Applications*, Gutte, ed., Academic Press pp. 287-320 (1995).

Methods of Treating or Preventing Hyperacute Rejection

Also included in the invention are methods of treating or preventing hyperactute rejection (HAR), e.g., xenotransplant rejection. Such transplants include but are not limited to kidney, liver, skin, pancreas, cornea, or heart. HAR is meant to include any antibody mediated graft rejection by the recipient. Hyperacute rejection of a transplanted organ occurs within seconds or minutes of exposing the organ to the recipient's circulation. The organ quickly becomes pale, and will undergo necrosis if left in the recipient's body. This hyperacute reaction occurs because of preformed antibodies against the donor organ. HAR is most common in multiparous women, as they have been exposed in utero to numerous non-self antigens. Recipients who have received multiple blood transfusions are also at risk.

The method includes contacting a biological sample from a subject with the αGal fusion peptide of the invention. The biological sample is for example, blood, i.e., whole blood or plasma. The sample is know to or suspected of comprising an antibody, e.g., an anti-blood group antibody. In some aspects, the biological sample is withdrawn from the subject prior to contacting the sample with the αGal fusion polypeptide. The biological sample is contacted with the αGal fusion peptide under conditions to allow formation of an αGal fusion peptide-anti-blood group antibody complex. The αGal fusion peptide-complex, if present is separated from the biological sample to eliminate the anti-blood group antibodies and the biological sample is reinfused into the subject. HAR is also treated or prevented by administering to a subject an αGal fusion polypeptide of the invention.

The subject can be e.g., any mammal, e.g., a human, a primate, mouse, rat, dog, cat, cow, horse, pig. The treatment is administered prior to the subject receiving a xenotransplant. Alternatively, treatment is administered after a subject receives an xenotransplant.

The biological sample is contacted with the αGal fusion protein by methods know to those skilled in the art. For example, plasmapheresis or extracorporeal immunoabsorption.

Essentially, any disorder, which is etiologically linked to an HAR is considered amenable to prevention or to treatment. HAR is treated or prevent when the survival rate of the organ transplant is greater than an organ transplant not treated by the method of the invention. By survival rate of the transplant is meant the time before the transplant is rejected by the recipient For example, HAR is treated or prevent when the transplant survives at least 1, 2, 4 or 8 weeks after transplant. Preferably, the transplant survives 3, 6, 13 months. More preferably, the transplant survives 2, 3, 5 or more years.

Methods of Removing αGal Antibodies from a Sample

Also included in the invention are methods of removing or depleting anti-αGal antibodies from a sample. The sample is a biological fluid such as blood or plasma. Alternatively, the sample is a biological tissue, such as heart tissue, liver tissue, skin, or kidney tissue. The method includes contacting a sample with the αGal fusion peptide of the invention. The sample is contacted with the αGal fusion peptide under conditions to allow formation of an αGal fusion peptide-anti-αGal antibody complex. The αGal fusion peptide-antibody complex, if present is separated from the biological sample to remove or deplete the anti-αGal antibodies.

Pharmaceutical Compositions Including αGal Fusion Polypeptides or Nucleic Acids Encoding Same The ABO fusion proteins, or nucleic acid molecules encoding these fusion proteins, (also referred to herein as "Therapeutics" or "active compounds") of the invention, and derivatives, fragments, analogs and homologs thereof, can be incorporated into pharmaceutical compositions suitable for administration. Such compositions typically comprise the nucleic acid molecule, protein, or antibody and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The active agents disclosed herein can also be formulated as liposomes. Liposomes are prepared by methods known in the art, such as described in Epstein et al., Proc. Natl. Acad. Sci. USA, 82: 3688 (1985); Hwang et al., Proc. Natl. Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., an ABO fusion protein) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

In some embodiments, oral or parenteral compositions are formulated in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see, e.g., U.S. Pat. No. 5,328,470) or by stereotactic injection (see, e.g., Chen, et al., 1994. *Proc. Natl. Acad. Sci. USA* 91: 3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

Sustained-release preparations can be prepared, if desired. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid andγ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

The pharmaceutical compositions can be included in a container, pack, or dispenser together with instructions for administration.

Abbreviations

The following abbreviations are used herein:

ADCC, antibody-dependent cellular cytotoxicity; BSA, bovine serum albumin; DXR, delayed xenorejection; ELISA, enzyme-linked immunosorbent assay; FT, fucosyltransferase; Gal, D-galactose; GT, galactosyltransferase; Gic, D-glucose; GlcNAc, D-N-acetylglucosamine; GlyCAM-1, glycosylation-dependent cell adhesion molecule-1; HAR, hyperacute rejection; Ig, immunoglobulin; MAdCAM, mucosal addressin cell adhesion molecule; PAEC, porcine aortic endothelial cells; PBMC, peripheral blood mononuclear cells; PSGL-1, P-selectin glycoprotein ligand-1; RBC, red blood cell; SDS-PAGE, sodium dodecyl sulphate—polyacrylamide gel electrophoresis; Hex, hexose; HexNAc, N-acetyl hexosamine; NeuAc, N-acetyl neuraminic acid; NeuGc, N-glycolyl neuraminic acid; and HexNol is the open (not the ring) form of N-acetyl hexosamine.

The invention will be further illustrated in the following non-limiting examples.

EXAMPLE 1

Transient Expression of Substituted Recominant P-Selectin Glycoprotein Ligand/Immunoglobulin Fusion Proteins General Methods Cell culture COS-7 m6 cells (35) and the SV40 Large T antigen immortalized porcine aortic endothelial cell line, PEC-A (36), were passaged in Dulbecco's modified Eagle's medium (DMEM), with 10% fetal bovine serum (FBS) and 25 µg/ml gentamicin sulfate. The human erythroleukemic cell line, K562, and the Burkitt's lymphoma cell line, Raji, were obtained from ATCC and cultured in HEPES-buffered RPMI 1640 with 10% FBS, 100 IU/ml penicillin and 100 µg/ml streptomycin.

Construction of Expression Vectors

The porcine α 1,3 GT (37-39) was PCR amplified off pig spleen cDNA using a forward primer having six codons of complementarity to the 5' end of the coding sequence, a Kozak translational initiation concensus sequence and a Hind3 restriction site, and a reverse primer with six codons of complementarity to the 3' end of the coding sequence, a translational stop and a Not1 restriction site. The amplified α 1,3GT cDNA was cloned into the polylinker of CDM8 using Hind3 and Not1 (35). The P-selectin glycoprotein ligand-1 (PSGL-1) a highly glycosylated mucin-type protein mediating binding to P-selectin (40) coding sequence was obtained by PCR off an HL-60 cDNA library, cloned into CDM8 with Hind3 and Not1, and confirmed by DNA sequencing. The mucin/immunoglobulin expression plasmid was constructed by fusing the PCR-amplified cDNA of the extracellular part of PSGL-1 in frame via a BamH1 site, to the Fc part (hinge, CH2 and CH3) of mouse $IgG_{2b}$ carried as an expression casette in CDM7 (Seed, B. et al).

Production and Purification of Secreted Mucin/Immunoglobulin Chimeras

COS m6 cell were transfected using the DEAE-dextran protocol and 1 µg of CsCl-gradient purified plasmid DNA per ml transfection cocktail. COS cells were transfected at approximately 70% confluency with empty vector (CDM8), the PSGL1/mIgG.sub.2b plasmid alone or in combination with the α1,3GT encoding plasmid. Transfected cells were trypsinized and transferred to new flasks the day after transfection. Following adherence for approximately 12 hrs, the medium was discarded, the cells washed with phosphate buffered saline (PBS), and subsequently incubated another 7 days in serum-free, AIM-V medium (cat.nr. 12030, Life technologies Inc.). After incubation, supernatants were collected, debris spun down (1400×g, 20 minutes), and NaN.sub.3 added to 0.02%. PSGL1/mIgG.sub.2b fusion protein was purified on goat anti-mouse IgG agarose beads (A-6531, Sigma) by rolling head over tail, over night at 4.degree. C. The beads were washed in PBS and subsequently used for SDS-PAGE and Western blot analysis, or for absorption of human AB serum and purified human immunoglobulins.

Purification of human IgG, IgM and IgA

Human IgG, IgM and IgA were purified from human AB serum—pooled from more than 20 healthy blood donors—using goat anti-human IgG (Fc specific; A-3316, Sigma), IgM (µ-chain specific; A-9935, Sigma), and IgA (α-chain specific; A-2691, Sigma) agarose beads. Briefly, 5 ml of slurry (2.5 ml packed beads) were poured into a column of 10 mm diameter and washed with PBS. Ten milliter of human pooled AB serum was applied at 1 ml/minute using a peristaltic pump, washed with several column volumns of PBS, and eluted with 0.1M glycine, 0.15M NaCl, pH 2.4 using a flow rate of 1 ml/minute. One milliliter fractions were collected in tubes containing 0.7 ml of neutralizing buffer (0.2M Tris/HCl, pH 9). The absorption at 280 nm was read spectrophotometrically and tubes containing protein were pooled dialyzed against 1% PBS, and lyophilized. Lyophilized immunoglobulins were resuspended in distilled water and the concentrations adjusted to 16 mg/ml for IgG, 4 mg/ml for IgA and 2 mg/ml for IgM.

SDS-PAGE and Western Blotting.

SDS-PAGE was run by the method of Leammli with a 5% stacking gel and a 6 or 10% resolving gel using a vertical Mini-PROTEAN II electrophoresis system (Bio-Rad, Herculus, Calif.) (41). Separated proteins were electrophoretically blotted onto Hybond.TM.-C extra membranes (Amersham) using a Mini Trans-Blot electrophoretic transfer cell (Bio-Rad, Herculus, Calif.) (42). Protein gels were stained using a silver staining kit according to the manufacturer's instructions (Bio-Rad, Herculus, Calif.). Following blocking for at least 2 hrs in 3% BSA in PBS, the membranes were probed for 2 hrs in room temperature with peroxidase-conjugated Bandereia simplicifolia isolectin B.sub.4 (L-5391, Sigma) diluted to a concentration of 1 µg/ml in PBS, pH 6.8 containing 0.2 mM $CaCl_2$. The membranes were washed 5 times with PBS, pH 6.8, and bound lectin was visualized by chemiluminescens using the ECL.TM. kit according to the instructions of the manufacturer (Amersham).

Quantification of PSGLb1/mIgG$_{2b}$ by Anti-Mouse IgG Fc ELISA

The concentration of fusion protein in cell culture supernatants before and after absorption was determined by a 96-well ELISA assay, in which fusion proteins were captured with an affinity purified, polyclonal goat anti-mouse IgG Fc antibody (cat.nr. 55482, Cappel/Organon Teknika, Durham, N.C.). Following blocking with 3% BSA in PBS, the fusion proteins were captured and detected with a peroxidase-conjugated, affinity purified, polyclonal anti-mouse IgG Fc antibody (cat.nr. 55566, Organon Teknika, Durham, N.C.) using O-phenylenediamine dihydrochloride as substrate (Sigma). The plate was read at 492 nm and the ELISA calibrated using a dilution series of purified mouse IgG Fc fragments (cat.nr. 015-000-008, Jackson ImmunoResearch Labs., Inc., West Grove, Pa.) resuspended in AIM V serum-free medium.

Porcine Aortic Endothelial Cell ELISA

PEC-A cells were seeded at a density of 15000 cells/well in gelatin-coated 96-well plates (Nunclon, Denmark) and cultured for 48 hrs in AIM V serum-free medium. The plate was washed 5 times in 0.15M NaCl$_2$ containing 0.02% Tween 20 and incubated for 1 hr in room temperature with 50.mu.l/well of purified human IgG, IgM, and IgA in PBS, starting at a concentration of 8, 1, and 2 mg/ml, respectively. The plate was washed again as above, and 50 µl of alkaline phosphatase-conjugated goat anti-human IgG (.gamma.-chain specific; A3312, Sigma), IgM (µ-chain specific; A1067, Sigma) and IgA α-chain specific; A3062, Sigma) F(ab)'$_2$ fragments diluted, 1:200 in PBS were added and incubated for 1 hr at room temperature. The plate was washed as above, incubated with the substrate p-nitrophenyl phosphate (Sigma 104-105), and read at 405 nm.

Porcine Aortic Endothelial Cell Cytotoxicity Assay

PEC-A cells were seeded and cultured in 96-well plates as described for the PEC-A ELISA. Following 48 hrs of culture, the cells were loaded for 1 hr at 37.degree. C. with Na$_2$+$^{51}$CrO$_4$ (cat.nr. CJS4, Amersham), 1 µCi/well, and washed 3 times with AIM V medium. Fifty microliter of serially diluted, absorbed or non-absorbed human AB serum or purified human IgG, IgA, or IgM antibodies were added together with 50 µl of rabbit serum (Cat. no. 439665, Biotest AG, Dreieich, Germany) as a source of complement. Following 4 hrs incubation at 37.degree. C. in a 5% Co.sub.2 atmosphere, the supernatants were harvested using a Skatron supernatant collection system (Skatro Instruments, Norway) and analyzed in a .gamma.-counter (1282 Compugamma, LKB Wallac). Each serum and Ig sample were analyzed in triplicate. The percent killing was calculated as the measured minus the spontaneous release divided by the difference between the maximum and the spontaneous release.

Antibody-Dependent Cellular Cytotoxicity (ADCC)

Human PBMC were isolated from fresh buffy coats prepared from healthy donors at the Blood bank of the South hospital, Stockholm. Six milliliter of buffy coat was mixed in a 50 ml polypropylene tube with 15 ml of PBS containing 1 mg/ml BSA and 3.35 mg/ml EDTA. Following centrifugation at 500 g for 10 minutes, the platelet rich supernatant was discarded, and 6 ml of the lower phase was mixed with 6 ml of Hank's balanced salt solution (HBSS), and underlayered with 6 ml of Lymphoprep.TM. (Nycomed Pharma AS). Following centrifugation (800×g, 20 min.), the interface was transferred to a new tube, washed three times in HBSS, and resuspended in serum-free AIM V medium. The final step in the effector cell preparation was to transfer the PBMC to tissue culture flasks that were incubated for 1 hr at 37° C. and 5% CO$_2$ to remove plastic-adherent cells. Target cells were K562 and Raji cells kept as described above, or PEC-A cells that had been trypsinized the day before the assay and subsequently cultured in AIM V serum-free medium to prevent readhesion to the plastic surface. At the time for the assay the PEC-A cells were washed off the bottom of the flask. Target cells were loaded with Na$_2$$^{51}$CrO$_4$, 100 µCi/1×10$^6$ cells, for 1 hr at 37° C., washed 3 times in HBSS and resuspended in AIM V to a final concentration of 5×10$^4$/ml. Five thousand target cells were added to each well with effector cells in 200 µl AIM V medium with and without 10% heat-inactivated, human AB serum at an effector (E):target (T) ratio ranging from 50:1 in two-fold dilutions to 6.25:1.

Spontaneous release was read in wells with 5 000 target cells incubated in 200 µl AIM V medium without effector cells and maximum release was read in wells where 5 000 target cells in 100 µl AIM V were incubated with 100 µl 5% Triton X-100. Each E:T ratio was analyzed in triplicate. Following incubation at 37° C. for 4 hrs, the supernatants were harvested using a Skatron supernatant collection system (Skatro Instruments, Norway) and analyzed in a .gamma.-counter (LKB Wallac). The percent killing was calculated as the measured minus the spontaneous release divided by the difference between the maximum and the spontaneous release.

Results

Expression and Characterization of the PSGL1/mIgG$_{2b}$ Fusion Protein.

Figure 1:
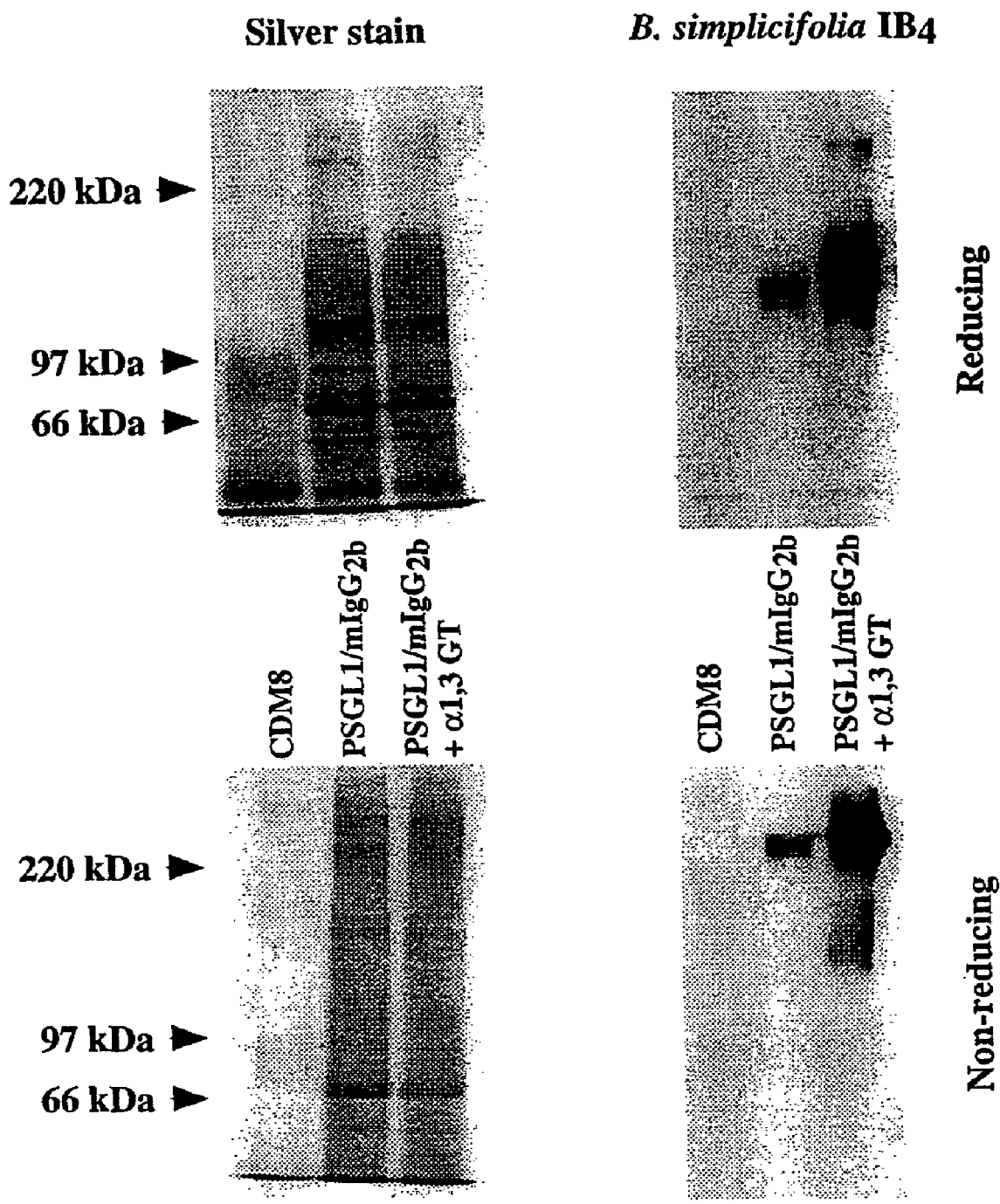
FIG. 1. are photographs of SDS-PAGE of proteins isolated from supernatants of COS cells transfected with vector alone (CDM8), PSGL1/mIgG$_{2b}$, or PSGL1/mIgG$_{2b}$ and porcine α1,3GT expression plasmids. These were subsequently probed with peroxidase-conjugated *Bandeireia simplicifolia* isolectin B$_4$ lectin and visualized by chemiluminescens to detect Galα1,3Gal epitopes on immunopurified proteins.

Supernatants from COS-7 m6 cells transfected with the vector plasmid CDM8, the PSGL1/mIgG$_{2b}$ plasmid, or the, PSGL1/mIgG$_{2b}$ together with the porcine α1,3 GT plasmid, were collected approximately 7 days after transfection. Secreted mucin/Ig fusion proteins were purified by absorption on anti-mouse IgG agarose beads and subjected to SDS-PAGE and Western blotting using the Bandereia simplicifolia isolectin B$_4$ (BSA IB4) for detection. As seen in FIG. 1, the fusion protein migrated under reducing conditions as a broad band with an apparent molecular weight of 145 kDa that stained relatively poorly with silver. The heterogeneity in size, approximately 125 to 165 kDa, and poor stainability is in concordance with previous observations with respect to the behavior of highly glycosylated, mucin-type proteins (43, 44). The fusion protein is most likely produced as a homodimer because SDS-PAGE under non-reducing conditions revealed a double-band of an apparent molecular weight of more than 250 kDa. The amounts of fusion protein affinity-purified from the two supernatants derived from the same number of COS cells transfected with the PSGL1/mIgG$_{2b}$ plasmid alone or together with the α1,3GT plasmid, respectively, were similar. Probing the electroblotted membranes with BSA IB.sub.4 revealed strong staining of the fusion protein obtained following cotransfection with the porcine α1,3 GT (FIG. 1). It is clear, though, that the PSGL1/mIgG$_{2b}$ fusion protein produced in COS-7 m6 cells without cotransfection of the α1,3 GT cDNA also exhibited weak staining with the BSA IB$_4$ lectin, in spite of the fact that COS cells are derived from the Simian monkey—an old world monkey lacking α1,3 GT activity. This indicates that the BSA IB.$_4$ lectin has a slightly broader specificity than just Galα1,3Gal epitopes (45). Nevertheless, cotransfection of the porcine α1,3GT cDNA supported the expression of a highly Galα1, 3Gal-substituted PSGL1/mIgG$_{2b}$ fusion protein.

Quantification of PSGL1/mIgG$_{2b}$ chimeras in supernatants of transfected COS cells, and on goat anti-mouse IgG agarose beads following absorption. A sandwich ELISA was employed to quantify the amount of PSGL1/mIgG$_{2b}$ in the supernatants of transfected COS cells. Typically, 5 culture flasks (260 ml flasks, Nunclon.TM.) with COS cells at 70% confluence were transfected and incubated as described in materials and methods. Following an incubation period of 7 days in 10 ml of AIM V medium per flask, the medium was collected. The concentration of fusion protein in the supernatant from such a transfection, as well as in different volumes of supernatant following absorption on 100 µl gel slurry of anti-mouse IgG agarose beads (corresponding to 50 µl packed beads) was determined by an ELISA calibrated with purified mouse IgG Fc fragments (FIG. 2). The concentration of PSGL1/mIgG$_{2b}$ in the supernatants ranged from 150 to 200 ng/µl, and in this particular experiment it was approximately 160 ng/µl (FIG. 2A, the non-absorbed column). The concentration of PSGL1/mIgG$_{2b}$ remaining in 2, 4 and 8 ml of supernatant following absorption on 50 µl packed anti-mouse IgG agarose beads was 32, 89 and 117 ng/µl, respectively. This corresponds to 260, 290 and 360 ng of PSGL1/mIgG$_{2b}$ being absorbed onto 50 µl packed anti-mouse IgG agarose beads from 2, 4 and 8 ml of supernatant, respectively. Western blot analysis with the *B. simplicifolia* IB4 lectin revealed that 50 µl of packed beads could absorb out the PSGL1/mIgG$_{2b}$ fusion protein from 1 ml supernatant to below detectability and from 2 ml to barely detectable levels (not shown).

Figure 3:
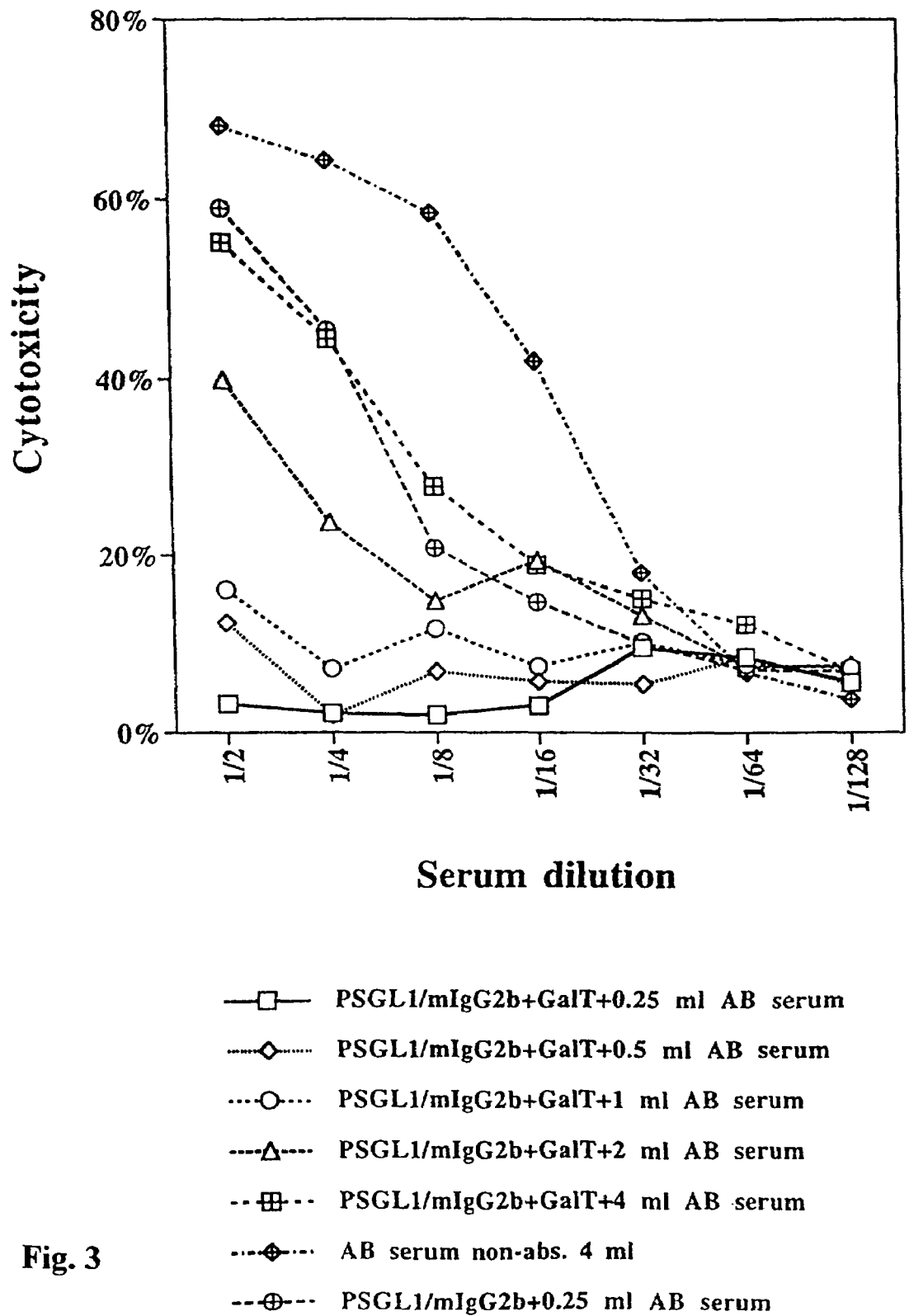

The absorption capacity of immobilized, Galα1,3Gal-substitute-d PSGL1/mIgG$_{2b}$. Twenty ml of supernatant from COS cells transfected with the PSGL1/mIgG$_{2b}$ plasmid alone or together with the porcine α1,3GT cDNA, were mixed with 500 µl gel slurry of anti-mouse IgG agarose beads each. Following extensive washing the beads were aliquoted such that 100 µl of gel slurry (50 µl packed beads) were mixed with 0.25, 0.5, 1.0, 2.0 and 4.0 ml of pooled, complement-depleted, human AB serum, and rolled head over tail at 4° C. for 4 hrs. Following absorption on PSGL1/mIgG$_{2b}$ and Galα1, 3Gal-substituted PSGL1/mIgG$_{2b}$, the serum was assayed for porcine endothelial cell cytotoxicity in the presence of rabbit complement using a 4 hr $^{51}$Cr release assay (FIG. 3). As shown in FIG. 3, 100 µl of beads carrying approximately 300 ng of PSGL1/mIgG$_{2b}$ (see above) can reduce the cytotoxicity of 4 and 2 ml AB serum in each dilution step, and completely absorb the cytotoxicity present in 1 ml and less of human AB serum. Note that the same amount of non-Galα1,3Gal-substituted PSGL1/mIgG$_{2b}$ reduces the cytotoxicity of 0.25 ml absorbed human AB serum only slightly (FIG. 3)

The Effect of Galα1,3Gal-Substituted PSGL1/mIgG$_{2b}$ on Complement-Dependent Porcine Endothelial Cell Cytotoxicity and Binding.

Figure 4:
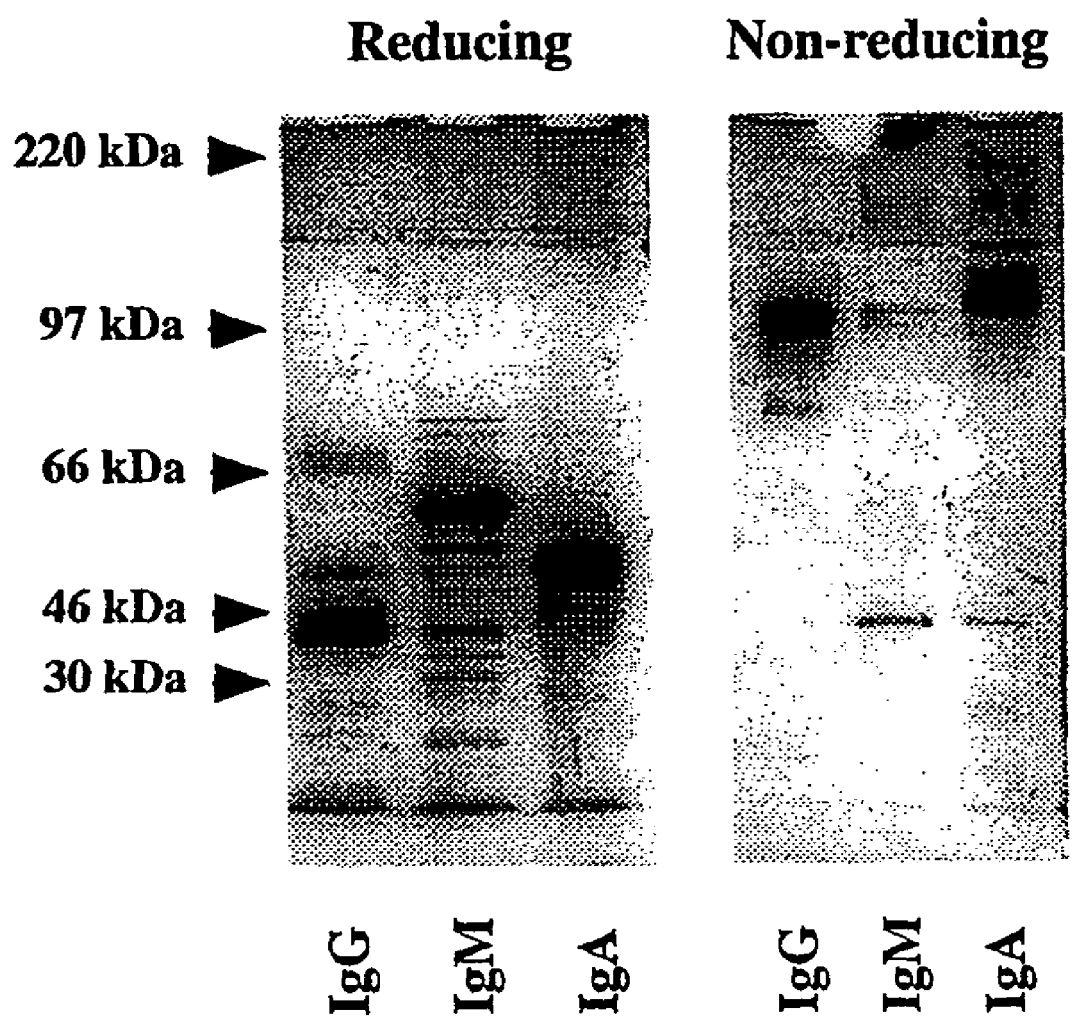
FIG. 4. is a photograph of a SDS-PAGE gelof immunoaffinity purified human IgG, IgM, and IgA. Four micrograms of each sample were run under reducing and non-reducing conditions, and proteins were visualized by silver staining.
Figure 5:
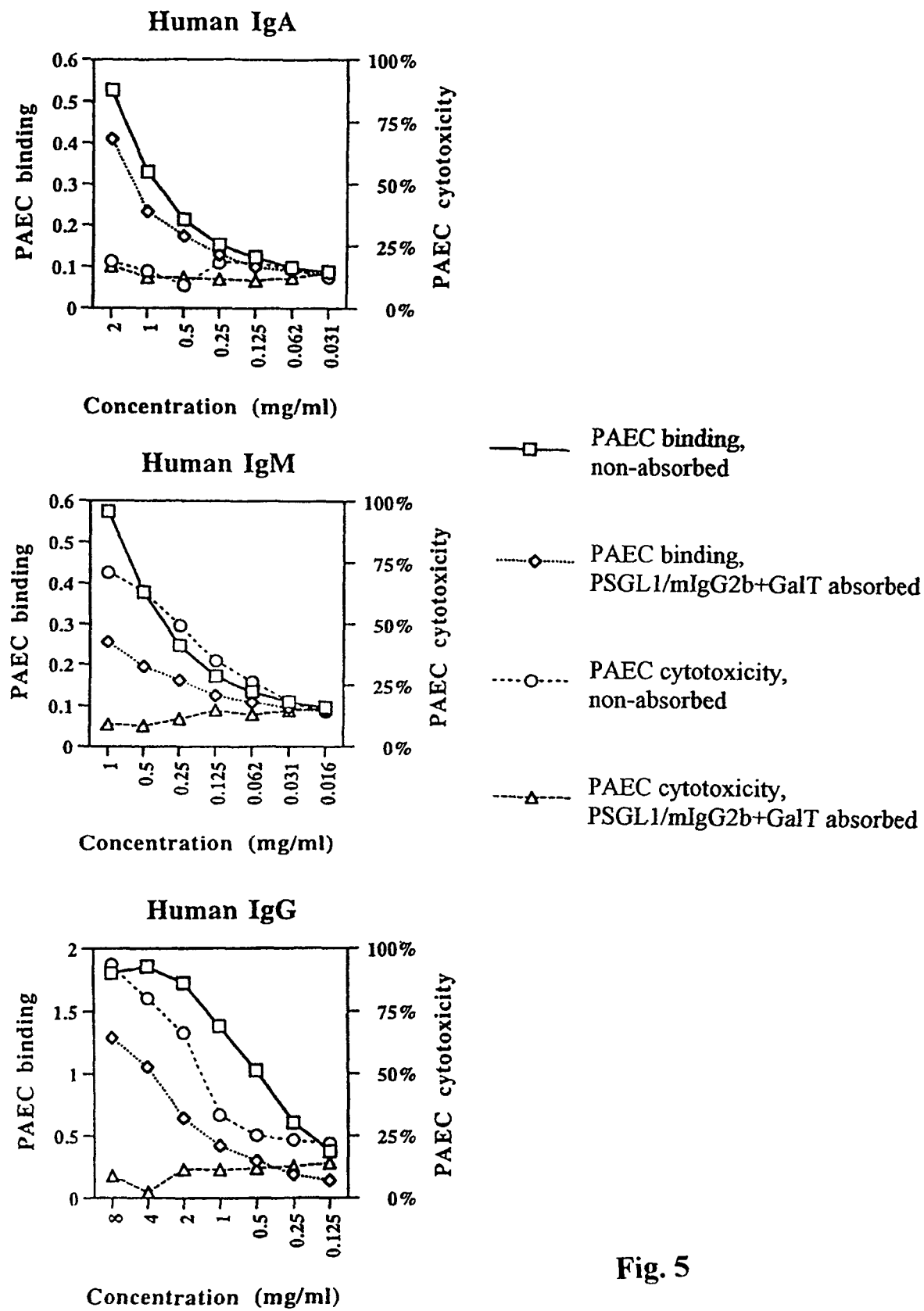
FIG. 5. are line graphs showing he antibody-dependent, complement-mediated PEC-A cell cytotoxicity of immunoaffinity purified human IgG, IgM and IgA before and after absorption on Galα1,3Gal-substituted PSGL1/mIgG$_{2b}$ was investigated by $^{51}$Cr-release assays (right handside Y-axis; % killing).

To investigate the efficiency with which PSGL1/mIgG$_{2b}$ could absorb individual human immunoglobulin classes, human IgG, IgM and IgA were purified from human AB serum by immuno-affinity chromatography on anti-human IgG, IgM and IgA agarose beads. Following its isolation IgA was passed through anti-IgG and IgM columns to remove traces of IgG and IgM. This procedure was performed for the other Ig classes as well. Ig fraction purity was checked by SDS-PAGE (FIG. 4). In concentrations found in normal serum, human IgG and IgM, but not IgA, were cytotoxic for PEC-A in the presence of rabbit complement (FIG. 5). The cytotoxicity residing in the IgG and IgM fractions was completely removed by absorption on Galα1,3Gal-substituted PSGL1/mIgG$_{2b}$. To investigate whether the lack of cytotoxicity exhibited by the IgA fraction was due to a lack of binding of human IgA antibodies to PEC-A, a cell ELISA was run with the same Ig fractions that was used in the cytotoxicity assay in order to detect bound IgG, IgM and IgA. Alkaline phosphatase-conjugated, class specific F(ab)'.sub.2 fragments were used as secondary antibodies. Eventhough the cytotoxicity of IgG and IgM was completely removed by absorption on Galα1,3Gal-substituted PSGL1/mIgG$_{2b}$, the binding was never reduced with more than 70% (ranging from 30 to 70%) for IgG, and never with more than 55% (ranging from 10 to 55%) for IgM (FIG. 5). Human IgA clearly bound to PEC-A, and the binding was only slightly reduced (not more than 29%) following absorption on Galα1, 3Gal-substituted PSGL1/mIgG$_{2b}$. The lack of cytototoxicity of the IgA fraction could therefore not be explained by an inability of the IgA fraction to bind PEC-A, but may be due to an inability to activate complement.

The Effect of Galα1,3Gal-Substituted PSGL1/mIgG$_{2b}$ on ADCC of Porcine Endothelial Cells.

Figure 6:
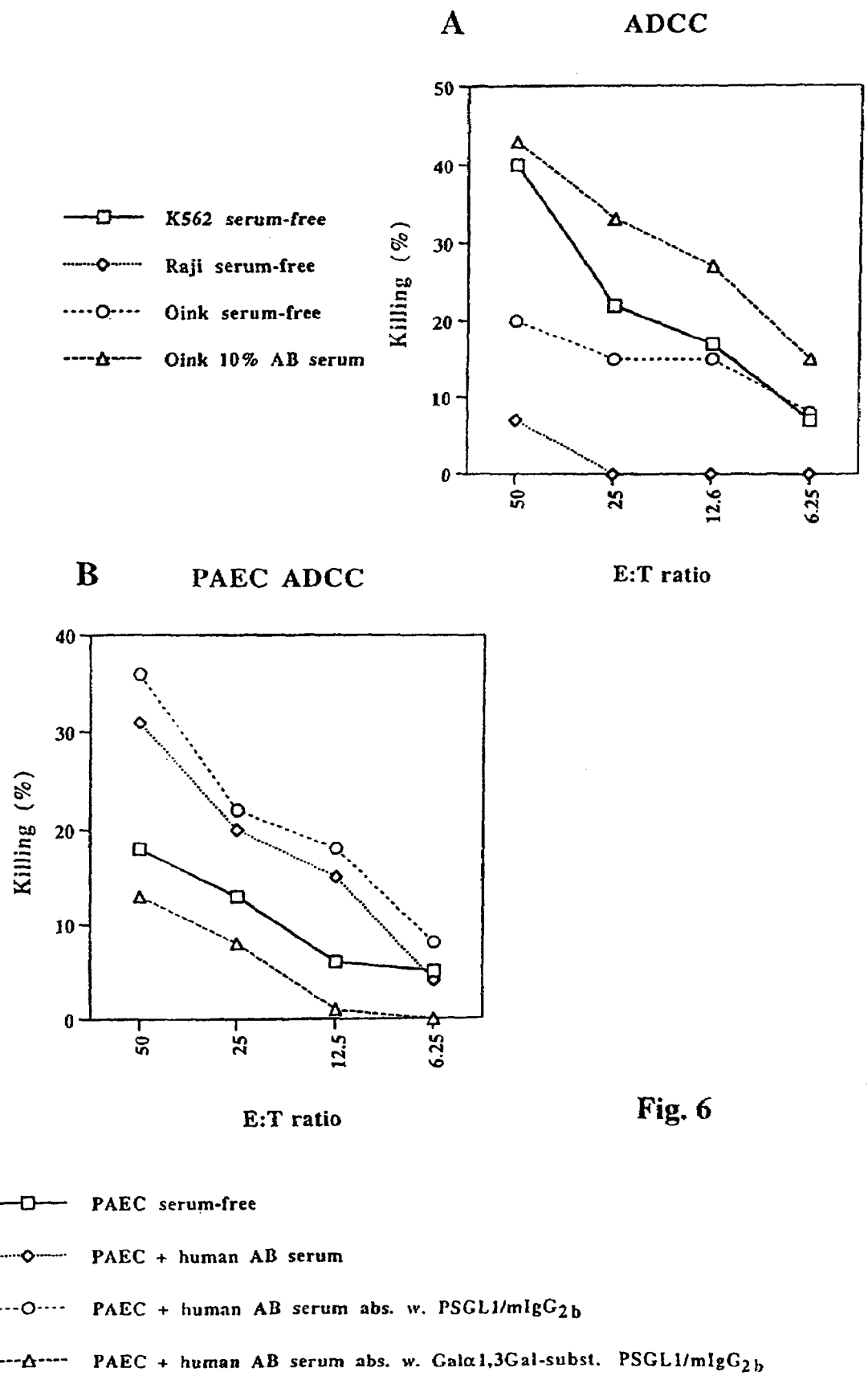
FIG. 6. are line graphs showing the direct cytotoxic effect (serum-free conditions) of human PBMC on K562, Raji and PEC-A cells, and the potentiating effect on killing by the addition of heat-inactivated, human AB serum, was investigated in a 4 hr $^{51}$Cr-release assay (graph A). The effect of heat-inactivated, human AB serum on antibody-dependent cellular cytotoxicity of PEC-A cells was studied in a 4 hr $^{51}$Cr-release assay before and after absorption on Galα1, 3Gal- and non-substituted PSGL1/mIgG$^2_{2b}$, respectively (graph B).

Several assays have been performed under serum-free conditions where PEC-A have had an intermediate sensitivity to direct killing by freshly isolated PBMC when compared to K562 and Raji cells; K562 being sensitive and Raji non-sensitive to killing by human NK cells (FIG. 6 A). In the presence of 10% human, complement-inactivated AB serum, the killing rate was almost doubled supporting an ADCC effect in vitro (FIG. 6B) in agreement with previously published data (30). However, if the serum is absorbed with the Galα1,3Gal-substituted PSGL1/mIgG$_{2b}$ under conditions known to remove all PEC-A cytotoxic antibodies (se above), the killing rate decreases to levels slightly lower than those seen under serum-free conditions. On the other hand, the PSGL1/mIgG$_{2b}$ fusion protein itself without Galα1,3Gal epitopes could not absorb out what caused the increased killing rate in the presence of human AB serum (FIG. 6B). These data support the notion that anti-pig antibodies with Galα1,3Gal specificity can support an antibody-dependent cell-mediated cytotoxicity in vitro, and that the Galα1,3Gal-substituted PSGL1/mIgG$_{2b}$ fusion protein can effectively remove these antibodies just as it effectively removes the complement-fixing cytotoxic anti-pig antibodies.

REFERENCES

1. Dorling A, Lechler R I. Prospects for xenografting. Curr. Opin. Immunol. 1994; 6 (5): 765-9.

2. Ye Y, Niekrasz M, Kosanke S, et al. The pig as a potential organ donor for man. A study of potentially transferable disease from donor pig to recipient man. Transplantation 1994; 57 (5): 694-703.

3. Michaels M G, Simmons R L. Xenotransplant-associated zoonoses. Strategies for prevention. Transplantation 1994; 57 (1): 1-7.

4. Calne R Y. Organ transplantation between widely disparate species. Transplant. Proc. 1970; 2 (4): 550-6.

5. Bach F H, Robson S C, Ferran C, et al. Endothelial cell activation and thromboregulation during xenograft rejection. Immunol. Rev. 1994; 141: 5-30.

6. Magee J C, Platt J L. Xenograft rejection—molecular mechanisms and therapeutic implications. Therap. Immunol. 1994; 1 (1): 45-58.

7. Platt J L, Lindman B J, Chen H, Spitalnik S L, Bach F H. Endothelial cell antigens recognized by xenoreactive human natural antibodies. Transplantation 1990; 50 (5): 817-22.

8. Good A H, Cooper D K, Malcolm A J, et al. Identification of carbohydrate structures that bind human antiporcine antibodies: implications for discordant xenografting in humans. Transplant. Proc. 1992; 24 (2): 559-62.

9. Holgersson J, Cairns T D, Karlsson E C, et al. Carbohydrate specificity of human immunoglobulin-M antibodies with pig lymphocytotoxic activity. Transplant. Proc. 1992; 24 (2): 605-8.

10. Oriol R, Ye Y, Koren E, Cooper D K. Carbohydrate antigens of pig tissues reacting with human natural antibodies as potential targets for hyperacute vascular rejection in pig-to-man organ xenotransplantation. Transplantation 1993; 56 (6): 1433-42.

11. Galili U. Interaction of the natural anti-Gal antibody with alpha-galactosyl epitopes: a major obstacle for xenotransplantation in humans. Immunol. Today 1993; 14 (10): 480-2.

12. Sandrin M S, Vaughan H A, Dabkowski P L, McKenzie I F. Anti-pig IgM antibodies in human serum react predominantly with Gal(alpha 1-3)Gal epitopes. Proc. Natl. Acad. Sci. USA 1993; 90 (23): 11391-5.

13. Cairns T D, Taube D H, Stevens N, Binns R, Welsh K I. Xenografts—future prospects for clinical transplantation. Immunol. Lett. 1991; 29 (1-2): 167-70.

14. Rydberg L, Hallberg E, Björck S, et al. Studies on the removal of anti-pig xenoantibodies in the human by plasmapheresis/immunoadsorption. Xenotransplantation 1995; 2: 253-263.

15. Soares M P, Latinne D, Elsen M, Figueroa J, Bach F H, Bazin H. In vivo depletion of xenoreactive natural antibodies with an anti-mu monoclonal antibody. Transplantation 1993; 56 (6): 1427-33.

16. Soares M, Lu X, Havaux X, et al. In vivo IgM depletion by anti-mu monoclonal antibody therapy. The role of IgM in hyperacute vascular rejection of discordant xenografts. Transplantation 1994; 57 (7): 1003-9.

17. Leventhal J R, John R, Fryer J P, et al. Removal of baboon and human antiporcine IgG and IgM natural antibodies by immunoadsorption. Results of in vitro and in vivo studies. Transplantation 1995; 59 (2): 294-300.

18. Geller R L, Bach F H, Turman M A, Casali P, Platt J L. Evidence that polyreactive antibodies are deposited in rejected discordant xenografts. Transplantation 1993; 55 (1): 168-72.

19. Koren E, Milotic F, Neethling F A, et al. Murine monoclonal anti-idiotypic antibodies directed against human anti-alpha Gal antibodies prevent rejection of pig cells in culture: implications for pig-to-human organ xenotransplantation. Transplant. Proc. 1996; 28 (2): 559.

20. Leventhal J R, Sakiyalak P, Witson J, et al. The synergistic effect of combined antibody and complement depletion on discordant cardiac xenograft survival in nonhuman primates. Transplantation 1994; 57: 974-978.

21. Pruitt S K, Kirk A D, Bollinger R R, et al. The effect of soluble complement receptor type 1 on hyperacute rejection of porcine xenografts. Transplantation 1994; 57 (3): 363-70.

22. Neethling F A, Koren E, Oriol R, et al. Immunoadsorption of natural antibodies from human serum by affinity chromatography using specific carbohydrates protects pig cells from cytotoxic destruction. Transplant. Proc. 1994; 26 (3): 1378.

23. Neethling F A, Koren E, Ye Y, et al. Protection of pig kidney (PK 15) cells from the cytotoxic effect of anti-pig antibodies by alpha-galactosyl oligosaccharides. Transplantation 1994; 57 (6): 959-63.

24. Li S, Yeh J-C, Cooper D KC, Cummings R D. Inhibition of human anti-(xGal IgG by oligosaccharides derived from porcine stomach mucin. Xenotransplantation 1995; 2: 279-288.

25. Cooper D K, Good A H, Ye Y, et al. Specific intravenous carbohydrate therapy: a new approach to the inhibition of antibody-mediated rejection following ABO-incompatible allografting and discordant xenografting. Transplant. Proc. 1993; 25 (1 Pt 1): 377-8.

26. Sandrin M S, Fodor W L, Moulitouris E, et al. Enzymatic remodelling of the carbohydrate surface of a xenogenic cell substantially reduces human antibody binding and complement-mediated cytolysis. Nature Med. 1995; 1 (12): 1261-7.

27. Sharma A, Okabe J, Birch P, et al. Reduction in the level of Gal(alpha1,3)Gal in transgenic mice and pigs by the expression of an alp-ha(1,2) fucosyltransferase. Proc. Natl. Acad. Sci. USA 1996; 93 (14): 7190-5.

28. Koike C, Kannagi R, Takuma Y, et al. Introduction of (x(1,2)-fucosyltransferase and its effect on $\alpha$-Gal epitopes in transgenic pig. Xenotransplantation 1996; 3: 81-86.

29. Blakely M L, Van der Werf W J, Berndt M C, Dalmasso A P, Bach F H, Hancock W W. Activation of intragraft endothelial and mononuclear cells during discordant xenograft rejection. Transplantation 1994; 58 (10): 1059-66.

30. Seebach J D, Yamada K, McMorrow I M, Sachs D H, DerSimonian H D. Xenogeneic human anti-pig cytotoxicity mediated by activated natural killer cells. Xenotransplantation 1996; 3: 188-197.

31. Chou D K, Dodd J, Jessell T M, Costello C E, Jungalwala F B. Identification of alpha-galactose (alpha-fucose)-asialo-GM I glycolipid expressed by subsets of rat dorsal root ganglion neurons. J. Biol. Chem. 1989; 264 (6): 3409-15.

32. Fujiwara S, Shinkai H, Deutzmann R, Paulsson M, Timpi R. Structure and distribution of N-linked oligosaccharide chains on various domains of mouse tumour laminin. Biochem. J. 1988; 252 (2): 453-61.

33. Dasgupta S, Hogan E L, Glushka J, van Halbeek H. Branched monosialo gangliosides of the lacto-series isolated from bovine erythrocytes: characterization of a novel ganglioside, NeuGc-isooctaosylceramide. Arch. Biochem. Biophys. 1994; 310 (2): 373-84.

34. Wong C H. Enzymatic and Chemo-Enzymatic Synthesis Of Carbohydrates. Pure Appl. Chem. 1995; 67 (10): 1609-1616.30

35. Seed B. An LFA-3 cDNA encodes a phospholipid-linked membrane protein homologous to its receptor CD2. Nature 1987; 329 (6142): 840-2.

36. Khodadoust M M, Candal F J, Maher S E, et al. PEC-A: An immortalized porcine aortic endothelial cell. Xenotransplantation 1995; 2: 79-87.

37. Dabkowski P L, Vaughan H A, McKenzie IF, Sandrin M S. Characterisation of a cDNA clone encoding the pig alpha 1,3 galactosyltransferase: implications for xenotransplantation. Transplant. Proc. 1993; 25 (5): 2921.

38. Dabkowski P L, Vaughan H A, McKenzie IF, Sandrin M S. Isolation of a cDNA clone encoding the pig alpha 1,3 galactosyltransferase. Transplant. Proc. 1994; 26 (3): 1335.

39. Gustafsson K, Strahan K, Preece A. Alpha 1,3galactosyltransferase: a target for in vivo genetic manipulation in xenotransplantation. Immunol. Rev. 1994; 141: 59-70.

40. Sako D, Chang X J, Barone K M, et al. Expression cloning of a functional glycoprotein ligand for P-selectin. Cell 1993; 75 (6): 1179-86.

41. Laemmli U K. Cleavage of structural proteins during the assembly of the head of bacteriophage T4. Nature 1970; 227 (259): 680-5.

42. Towbin H, Staehelin T, Gordon J. Electrophoretic transfer of proteins from polyacrylamide gels to nitrocellulose sheets: procedure and some applications. Proc. Natl. Acad. Sci. USA 1979; 76 (9): 4350-4

43. Carraway K L, Hull S R. Cell surface mucin-type glycoproteins and mucin-like domains. Glycobiology 1991; 1 (2): 131-8.

44. Shimizu Y, Shaw S. Mucins in the mainstream. Nature 1993; 366: 630-631.

45. Galili U, Macher B A, Buehler J, Shohet S B. Human natural anti-a-galactosyl IgG. II. The specific recognition of a(1-3)-linked galactose residues. J. Exp. Med. 1985; 162: 573-582.

46. Platt J L, Fischel R J, Matas A J, Reif S A, Bolman R M, Bach F H. Immunopathology of hyperacute xenograft rejection in a swine-to-primate model. Transplantation 1991; 52 (2): 214-20.

47. Cooper D K, Ye Y, Niekrasz M, et al. Specific intravenous carbohydrate therapy. A new concept in inhibiting antibody-mediated rejection—experience with ABO-incompatible cardiac allografting in the baboon. Transplantation 1993; 56 (4): 769-77. 48. Romano E L, Soyano A, Linares J. Preliminary human study of synthetic trisaccharide representing blood substance A. Transplant. Proc. 1987; 19 (6): 4475-8.

49. Ye Y, Neethling F A, Niekrasz M, et al. Evidence that intravenously administered alpha-galactosyl carbohydrates reduce baboon serum cytotoxicity to pig kidney cells (PK 15) and transplanted pig hearts. Transplantation 1994; 58 (3): 330-7.

50. Vaughan H A, Oldenburg K R, Gallop M A, Atkin J D, McKenzie IFC, Sandrin M S. Recognition of an octapeptide sequence by multiple Gala(1,3)Galbinding proteins. Xenotransplantation 1996; 3: 18-23.

51. Kooyman D L, McClellan S B, Parker W, et al. Identification and characterization of a galactosyl peptide mimetic. Implications for use in removing xenoreactive anti-a Gal antibodies. Transplantation 1996; 61 (6): 851-5.

52. Koren E, Milotic F, Neethling F A, et al. Monoclonal antiidiotypic antibodies neutralize cytotoxic effects of anti-(xGal antibodies. Transplantation 1996; 62: 837-843. 53. Fodor W L, Williams B L, Matis L A, et al. Expression of a functional human complement inhibitor in a transgenic pig as a model for the prevention of xenogeneic hyperacute organ rejection. Proc. Natl. Acad. Sci. USA 1994; 91 (23): 11153-7.

54. Rosengard A M, Cary N R, Langford G A, Tucker A W, Wallwork J, White D J. Tissue expression of human complement inhibitor, decay-accelerating factor, in transgenic pigs. A potential approach for preventing xenograft rejection. Transplantation 1995; 59 (9): 1325-33.

55. Diamond L E, McCurry K R, Martin M J, et al. Characterization of transgenic pigs expressing functionally active human CD59 on cardiac endothelium. Transplantation 1996; 61 (8): 1241-9.

56. Kroshus T J, Bolman R M, 111, Dalmasso A P, et al. Expression of human CD59 in transgenic pig organs enhances organ survival in an ex vivo xenogeneic perfusion model. Transplantation 1996; 61 (10): 1513-21.

57. Pascher A, Poehlein C H, Storck M, et al. Human decay accelerating factor expressed on endothelial cells of transgenic pigs affects complement activation in an ex vivo liver perfusion model. Transplant. Proc. 1996; 28 (2): 754-5.

58. Tolan M J, Friend P J, Cozzi E, et al. Life-supporting transgenic kidney transplants in a pig-to-primate model. XVI International congress of the transplantation society. Barcelona, 1996: 102.

59. Schmoeckel M, Nollert G, Shahmohammadi M, et al. Prevention of hyperacute rejection by human decay accelerating factor in xenogeneic perfused working hearts. Transplantation 1996; 62 (6): 729-734.

60. Rosen S D, Bertozzi C R. Leukocyte adhesion: Two selectins converge on sulphate. Curr. Biol. 1996; 6 (3): 261-264.

61. Asa D, Raycroft L, Ma L, et al. The P-Selectin Glycoprotein Ligand Functions As a Common Human Leukocyte Ligand For P— and E-Selectins. J. Biol. Chem. 1995; 270 (19): 11662-11670.

62. Schaapherder A F, Gooszen H G, te Bulte M T, Daha M R. Human complement activation via the alternative pathway on porcine endothelium initiated by IgA antibodies. Transplantation 1995; 60 (3): 287-91.

63. Gauldi J, Richards C, Lamontagne L. Fc receptors for IgA and other immunoglobulins on resident and activated alveolar macrophages. Mol. Immunol. 1983; 20: 1029-1037.

64. Monteiro R C, Kubagawa H, Cooper M. Cellular distribution, regulation, and biochemical nature of an Fcα receptor in humans. J. Exp. Med. 1990; 171: 597-613.

EXAMPLE 2

Stable Expression of Substituted Recominant P-Selectin Glycoprotein Ligand/Immunoglobulin Fusion Proteins General Methods Cell Culture CHO-K1, COS7 m6, 293T and the porcine aortic endothelial cell line, PEC-A (Khodadoust, M. M. et al., 1995) were cultured in Dulbecco's modified Eagle's medium (DMEM) with 10% fetal bovine serum (FBS) and 25 µg/ml gentamicin sulfate. The selection media contained puromycin (cat. no. P7255; Sigma, St. Louis, Mo. 63178), hygromycin (cat. no. 400051; Calbiochem, La Jolla, Calif. 92039), and G418 (cat. no. G7034; Sigma, St. Louis, Mo. 63178) as indicated below.

Construction of Expression Plasmids

The porcine α1,3GalT (Gustafsson, K. et al., 1994) and PSGL-1/mIgG$_{2b}$ expression plasmids were constructed as described (Liu, J. et al., 1997). The C2 GnT1 cDNA was amplified by PCR from an HL60 cDNA library using cgcgggctcgagatgaagatattcaaatgt and cgcggggcggccgctcatgatgtggtagtgagat as forward and reverse primers, respectively. The vectors used to generate stable transfectants were bidirectional having the EF1α promoter upstream of a polylinker, a splice donor and acceptor site, and the bidirectional poly(A) addition signal of SV40; opposite in orientation to this transcription unit, and utilizing the poly(A) signals from the opposite direction was a second transcription unit consisting of the HSV TK promoter followed by the coding sequences for puromycin acetyltransferase (EF1α/PAC), the hygromycin b (EF1α/Hyg), and the neomycin (EF1α/Neo) resistance genes (N. Chiu, J. Holgersson and B. Seed). The cDNAs of porcine α1,3GalT and PSGL-1/mIgG$_{2b}$ were swapped into the EF1α/Hyg and EF1α/PAC vectors, respectively, using Hind III and Not I. The gene of C2GnT1 was swapped into EF1α/Neo using Xho I and Not I.

DNA Transfection and Clonal Selection

Adherent CHO-K1, COS7 m6 and 293T cells were seeded in 75 cm$^2$ T-flasks and were transfected approximately 24 hours later at a cell confluency of 70-80%. A modified polyethylenimine (PEI) transfection method was used for transfection (Boussif, O. et al., 1995; He, Z. et al., 2001). Twenty-four hours after transfection, cells in each T-flask were split into five 100 mm petri dishes and incubated in selection medium. The concentration of puromycin in the selection medium was 6.0, 1.5, and 1.0 µg/ml respectively, for CHO-K1, COS7 m6 and 293T cells. A hygromycin b concentration of 550, 50, and 100 pg/ml was used for CHO-K1, COS7 m6 and 293T cells, respectively, and a G418 concentration of 900 µg/ml was used for CHO-K1 cells. The selection medium was changed every third day. The drug resistant clones formed after approximately two weeks. Clones were identified under the microscope and hand-picked using a pipetman. Selected colonies were cultured in 96-well plates in the presence of selection drugs for another two weeks. Cell culture supernatants were harvested when the cells had reached 80-90% confluency, and the concentration of PSGL-1/mIgG$_{2b}$ was assessed by ELISA, SDS-PAGE and Western blotting using a goat anti-mouse IgG Fc antibody. The CHO-K1, COS7 m6 and 293T clones with the highest PSGL-1/mIgG$_{2b}$ expression were transfected with the porcine α1,3GalT encoding plasmid and selected in hygromycin-containing medium. Resistant clones were isolated and characterized by ELISA, SDS-PAGE and Western blot using both a goat anti-mouse IgG Fc antibody and the GSA I IB$_4$-lectin recognizing terminal α-Gal. Two CHO clones with a high relative α-Gal expression on PSGL-1/mIgG$_{2b}$ were further transfected with the C2 GnT1 and selected in G418-containing medium. Expression of C2 GnT1 was verified by an increase in size of PSGL-1/mIgG$_{2b}$ indicating more complex O-glycans.

SDS-PAGE and Western Blotting

SDS-PAGE was run by the method of Laemmli (Laemmli, U. K., 1970) with 5% stacking gels and 8% resolving gels using a vertical Mini-Protean II electrophoresis system (Bio-Rad, Hercules, Calif., USA). Samples were electrophoretically run under reducing and non-reducing conditions. In order to increase the resolution, 4-15% gradient gels (cat.no. 161-1104; Bio-Rad, Hercules, Calif., USA), or 4-12% gradient gels (cat.no NP0322; Invitrogen, Lidingö, Sweden) were used in some experiments. The latter gels were used in combination with the MES buffer (cat.noNP0002; Invitrogen). A precision protein standard (cat.no RPN756; Amersham Biosciences, Uppsala, Sweden) was applied as a reference for protein molecular weight determination. Protein gels were stained using the Pro Q Emerald 300 Glycoprotein detection kit in combination with Ruby (cat.no P21855; Molecular Probes, Leiden, The Netherlands). These gels were visualized in a Flour-S Max Multimager carrying a CCD camera. Separated proteins were also electrophoretically blotted onto Hybond C extra membranes (cat.no. RPN203E; Amersham Biosciences), or nitrocellulose membranes (cat.no LC2001; Invitrogen) using a Mini TransBlot (Bio-Rad) electrophoretic transfer cell (Towbin, H. et al., 1979). Following blocking for 1 hour in 3% BSA in PBS with 0.2% Tween 20, the membranes were probed for one hour at room temperature with peroxidase-conjugated GSA I IB$_4$-lectin (cat.no. L-5391; Sigma) diluted to a concentration of 1 μg/ml, peroxidase-conjugated goat anti-mouse IgG Fc antibodies (cat.no. A-9917; Sigma) diluted 1:1,000, and a mouse anti-PSGL-1 antibody (clone KPL-1, cat.no 557502; BD PharMingen, San Diego, Calif.) diluted 1:1,000. Secondary antibody was a peroxidase-conjugated goat anti-mouse IgG F(ab)'$_2$ (cat.no A 2304; Sigma) diluted 1:50,000. All dilutions were done in blocking buffer. The membranes were washed three times with PBS containing 0.2% Tween 20 between and after incubations. Bound lectins and antibodies were visualized by chemiluminescence using the ECL kit according to the manufacturer's instructions (cat.no. RPN 2106; Amersham Biosciences).

α-Gal Epitope Density on, and Quantification of, PSGL-1/mIgG$_{2b}$ Using an Enzyme-Linked Immunosorbent Assay The concentration of recombinant PSGL-1/mIgG$_{2b}$ in cell culture supernatants, and its relative α-Gal epitope density, was determined by a two-antibody sandwich ELISA. The 96-well ELISA plate was coated overnight at 4° C. with an affinity-purified, polyclonal goat anti-mouse IgG Fc antibody (cat. nr. 55482; Cappel/Organon Teknika, Durham, N.C.) at a concentration of 20 μg/ml. The plate was blocked with 1% BSA in PBS for 1 hour. The supernatant containing PSGL-1/mIgG$_{2b}$ was incubated for 4 hours and then washed three times with PBS containing 0.5% (v/v) Tween 20. After washing, the plate was incubated with a peroxidase-conjugated, anti-mouse IgG Fc antibody (cat.no. A-9917; Sigma) in a 1:3,000 dilution or with peroxidase-conjugated GSA I IB$_4$-lectin (cat.no. L-5391;Sigma) diluted 1:2,000, for two hours. Bound peroxidase-conjugated antibody or peroxidase-conjugated GSA-lectin was visualized with 3,3',5,5'-Tetramethylbenzidine dihydrochloride (cat. nr. T-3405; Sigma, Sweden). The reaction was stopped by 2M H$_2$SO$_4$ and the plates read at 450 nm. The PSGL-1/mIgG$_{2b}$ concentration was estimated using for calibration a dilution series of purified mouse IgG Fc fragments (cat. Nr. 015-000-008; Jackson ImmunoResearch Labs., Inc., West Grove, Pa.) resuspended in the medium used for fusion protein production or in PBS containing 1% BSA. The α-Gal epitope density was determined by comparing the relative O.D. from the two ELISAs (GSA-reactivity/anti-mouse IgG reactivity).

Porcine Aortic Endothelial Cell Cytotoxicity Assay

The porcine aortic endothelial cell (PAEC) cytotoxicity assay was performed as described (Liu, J. et al., 2003). The amount of PSGL-1/mIgG$_{2b}$ needed from each cell clone to reduce cell cytotoxicity to 40% of maximum (y=0.4) was deduced from the formula describing the curve obtained after linear regression of the measured values for each fusion protein, and thereafter calculating the corresponding x-value (microgram adsorber).

Stirred Flask Batch Cultures of CHO Clones

Each batch culture was started with $6.0 \times 10^7$ cells (representing ten 175 cm$^2$ T-flasks with cells of 90-100% confluency). After digestion with trypsin (0.5 mg/ml)-EDTA (0.2 mg/ml), cells were resuspended in a small volume of medium and centrifuged at 200×g for 5 minutes to remove excess of trypsin. The cell density was determined by counting the cells in a Burker chamber, and medium was added to a final concentration of $3.0 \times 10^5$ cells/ml. The cell suspension was transferred to 1L stirred flasks and a cell spin device (Integra Biosciences, Wallisellen, Switzerland) was utilized in order to stir the cultures at a speed of 60 rpm. PSGL-1/mIgG$_{2b}$ secreting CHO-K1 cells expressing α1,3GalT alone or in combination with C2 GnT1, were cultured in the presence of puromycin (200 μg/ml), or puromycin (200 μg/ml) and G418 (500 μg/ml), respectively. The cells were counted every second day. When the cell density reached $5.0 \times 10^5$ cells/ml, new medium was added so that the cell density once again equalled $3.0 \times 10^5$ cells/ml. This was repeated until the cell suspension volume reached 1,000 ml. Cells were then continuously cultured until cell viability was reduced to 50%.

Purification of Recombinant PSGL-1/mIgG$_{2b}$

The supernatants were cleared from debris by centrifugation at 1,420×g for 20 minutes. Cleared supernatants were passed through a column containing 10 ml of goat anti-mouse IgG (whole molecule)-agarose (cat.no. A 6531; Sigma) at a flow rate of 0.5 ml/min. Following washing with 120 ml of PBS, bound fusion protein was eluted with 120 ml of 3 M NaSCN. The contents of the tubes containing the fusion protein was pooled following analysis by SDS-PAGE and Western blotting using anti-mouse IgG for detection. The fraction with PSGL-1/mIgG$_{2b}$ was dialyzed against distilled water, lyophilised, and resuspended in 1-2 ml of distilled H$_2$O. The concentration of the fusion protein was determined by ELISA. To remove low molecular weight contaminants, the fusion protein was further purified by gel filtration on a HiPrep 16/60 Sephacryl S-200 HR column (cat.no. 17-1166-01; Amersham Biosciences, Uppsala, Sweden) eluted with PBS at a flow rate of 0.5 ml/min using a FPLC (Pharmacia Biotech, Sweden). Five-ml fractions were collected and tubes containing protein were identified by UV spectrophotometry at 280 nm. Pooled fractions were again analyzed by SDS-PAGE and Western blotting, pooled, dialyzed and resuspended in distilled water.

Chemical Release and Permethylation of O-Linked Glycans from Purified PSGL-1/mIgG$_{2b}$ Oligosaccharides were released by β-elimination as described (Carlstedt, I. et al., 1993). Released oligosaccharides were evaporated under a stream of nitrogen at 45° C., and permethylated according to Ciucanu and Kerek (Ciucanu, I. et al., 1984), with slight modifications as described (Hansson, G. C. et al., 1993).

Mass Spectrometry

Electrospray ionization-mass spectrometry (ESI-MS) in positive-ion mode was performed using an LCQ ion-trap mass spectrometer (ThermoFinnigan, San Jose, Calif.). The sample was dissolved in methanol:water (1:1) and introduced into the mass spectrometer at a flow rate of 5-10 μl/min. Nitrogen was used as sheath gas and the needle voltage set to 4.0 kV. The temperature of the heated capillary was set to 200° C. A total of 10-20 spectra were summed to yield the ESI-MS and ESI-MS/MS spectra.

Results

Stable Expression of α-Gal Substituted P-Selectin Glycoprotein Ligand-1/Mouse IgG$_{2b}$ in Different Host Cells Following 15-20 days of culture in selection medium supplemented with puromycin, differently sized colonies of CHO-K1, COS7 m6 and 293T cells were identified by phase contrast microscopy. Under the microscope, 192 colonies of each cell type were picked by pipette and transferred to two 96-well plates for further expansion under selection. An Ig sandwich ELISA was used to assess fusion protein concentration in the supernatants of individual clones, and 31 CHO-K1, 8 COS7 m6 and 36 293T colonies were anti-mouse IgG Fc positive. The top five secreting colonies from each cell line were moved to a 24-well plate and further expanded. The best expressing CHO-K1, COS7 m6 and 293T clones were transfected with the α1,3GalT-encoding plasmid carrying the hygromycin B resistance gene. PSGL-1/mIgG$_{2b}$ expressing cells that had stably integrated the α1,3GalT gene were selected using both puromycin and hygromycin. Twenty-seven CHO-K1, 3 COS7 m6 and 31 293T colonies were selected. Colonies to be expanded were chosen based on the concentration of fusion protein and its relative level of α-Gal epitope substitution as determined in anti-mouse IgG and Griffonia simplicifolia I IB4 lectin ELISAs. Immuno-affinity isolated PSGL-1/mIgG$_{2b}$ expressed in CHO-K1 (clone 5L4-1 and 10, respectively), COS7 m6 (clone 51 and 2H5, respectively) and 293T (clone 14 and C, respectively) cells with or without the porcine α1,3GalT was characterized by SDS-PAGE and Western blotting (Table I, FIG. 7). All cell lines produced an anti-mouse IgG Fc-reactive protein of approximately 300 kDa under non-reducing conditions (FIG. 7A). In accordance with previous observations (Liu, J. et al., 1997; Liu, J. et al., 2003), PSGL-1/mIgG$_{2b}$ was produced as a dimer as indicated by the reduction to half the size upon reduction (compare FIGS. 7A and B). The presence of α-Gal epitopes on the fusion protein made in the different cell types was detected using the GSA I IB$_4$ lectin (FIG. 7B). Co-expression of the α1,3GalT in CHO-K1 (clone 5L4-1), COS7 m6 (clone 5I) and 293T (clone 14) led to expression of α-Gal epitopes on the fusion protein as detected by the lectin. The lectin reactivity of PSGL-1/mIgG$_{2b}$ made in 293T cells without the α1,3GalT was unexpected, and indicates the presence of α-Gal residues other than the Galili antigen on that fusion protein (FIG. 7B). The fusion protein produced in COS and 293T cells in the presence of α1,3GalT contained glycoforms of bigger size than the fusion protein produced in CHO-K1 cells (FIG. 7B).

TABLE 1

CHO, COS and 293T derived cell clones

| Cell clone | PSGL-1/mIgG$_{2b}$ | α1, 3GalT | C2 GnTI |
|---|---|---|---|
| CHO-10 | X | | |
| CHO-5L4-1 | X | X | |
| CHO-C2-1-9 | X | X | X |
| COS-2H5 | X | | |
| COS-5I | X | X | |
| 293T-C | X | | |
| 293T-14 | X | X | |

The α-Gal Epitope Density on PSGL-1/mIgG$_{2b}$ is Dependent on the Host Cell Used for its Production The relative α-Gal epitope density on PSGL-1/mIgG$_{2b}$ made in CHO, COS and 293T cells was determined by ELISA (FIG. 8). PSGL-1/mIgG$_{2b}$ made in COS cells in the presence of the α1,3GalT exhibited a 5.3-fold increase in the relative O.D. (GSA-reactivity/anti-mouse IgG reactivity) compared to PSGL-1/mIgG$_{2b}$ made in COS without the α1,3GalT (FIG. 8). For 293T cells there was a 3.1-fold increase in the relative O.D., and for CHO cells there was just a 1.8-fold increase (FIG. 8). The ELISA results were in agreement with the relative GSA lectin staining seen in the Western blot experiments of immuno-affinity purified PSGL-1/mIgG$_{2b}$ (FIG. 7B).

Figure 9:
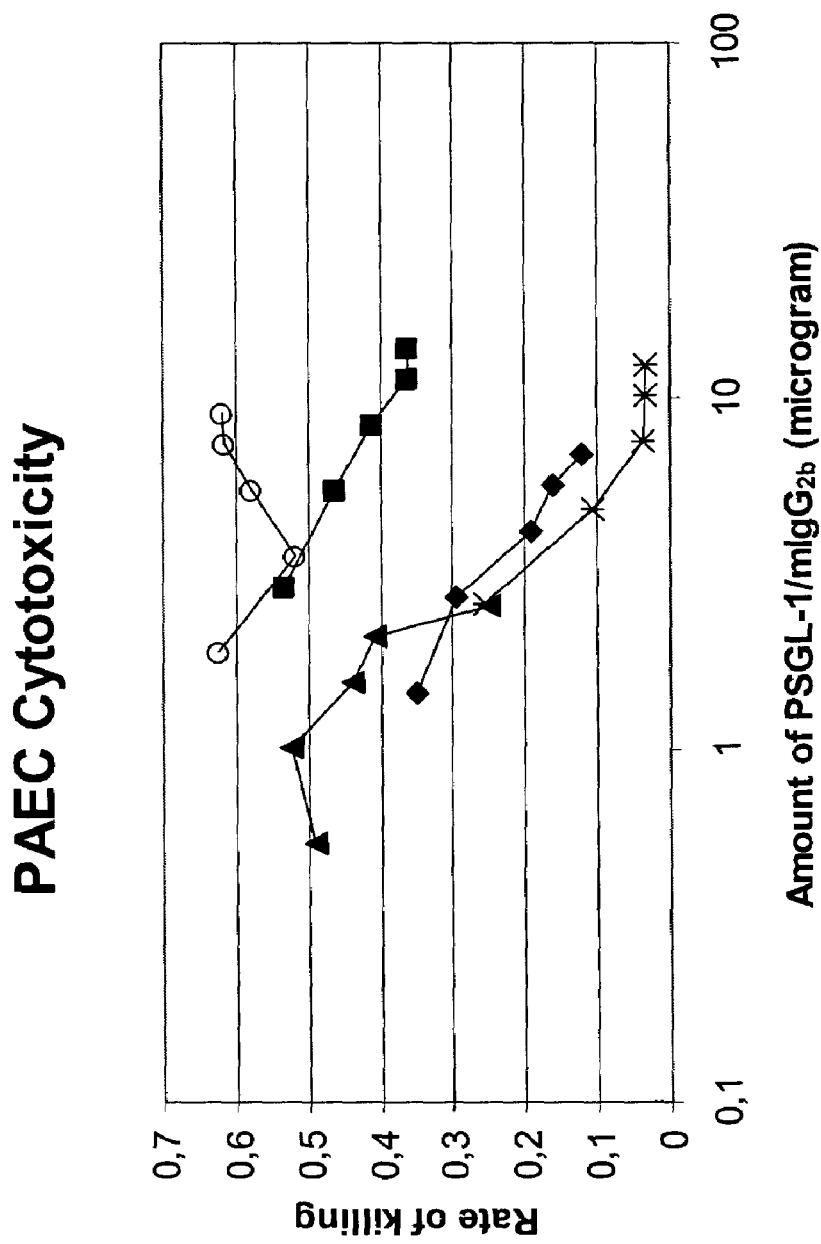
FIG. 9. is a line graph depicting Porcine aortic endothelial cell cytotoxicity of human blood group AB serum adsorbed on PSGL-1/mIgG$_{2b}$ produced in different host cells.

The Anti-Pig Antibody Adsorption Efficacy of PSGL-1/mIgG$_{2b}$ made in Different Host Cells Correlates to its Degree of α-Gal Substitution Porcine aortic endothelial cell cytotoxicity was used to evaluate the ability of PSGL-1/mIgG$_{2b}$ produced in CHO-K1 (clone 5L4-1), COS7 m6 (clone 51) and 293T (clone 14) cells co-expressing the porcine α1,3GalT to adsorb the anti-pig reactive antibodies of human blood group AB serum (FIG. 9). In order to reduce the PAEC cytotoxicity of human AB serum to 40% of maximum, 9.1 μg of CHO cell-made PSGL-1/mIgG$_{2b}$ were needed (FIG. 9). For COS and 293T cell-made PSGL-1/mIgG$_{2b}$, 16 and 4 times less, respectively, were needed to reduce the PAEC cytotoxicity to the same level. Furthermore, PSGL-1/mIgG$_{2b}$ made in CHO-K1 cells in the presence of the α1,3GalT gene could not reduce the PAEC cytotoxicity of blood group AB serum below 36%, whereas a reduction to 12 and 25% was seen with PSGL-1/mIgG$_{2b}$ made in α1,3GalT expressing COS and 293T cells, respectively, even under non-saturating conditions.

Figure 10:
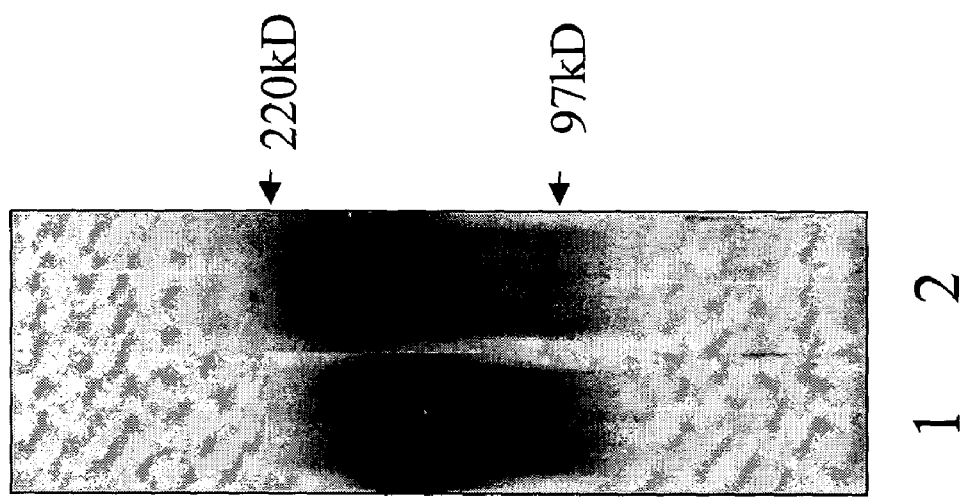
FIG. 10. is a photograph of a Western blot analysis of PSGL-1/mIgG$_{2b}$ fusion protein immunoaffinity purified from supernatants of stably transfected CHO-K1 cells.

Co-Expression of a Core 2 β1,6 GlcNAc Transferase in CHO Cells Improves PSGL-1/mIgG$_{2b}$ α-Gal Epitope Density and Anti-Pig Antibody Adsorption Efficacy In an attempt to increase the number of α-Gal epitopes on CHO-K1 cell-secreted mucin/Igs, CHO-K1 cells stably expressing PSGL-1/mIgG$_{2b}$, α1,3GalT and C2 GnT1 were established, and PSGL-1/mIgG$_{2b}$ secreted by those cells were analyzed by ELISA, SDS-PAGE and Western blot using the anti-mouse IgG antibody and GSA I IB$_4$. The apparent MW of PSGL-1/mIgG$_{2b}$ increased following stable expression of the core 2 enzyme indicating more complex glycans on the fusion protein (FIG. 10). The α-Gal epitope density on PSGL-1/mIgG$_{2b}$ showed a 13.0-fold increase compared to PSGL-1/mIgG$_{2b}$ made in CHO-K1 cells without the □1,3GalT and a 7.4-fold increase compared to PSGL-1/mIgG$_{2b}$ made with the α1,3GalT alone (FIG. 8). Furthermore, the anti-pig antibody adsorption efficacy of PSGL-1/mIgG$_{2b}$ produced in CHO-K1 cells stably expressing α1,3GalT and the C2 GnT1 (CHO-C2-1-9) was similar to the adsorption efficacy of PSGL-1/mIgG$_{2b}$ produced in 293T and COS cells co-expressing the α1,3GalT (FIG. 9), with 10 times less fusion protein needed to reduce the PAEC cytotoxicity of human AB serum to 40% of maximum compared to PSGL-1/mIgG$_{2b}$ made in the CHO clone 5L4-1.

Figure 11:
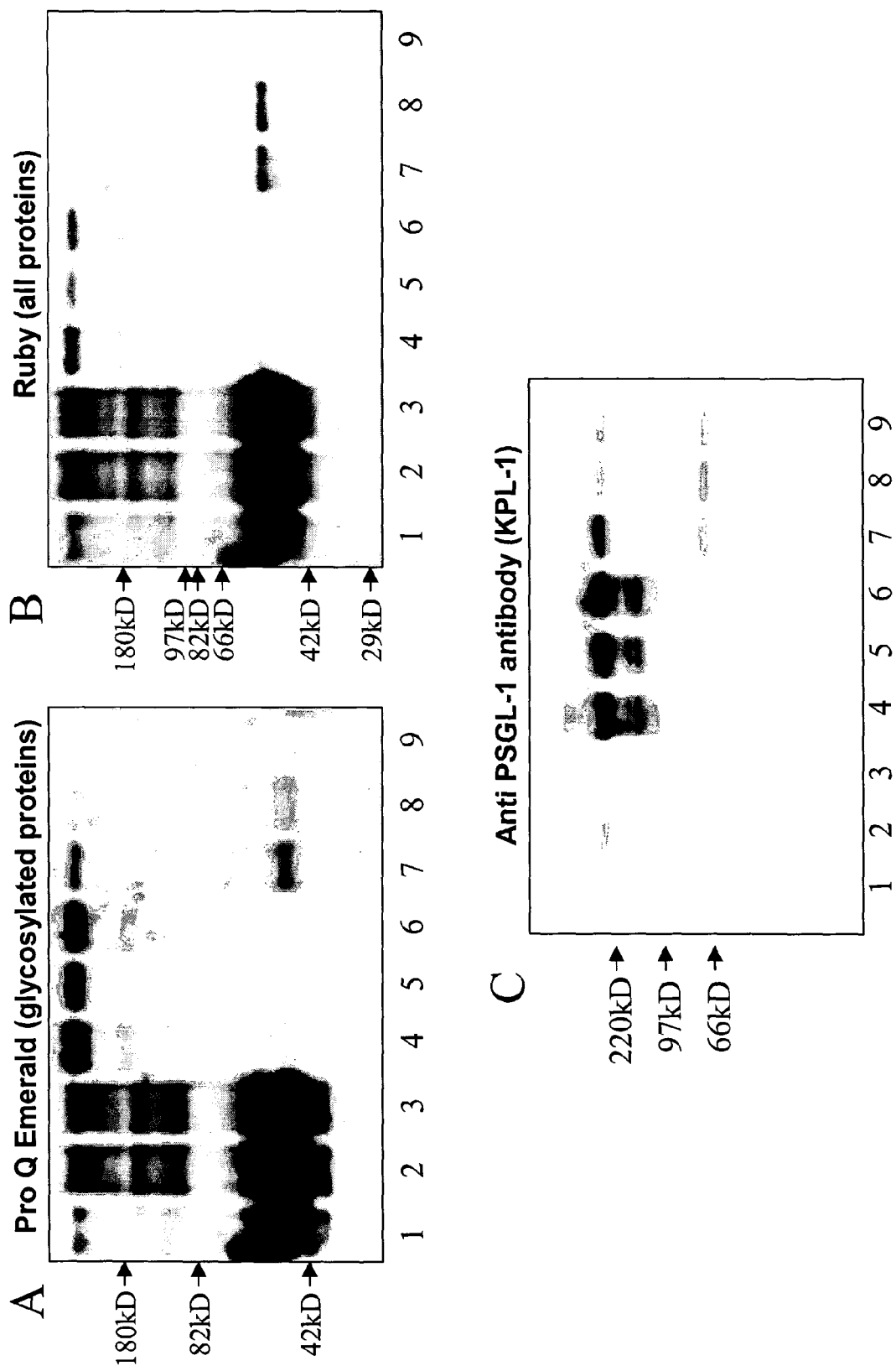
FIG. 11. are photographs of SDS-PAGE and Western blot analysis of PSGL-1/mIgG$_{2b}$ purified by affinity chromatography and gel filtration.

Purification of Recombinant PSGL-1/mIgG$_{2b}$ for Structural Characterization of its O-Linked Glycans Recombinant PSGL-1/mIgG$_{2b}$ was purified from 1 L stirred flask cultures of stably transfected CHO-K1 cells expressing PSGL-1/mIgG$_{2b}$ alone (clone 10), in combination with the porcine α1,3GalT (clone 5L4-1) or in combination with the α1,3GalT and the C2 GnT1 (clone C$_{2-1}$-9). A two-step purification process, involving anti-mouse IgG affinity chromatography and gel filtration, was set up in order to fully remove contaminating glycosylated proteins that could interfere with the O-glycan structural analysis. Affinity purification of two litres of cell supernatant from each cell clone resulted in 2.2 mg, 1.2 mg and 0.95 mg of PSGL-1/mIgG$_{2b}$ from CHO-10, 5L4-1 and C-2-1-9, respectively, as assessed by ELISA. Further purification on a gel filtration column resulted in a final PSGL-1/mIgG$_{2b}$ yield of 0.22 mg, 0.19 mg and 0.29 mg, respectively. The fractions eluted from the affinity and gel filtration columns were analysed by SDS-PAGE and Western blotting (shown here for clone 10). A glycoprotein staining kit was used in combination with Ruby to detect glycosylated as well as non-glycosylated proteins (FIGS. 11A and B), and an anti PSGL-1 antibody confirmed the presence of PSGL-1/mIgG$_{2b}$ (FIG. 11 C). This antibody bound strongly to a band of around 300 kDa (FIG. 11C lanes 2 and 4-9) representing the PSGL-1/mIgG$_{2b}$ dimer. A band of around 150 kDa is also seen (lanes 4-6), derived from the fusion protein in its reduced form, as well as a weak band of 60-70 kDa (lanes 7-9) most likely representing fusion protein break down products. In FIG. 11A and B, a 300 kDa band not stained by the anti PSGL-1 antibody can be seen also in lanes 1 and 3, most likely representing a protein derived from the cell culture medium. This is supported also by its presence in the affinity-purified supernatant (lane 3), which indicates that it is not adsorbed on the anti-Ig affinity column. However, a glycosylated band with a MW of 50-60 kDa, not stained by the anti PSGL-1 antibody, can be seen in the affinity purified fraction (FIG. 11A lane 4). This protein is probably also derived from the cell culture medium, and is adsorbed on the affinity column together with the fusion protein. This protein was removed by gel filtration, during which it eluted later (FIGS. 11A and B, lanes 7-9) than the fusion protein (FIG. 11A, B and C, lanes 5-6). Additional non-glycosylated proteins of around 50-70 kDa were removed by gel filtration (FIG. 11B, compare lane 4 with lanes 7-9). For each clone, the gel filtration fraction containing the highest amount of fusion protein was chosen for oligosaccharide release. As shown for clone 10 (FIG. 11A and B, lane 5), this fraction did not contain any significant amounts of contaminating proteins, glycosylated or non-glycosylated.

Figure 12:
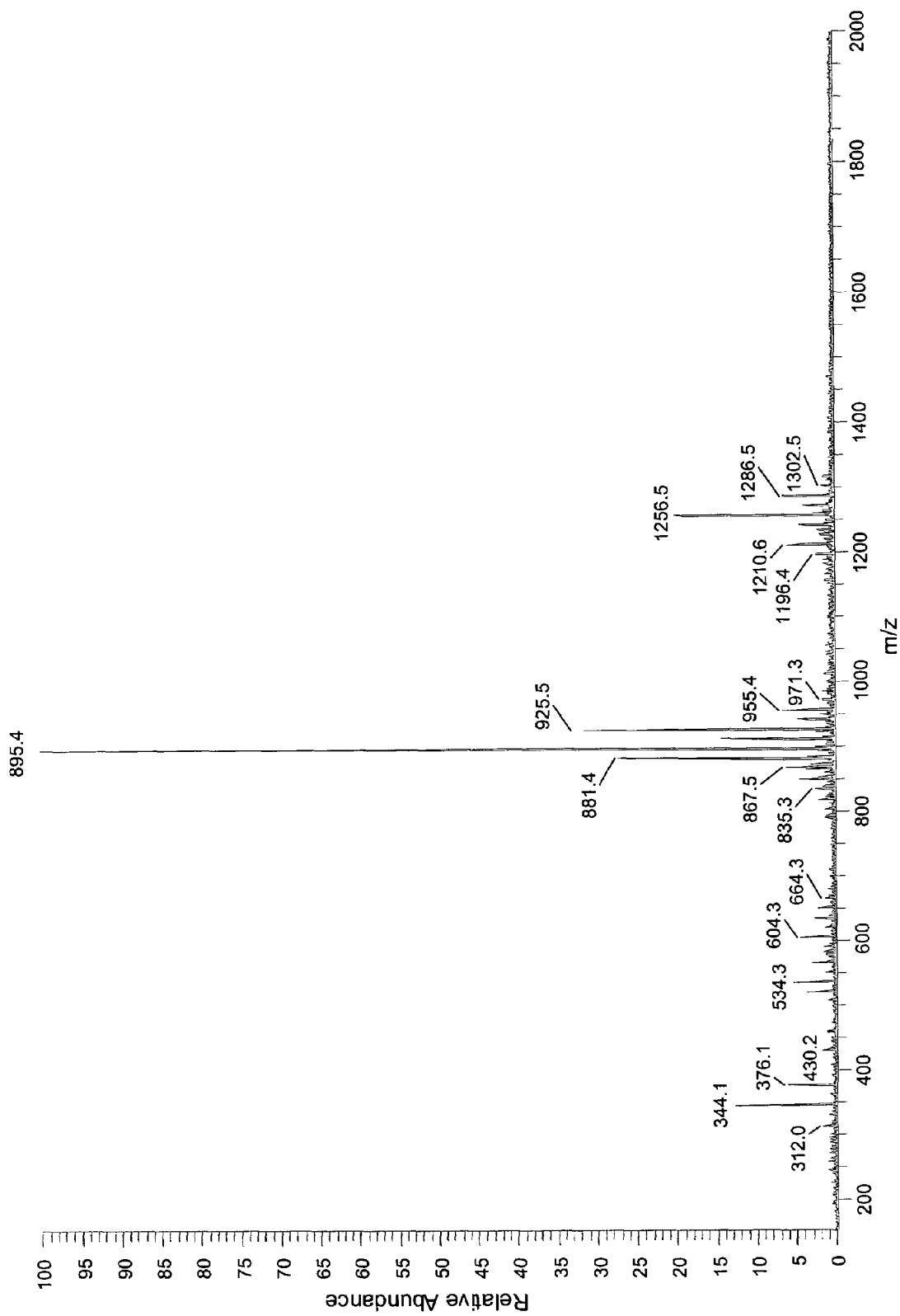
FIG. 12. is an illustration depicting electrospray ion trap mass spectrometry analysi of O-glycans released from PSGL-1/mIgG$_{2b}$ made in CHO clone 5L4-1.
Figure 13:
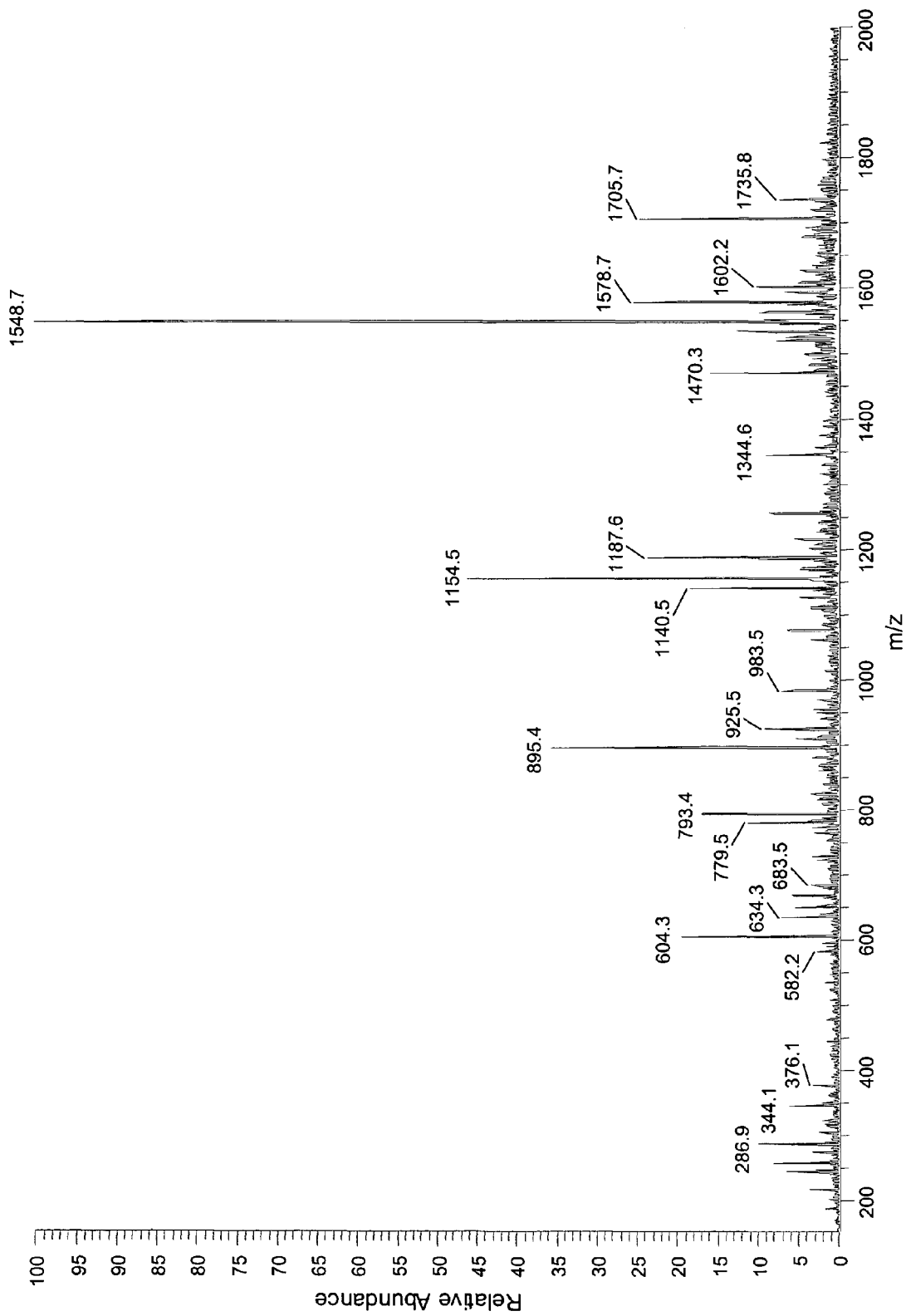
FIG. 13. is an illustration depicting electrospray ion trap mass spectrometry of O-glycans released from PSGL-1/mIgG$_{2b}$ made in CHO clone C2-1-9.

Mass Spectrometry of Permethylated Oligosaccharides Released from Purified, Recombinant PSGL-1/mIgG$_{2b}$ The permethylated oligosaccharides released from clones CHO-10 and 5L4-1 gave similar MS spectra with two predominant groups of peaks around m/z 895.4 and 1256.5 (FIG. 12), while the mass spectrum of O-glycans released from PSGL-1/mIgG$_{2b}$ produced by clone C2-1-9 showed a more complex pattern (FIG. 13). The oligosaccharide sequences of the ions in the ESI-MS spectra were deduced by tandem mass spectrometry (MS/MS). The sequences and tentative structures thus obtained are shown in Table 2. Below, we will describe the results of the MS/MS analyses of the O-glycans on PSGL-1/mIgG$_{2b}$ produced in CHO cells also expressing α1,3GalT and C2 GnT1 (C-2-1-9). All ions in the MS and MS/MS spectra were detected as sodiated ions.

Figure 14:
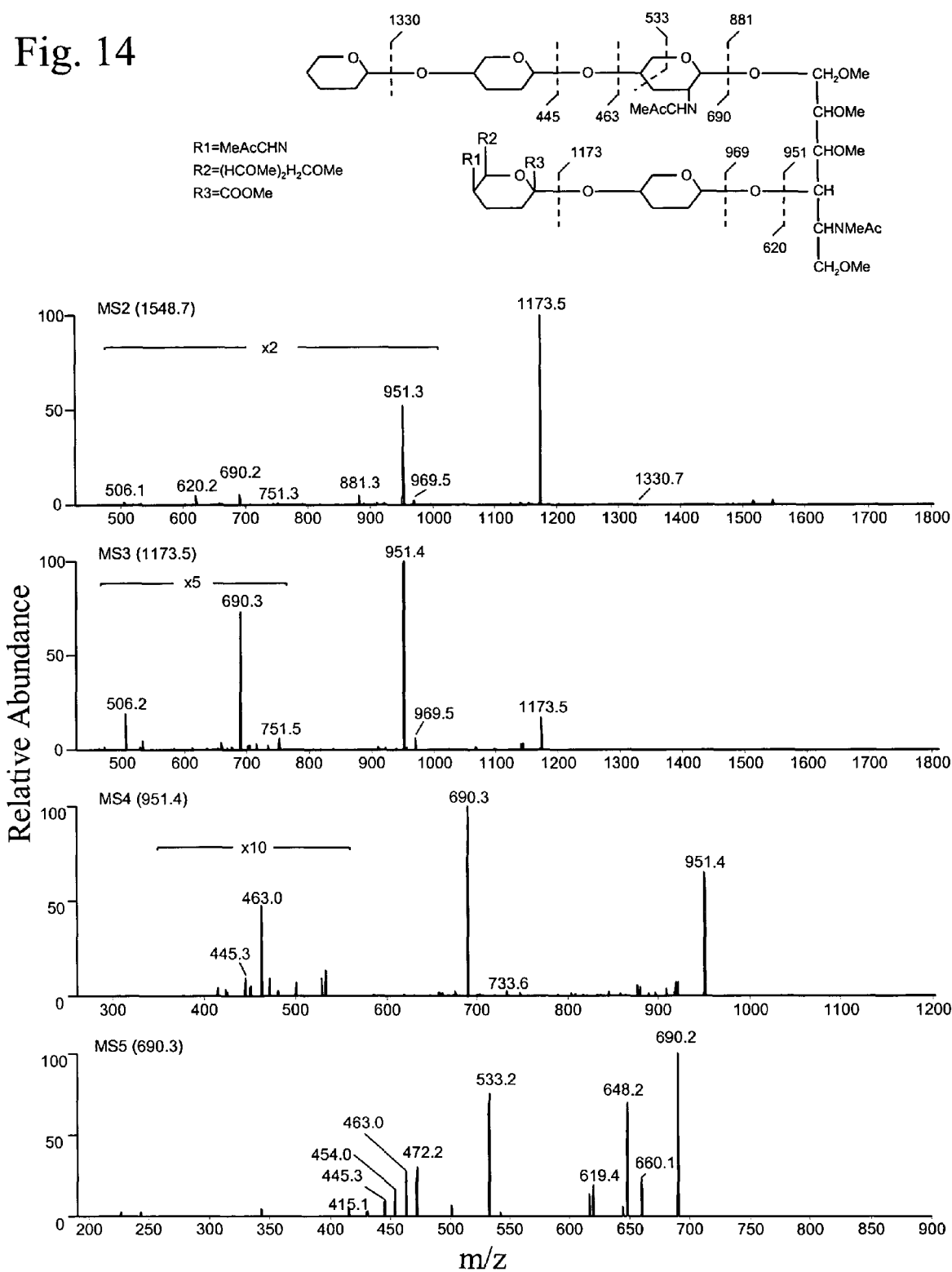
FIG. 14. is a series of illustrations depicting MS/MS analyses of the predominant peak seen in the mother spectra of O-glycans released from PSGL-1/mIgG$_{2b}$ made in CHO clone C2-1-9.

MS/MS analyses of C2-1-9. The most intense peak in the mother spectra is a pseudomolecular ion ([M+Na]$^+$) at m/z 1548.7 representing a NeuAc-Hex-HexNol-HexN-Hex-Hex structure as assessed by MS/MS in sequential steps (FIG. 14). MS$^2$ of this ion gave two major fragment ions at m/z 951.3 ([M−NeuAc-Hex-O+Na]$^+$) and 1173.5 ([M−NeuAc+Na]$^+$) and several minor at m/z 506.1 ([M−Hex-Hex-HexN− NeuAc+Na]$^+$), 620.2 ([NeuAc-Hex-O+Na]$^+$), 690.2 ([Hex-Hex-HexN+Na]$^+$), 751.3 ([M−Hex-Hex−NeuAc+Na]$^+$ or [M−Hex−NeuAc-Hex+Na]$^+$), 881.3 ([M−Hex-Hex-HexN+Na]$^+$), 969.5 ([M−NeuAc-Hex+Na]$^+$) and 1330.7 ([M−Hex+Na]$^+$). The fragment ion at m/z 1173.5 was isolated and analyzed by MS$^3$ resulting in fragment ions at m/z 951.4, 506.2, 690.3 and 751.5. The major peak, 951.4, was further analyzed by MS$^4$ and gave rise to fragment ions at m/z 445.3 ([Hex-Hex+Na]$^+$), 463.0 ([Hex-Hex-O+Na]$^+$), 690.3 and 733.6 ([M−Hex−NeuAc-Hex-O+Na]$^+$). Finally, the dominant fragment ion in the MS$^4$ analysis (690.3) was analyzed by MS$^5$. This resulted in sequence ions at m/z 415.1 and 445.3 representing a terminal Hex-Hex, the former ion having lost one oxygen and its methyl group. A Hex-Hex-O structure was also found (463.0). Further, internal Hex-HexN structures were seen, with (472.2) and without (454.0) one oxygen linked to the hexose. Losses of O-Me (660.1), C—O-Me (648.2) and N—C—O-Me (619.4) from the Hex-Hex-HexN structure was also seen, where the last one probably represents loss of the N-acetyl group from the internal HexN. A major fragment ion at m/z 533.2 was also seen in the MS$^5$ spectra. This ion corresponds to a cross-ring fragment of the innermost HexN (FIG. 14), and indicates that the hexose is linked to the HexN in a 1-4 linkage. This sequence is most likely consistent with a sialidated core 2 elongated with a type 2 structure and a terminal Gal.

Apart from the ion at m/z 1548.7, two other pseudomolecular ions possibly terminating with Galα1,3Gal was found in the ESI-MS spectra of clone C-2-1-9, at m/z 1578.7 and 1187.6. The ion at m/z 1578.7 was isolated for MS$^2$ analysis. The result indicates a NeuGc-Hex-HexNol-HexN-Hex-Hex structure, with fragment ions at m/z 1173.5 ([M−NeuGc+Na]$^+$), 951.5 ([M−NeuGc-Hex-O+Na]$^+$), 911.3 ([M−Hex-Hex-HexN+Na]$^+$), 690.3 ([Hex-Hex-HexN+Na]$^+$) and 676.3 ([Hex-Hex-HexN−Me$^+$ Na]$^+$). MS$^3$ analysis of the 1173.5 ion resulted in a major fragment ion at m/z 951.5 and several minor at m/z 506.1 ([M−Hex-Hex-HexN−NeuAc+Na]$^+$), 690.2 and 969.3 ([M−NeuAc-Hex+Na]$^+$). The fragment ion at m/z 951.5 was analyzed by MS/MS in a fourth step, giving one major fragment ion at m/z 690.4 and a minor one at m/z 658.2 (690.4-O-Me). However, in the MS$^2$ spectra of the ion at m/z 1578.7, unidentified fragment ions at m/z 981.5 and 1203.4 were observed. MS$^3$ and MS$^4$ analyses of the ion at m/z 1203.4 resulted in fragment ions at m/z 981.4, 720.4, 690.1, 506.1 and 688.3 (720.1-O-Me). The ion at m/z 720.4, seen in both the MS$^3$ and MS$^4$ spectra, is 30 mass units more than the characteristic fragment ion at m/z 690.1, representing a Hex-Hex-HexN sequence. Unfortunately, further MS/MS analysis of the ion at m/z 720.4 was not possible. The other pseudomolecular ion in the ESI-MS spectra (FIG. 13) with a possible terminal Galα1,3Gal was observed at m/z 1187.6. MS$^2$ experiment of this ion resulted in fragment ions at m/z 969.5 ([M−Hex+Na]$^+$), 951.4 ([M−Hex-O+Na]$^+$), 756.2 ([M−Hex-Hex+Na]$^+$), 690.3 ([Hex-Hex-HexN+Na]$^+$), 520.3 ([M−Hex-Hex-HexN+Na]$^+$) and 445.1 ([Hex-Hex+Na]$^+$), consistent with a Hex-HexNol-HexN-Hex-Hex or a core 2 with a type 2 elongation and a terminal Gal (Table II). Hence, both neutral and sialylated oligosaccharides potentially expressing terminal Galα1,3Gal is produced by the C2-1-9 clone, although the sialidated (NeuAc) structure seem to be the most abundant one. In addition to this, several sialidated oligosaccharides without terminal Hex-Hex (Galα1-3Gal) can be seen, but at a lower relative abundance (FIG. 13 and Table 2).

TABLE 2

Sequences and tentative structures of PSGL-1/mIgG$_{2b}$ derived O-glycans

| Sequence | MW kDa | Tentative structure | Clone 105L4-1 | Clone C2-1-9 |
|---|---|---|---|---|
| Hex-HexNol-HexN | 779.5 | Galβ1-3[GlcNAcβ1-6]GalNAcol | | X |
| NeuAc-Hex-HexNolNeuAc-HexNol-Hex | 895.4 | NeuAcα2-3Galβ1-3GalNAcol Galβ1-3[NeuAcα2-6]GalNAcol | X | X |
| NeuGc-Hex-HexNol | 925.5 | NeuGcα2-3Galβ1-3GalNAcol | X | X |
| Hex-HexNol-HexN-Hex (Hex-Hex-HexN-HexNol) | 983.5 | Galβ1-3[Galβ1-4GlcNAcβ1-6]GalNol | | X |
| NeuAc-Hex-HexNol-HexN | 1140.5 | NeuAcα2-3Galβ1-3[GlcNAcβ1-6]GalNol | | X |
| Hex-HexNol-HexN-Hex-Hex | 1187.6 | Galβ1-3[Galα1-3Galβ1-4GlcNAcβ1-6]GalNacol | | X |
| NeuAc-Hex-HexNol-NeuAc | 1256.5 | NeuAcα2-3Galβ1-3[NeuAcα2-6]GalNAcol | X | X |
| NeuGc-Hex-HexNol-NeuAc | 1286.5 | NeuGcα2-3Galβ1-3[NeuAcα2-6]GalNAcol | X | |
| NeuAc-Hex-HexNol-NeuGc | | NeuAcα2-3Galβ1-3[NeuGcα2-6]GalNAcol | | |
| NeuGc-Hex-HexNol-NeuGc | 1316.5 | NeuGcα2-3Galβ1-3[NeuGcα2-6]GalNAcol | X | |
| Hex-HexNol-HexN-Hex-NeuAcNeuAc-Hex-HexNol-HexN-Hex | 1344.6 | Galβ1-3[NeuAcα2-3Galβ1-4GlcNAcβ1-6]GalNAcol NeuAcα2-3Galβ1-3[Galβ1-4GlcNAcβ1-6]GalNAcol | | X |
| NeuAc-Hex-HexNol-HexN-Hex-Hex | 1548.7 | NeuAcα2-3[Galα1-3Galβ1-4GlcNAcβ1-6]GalNAcol | | X |
| NeuGc-Hex-HexNol-HexN-Hex-Hex | 1578.7 | NeuGcα2-3[Galα1-3Galβ1-4GlcNAcβ1-6]GalNAcol | | X |
| NeuAc-Hex-HexNol-HexN-Hex-NeuAc | 1705.7 | NeuAcα2-3[NeuAcα2-3Galβ1-4GlcNAcβ1-6]GalNAcol | | X |
| NeuGc-Hex-HexNol-HexN-Hex-NeuAc NeuAc-Hex-HexNol-HexN-Hex-NeuGc | 1735.8 | NeuGcα2-3[NeuAcα2-3Galβ1-4GlcNAcβ1-6]GalNAcol NeuAcα2-3[NeuGcα2-3Galβ1-4GlcNAcβ1-6]GalNAcol | | X |

EXAMPLE 3

Expression Vectors

Exemplary expression vectors usefl in the production of the fusion polypeptides are as follows:

TABLE 3

```
Core 2 beta1-6 GlcNAc transferase Expression vector
         (SEQ ID NO:1; 4917 nucleotides)

1  GGCGTAATCT GCTGCTTGCA AACAAAAAAA CCACCGCTAC CAGCGGTGGT

51  TTGTTTGCCG GATCAAGAGC TACCAACTCT TTTTCCGAAG GAACTGGCTT

101  CAGCAGAGCG CAGATACCAA ATACTGTCCT TCTAGTGTAG CCGTAGTTAG

151  GCCACCACTT CAAGAACTCT GTAGCACCGC CTACATACCT CGCTCTGCTA

201  ATCCTGTTAC CAGTGGCTGC TGCCAGTGGC GATAAGTCGT GTCTTACCGG

251  GTTGGACTCA AGACGATAGT TACCGGATAA GGCGCAGCGG TCGGGCTGAA

301  CGGGGGGTTC GTGCACACAG CCCAGCTTGG AGCGAACGAC CTACACCGAA

351  CTGAGATACC TACAGCGTGA GCTATGAGAA AGCGCCACGC TTCCCGAAGG

401  GAGAAAGGCG GACAGGTATC CGGTAAGCGG CAGGGTCGGA ACAGGAGAGC

451  GCACGAGGGA GCTTCCAGGG GGAAACGCCT GGTATCTTTA TAGTCCTGTC

501  GGGTTTCGCC ACCTCTGACT TGAGCGTCGA TTTTTGTGAT GCTCGTCAGG

551  GGGGCGGAGC CTATGGAAAA ACGCCAGCAA CGCCGAATTA CCGCGGTCTT
```

TABLE 3-continued

Core 2 beta1-6 GlcNAc transferase Expression vector
(SEQ ID NO:1; 4917 nucleotides)

```
 601 TCGGACTTTT GAAAGTGATG GTGGTGGGGG AAGGATTCGA ACCTTCGAAG
 651 TCGATGACGG CAGATTTAGA GTCTGCTCCC TTTGGCCGCT CGGGAACCCC
 701 ACCACGGGTA ATGCTTTTAC TGGCCTGCTC CCTTATCGGG AAGCGGGGCG
 751 CATCATATCA AATGACGCGC CGCTGTAAAG TGTTACGTTG AGAAAGCTGC
 801 TCCCTGCTTG TGTGTTGGAG GTCGCTGAGT AGTGCGCGAG TAAAATTTAA
 851 GCTACAACAA GGCAAGGCTT GACCGACAAT TGCATGAAGA ATCTGCTTAG
 901 GGTTAGGCGT TTTGCGCTGC TTCGGactag tGAGGCTCCG GTGCCCGTCA
 951 GTGGGCAGAG CGCACATCGC CCACAGTCCC CGAGAAGTTG GGGGAGGGG
1001 TCGGCAATTG AACCGGTGCC TAGAGAAGGT GGCGCGGGGT AAACTGGGAA
1051 AGTGATGTCG TGTACTGGCT CCGCCTTTTT CCCGAGGGTG GGGGAGAACC
1101 GTATATAAGT GCAGTAGTCG CCGTGAACGT TCTTTTTCGC AACGGGTTTG
1151 CCGCCAGAAC ACAGGTAAGT GCCGTGTGTG GTTCCCGCGG GCCTGGCCTC
1201 TTTACGGGTT ATGGCCCTTG CGTGCCTTGA ATTACTTCCA CGCCCCTGGC
1251 TGCAGTACGT GATTCTTGAT CCCGAGCTTC GGGTTGGAAG TGGGTGGGAG
1301 AGTTCGAGGC CTTGCGCTTA AGGAGCCCCT TCGCCTCGTG CTTGAGTTGA
1351 GGCCTGGCCT GGGCGCTGGG GCCGCCGCGT GCGAATCTGG TGGCACCTTC
1401 GCGCCTGTCT CGCTGCTTTC GATAAGTCTC TAGCCATTTA AAATTTTTGA
1451 TGACCTGCTG CGACGCTTTT TTTCTGGCAA GATAGTCTTG TAAATGCGGG
1501 CCAAGATCTG CACACTGGTA TTTCGGTTTT TGGGGCCGCG GCGGCGACG
1551 GGGCCCGTGC GTCCCAGCGC ACATGTTCGG CGAGGCGGG CCTGCGAGCG
1601 CGGCCACCGA GAATCGGACG GGGGTAGTCT CAAGCTGGCC GGCCTGCTCT
1651 GGTGCCTGGC CTCGCGCCGC CGTGTATCGC CCCGCCCTGG GCGGCAAGGC
1701 TGGCCCGGTC GGCACCAGTT GCGTGAGCGG AAAGATGGCC GCTTCCCGGC
1751 CCTGCTGCAG GGAGCTCAAA ATGGAGGACG CGGCGCTCGG GAGAGCGGGC
1801 GGGTGAGTCA CCCACACAAA GGAAAAGGGC CTTTCCGTCC TCAGCCGTCG
1851 CTTCATGTGA CTCCACGGAG TACCGGGCGC CGTCCAGGCA CCTCGATTAG
1901 TTCTCGAGCT TTTGGAGTAC GTCGTCTTTA GGTTGGGGGG AGGGGTTTTA
1951 TGCGATGGAG TTTCCCCACA CTGAGTGGGT GGAGACTGAA GTTAGGCCAG
2001 CTTGGCACTT GATGTAATTC TCCTTGGAAT TTGCCCTTTT TGAGTTTGGA
2051 TCTTGGTTCA TTCTCAAGCC TCAGACAGTG GTTCAAAGTT TTTTTCTTCC
2101 ATTTCAGGTG TCGTGAAAAG CTTCTAGAGA TCCCTCGACC TCGAGACCAT
2151 GCTGAGGACG TTGCTGCGAA GGAGACTTTT TTCTTATCCC ACCAAATACT
2201 ACTTTATGGT TCTTGTTTTA TCCCTAATCA CCTTCTCCGT TTTAAGGATT
2251 CATCAAAAGC CTGAATTTGT AAGTGTCAGA CACTTGGAGC TTGCTGGGA
2301 GAATCCTAGT AGTGATATTA ATTGCACCAA AGTTTTACAG GGTGATGTAA
2351 ATGAAATCCA AAGGTAAAG CTTGAGATCC TAACAGTGAA ATTTAAAAAG
2401 CGCCCTCGGT GGACACCTGA CGACTATATA AACATGACCA GTGACTGTTC
2451 TTCTTTCATC AAGAGACGCA AATATATTGT AGAACCCCTT AGTAAAGAAG
```

TABLE 3-continued

Core 2 beta1-6 GlcNAc transferase Expression vector
(SEQ ID NO:1; 4917 nucleotides)

```
2501 AGGCGGAGTT TCCAATAGCA TATTCTATAG TGGTTCATCA CAAGATTGAA
2551 ATGCTTGACA GGCTGCTGAG GGCCATCTAT ATGCCTCAGA ATTTCTATTG
2601 CGTTCATGTG GACACAAAAT CCGAGGATTC CTATTTAGCT GCAGTGATGG
2651 GCATCGCTTC CTGTTTTAGT AATGTCTTTG TGGCCAGCCG ATTGGAGAGT
2701 GTGGTTTATG CATCGTGGAG CCGGGTTCAG GCTGACCTCA ACTGCATGAA
2751 GGATCTCTAT GCAATGAGTG CAAACTGGAA GTACTTGATA AATCTTTGTG
2801 GTATGGATTT TCCCATTAAA ACCAACCTAG AAATTGTCAG GAAGCTCAAG
2851 TTGTTAATGG GAGAAAACAA CCTGGAAACG GAGAGGATGC CATCCCATAA
2901 AGAAGAAAGG TGGAAGAAGC GGTATGAGGT CGTTAATGGA AAGCTGACAA
2951 ACACAGGGAC TGTCAAAATG CTTCCTCCAC TCGAAACACC TCTCTTTTCT
3001 GGCAGTGCCT ACTTCGTGGT CAGTAGGGAG TATGTGGGGT ATGTACTACA
3051 GAATGAAAAA ATCCAAAAGT TGATGGAGTG GGCACAAGAC ACATACAGCC
3101 CTGATGAGTA TCTCTGGGCC ACCATCCAAA GGATTCCTGA AGTCCCGGGC
3151 TCACTCCCTG CCAGCCATAA GTATGATCTA TCTGACATGC AAGCAGTTGC
3201 CAGGTTTGTC AAGTGGCAGT ACTTTGAGGG TGATGTTTCC AAGGGTGCTC
3251 CCTACCCGCC CTGCGATGGA GTCCATGTGC GCTCAGTGTG CATTTTCGGA
3301 GCTGGTGACT TGAACTGGAT GCTGCGCAAA CACCACTTGT TTGCCAATAA
3351 GTTTGACGTG GATGTTGACC TCTTTGCCAT CCAGTGTTTG ATGAGCATT
3401 TGAGACACAA AGCTTTGGAG ACATTAAAAC ACTGAGCGGC CGCCGCAGGT
3451 AAGCCAGCCC AGGCCTCGCC CTCCAGCTCA AGGCGGGACA GGTGCCCTAG
3501 AGTAGCCTGC ATCCAGGGAC AGGCCCCAGC CGGGTGCTGA CACGTCCACC
3551 TCCATCTCTT CCTCAGTTAA CTTGTTTATT GCAGCTTATA ATGGTTACAA
3601 ATAAAGCAAT AGCATCACAA ATTTCACAAA TAAAGCATTT TTTTCACTGC
3651 ATTCTAGTTG TGGTTTGTCC AAACTCATCA ATGTATCTTA TCATGTCTGG
3701 ATCCTCAGAA GAACTCGTCA AGAAGGCGAT AGAAGGCGAT GCGCTGCGAA
3751 TCGGGAGCGG CGATACCGTA AAGCACGAGG AAGCGGTCAG CCCATTCGCC
3801 GCCAAGCTCT TCAGCAATAT CACGGGTAGC CAACGCTATG TCCTGATAGC
3851 GGTCCGCCAC ACCCAGCCGG CCACAGTCGA TGAATCCAGA AAAGCGGCCA
3901 TTTTCCACCA TGATATTCGG CAAGCAGGCA TCGCCATGGG TCACGACGAG
3951 ATCCTCGCCG TCGGGCATGC GCGCCTTGAG CCTGGCGAAC AGTTCGGCTG
4001 GCGCGAGCCC CTGATGCTCT TCGTCCAGAT CATCCTGATC GACAAGACCG
4051 GCTTCCATCC GAGTACGTGC TCGCTCGATG CGATGTTTCG CTTGGTGGTC
4101 GAATGGGCAG GTAGCCGGAT CAAGCGTATG CAGCCGCCGC ATTGCATCAG
4151 CCATGATGGA TACTTTCTCG GCAGGAGCAA GGTGAGATGA CAGGAGATCC
4201 TGCCCCGGCA CTTCGCCCAA TAGCAGCCAG TCCCTTCCCG CTTCAGTGAC
4251 AACGTCGAGC ACAGCTGCGC AAGGAACGCC CGTCGTGGCC AGCCACGATA
4301 GCCGCGCTGC CTCGTCCTGC AGTTCATTCA GGGCACCGGA CAGGTCGGTC
4351 TTGACAAAAA GAACCGGGCG CCCCTGCGCT GACAGCCGGA ACACGGCGGC
```

TABLE 3-continued

Core 2 beta1-6 GlcNAc transferase Expression vector
(SEQ ID NO:1; 4917 nucleotides)

```
4401 ATCAGAGCAG CCGATTGTCT GTTGTGCCCA GTCATAGCCG AATAGCCTCT

4451 CCACCCAAGC GGCCGGAGAA CCTGCGTGCA ATCCATCTTG TTCAATCATG

4501 GTCCTGCAGA GTCGCTCGGT GTTCGAGGCC ACACGCGTCA CCTTAATATG

4551 CGAAGTGGAC CTGGGACCGC GCCGCCCCGA CTGCATCTGC GTGTTCGAAT

4601 TCGCCAATGA CAAGACGCTG GGCGGGGTTT GTGTCATCAT AGAACTAAAG

4651 ACATGCAAAT ATATTTCTTC CGGGGACACC GCCAGCAAAC GCGAGCAACG

4701 GGCCACGGGG ATGAAGCAGC TGCGCCACTC CCTGAAGATC TCCCGCCCCT

4751 AACTCCGCCC ATCCCGCCCC TAACTCCGCC CAGTTCCGCC CATTCTCCGC

4801 CCCATGGCTG ACTAATTTTT TTTATTTATG CAGAGGCCGA GGCCGCGGCC

4851 TCTGAGCTAT TCCAGAAGTA GTGAGGAGGC TTTTTTGGAG GCCTAGGCTT

4901 TTGCAAAAAG CTAATTC
```

TABLE 4

| Nucleic Acid | Corresponding Nucleotide position in SEQ ID NO:1 | SEQ ID NO |
|---|---|---|
| pMB1 origin (pBR322 ori) | 1-593 | 2 |
| sac2) synthetic tyrosine suppressor tRNA gene(supF gene)remnant of ASV LTR | 594-925 | 3 |
| (spe) EF1alpha prom | 926-2139 | 4 |
| (xho) Core 2 beta1-6 GlcNAc transferase 1 | 2140-3435 | 5 |
| (not) IgG1 hinge/CH2 intron | 3436-3565 | 6 |
| (hpa1) SV40 poly A | 3566-3698 | 7 |
| (bamh1) neomycin (rev) | 3699-4503 | 8 |
| (pst) HSV1 tk promoter −215 to +19, with G to A mutation at +7 | 4504-4735 | 9 |
| (bgl2) SV40 origin (minus enhancer) | 4736-4917 | 10 |

TABLE 5

Porcine α1,3 Galactosyltransferase Expression vector
(SEQ ID NO:11; 4930 nucleotides)

```
  1 GGCGTAATCT GCTGCTTGCA AACAAAAAAA CCACCGCTAC CAGCGGTGGT

51 TTGTTTGCCG GATCAAGAGC TACCAACTCT TTTTCCGAAG GAACTGGCTT

101 CAGCAGAGCG CAGATACCAA ATACTGTCCT TCTAGTGTAG CCGTAGTTAG

151 GCCACCACTT CAAGAACTCT GTAGCACCGC CTACATACCT CGCTCTGCTA

201 ATCCTGTTAC CAGTGGCTGC TGCCAGTGGC GATAAGTCGT GTCTTACCGG

251 GTTGGACTCA AGACGATAGT TACCGGATAA GGCGCAGCGG TCGGGCTGAA

301 CGGGGGGTTC GTGCACACAG CCCAGCTTGG AGCGAACGAC CTACACCGAA

351 CTGAGATACC TACAGCGTGA GCTATGAGAA AGCGCCACGC TTCCCGAAGG

401 GAGAAAGGCG GACAGGTATC CGGTAAGCGG CAGGGTCGGA ACAGGAGAGC

451 GCACGAGGGA GCTTCCAGGG GGAAACGCCT GGTATCTTTA TAGTCCTGTC

501 GGGTTTCGCC ACCTCTGACT TGAGCGTCGA TTTTTGTGAT GCTCGTCAGG

551 GGGGCGGAGC CTATGGAAAA ACGCCAGCAA CGCCGAATTA CCGCGGTCTT

601 TCGGACTTTT GAAAGTGATG GTGGTGGGGG AAGGATTCGA ACCTTCGAAG

651 TCGATGACGG CAGATTTAGA GTCTGCTCCC TTTGGCCGCT CGGGAACCCC
```

TABLE 5-continued

Porcine α1,3 Galactosyltransferase Expression vector
(SEQ ID NO:11; 4930 nucleotides)

```
 701 ACCACGGGTA ATGCTTTTAC TGGCCTGCTC CCTTATCGGG AAGCGGGGCG
 751 CATCATATCA AATGACGCGC CGCTGTAAAG TGTTACGTTG AGAAAGCTGC
 801 TCCCTGCTTG TGTGTTGGAG GTCGCTGAGT AGTGCGCGAG TAAAATTTAA
 851 GCTACAACAA GGCAAGGCTT GACCGACAAT GCATGAAGA ATCTGCTTAG
 901 GGTTAGGCGT TTTGCGCTGC TTCGGactag tGAGGCTCCG GTGCCCGTCA
 951 GTGGGCAGAG CGCACATCGC CCACAGTCCC CGAGAAGTTG GGGGAGGGG
1001 TCGGCAATTG AACCGGTGCC TAGAGAAGGT GGCGCGGGGT AAACTGGGAA
1051 AGTGATGTCG TGTACTGGCT CCGCCTTTTT CCCGAGGGTG GGGGAGAACC
1101 GTATATAAGT GCAGTAGTCG CCGTGAACGT TCTTTTTCGC AACGGGTTTG
1151 CCGCCAGAAC ACAGGTAAGT GCCGTGTGTG GTTCCCGCGG GCCTGGCCTC
1201 TTTACGGGTT ATGGCCCTTG CGTGCCTTGA ATTACTTCCA CGCCCCTGGC
1251 TGCAGTACGT GATTCTTGAT CCCGAGCTTC GGGTTGGAAG TGGGTGGGAG
1301 AGTTCGAGGC CTTGCGCTTA AGGAGCCCCT TCGCCTCGTG CTTGAGTTGA
1351 GGCCTGGCCT GGGCGCTGGG GCCGCCGCGT GCGAATCTGG TGGCACCTTC
1401 GCGCCTGTCT CGCTGCTTTC GATAAGTCTC TAGCCATTTA AAATTTTTGA
1451 TGACCTGCTG CGACGCTTTT TTTCTGGCAA GATAGTCTTG TAAATGCGGG
1501 CCAAGATCTG CACACTGGTA TTTCGGTTTT TGGGGCCGCG GGCGGCGACG
1551 GGGCCCGTGC GTCCCAGCGC ACATGTTCGG CGAGGCGGGG CCTGCGAGCG
1601 CGGCCACCGA GAATCGGACG GGGGTAGTCT CAAGCTGGCC GGCCTGCTCT
1651 GGTGCCTGGC CTCGCGCCGC CGTGTATCGC CCCGCCCTGG GCGGCAAGGC
1701 TGGCCCGGTC GGCACCAGTT GCGTGAGCGG AAAGATGGCC GCTTCCCGGC
1751 CCTGCTGCAG GGAGCTCAAA ATGGAGGACG CGGCGCTCGG GAGAGCGGGC
1801 GGGTGAGTCA CCCACACAAA GGAAAAGGGC CTTTCCGTCC TCAGCCGTCG
1851 CTTCATGTGA CTCCACGGAG TACCGGGCGC CGTCCAGGCA CCTCGATTAG
1901 TTCTCGAGCT TTTGGAGTAC GTCGTCTTTA GGTTGGGGGG AGGGGTTTTA
1951 TGCGATGGAG TTTCCCCACA CTGAGTGGGT GGAGACTGAA GTTAGGCCAG
2001 CTTGGCACTT GATGTAATTC TCCTTGGAAT TGCCCTTTT TGAGTTTGGA
2051 TCTTGGTTCA TTCTCAAGCC TCAGACAGTG GTTCAAAGTT TTTTTCTTCC
2101 ATTTCAGGTG TCGTGAAaag cttaccATGA ATGTCAAAGG AAGAGTGGTT
2151 CTGTCAATGC TGCTTGTCTC AACTGTAATG GTTGTGTTTT GGGAATACAT
2201 CAACAGAAAC CCAGAAGTTG GCAGCAGTGC TCAGAGGGGC TGGTGGTTTC
2251 CGAGCTGGTT TAACAATGGG ACTCACAGTT ACCACGAAGA AGAAGACGCT
2301 ATAGGCAACG AAAAGGAACA AGAAAAGAA GACAACAGAG GAGAGCTTCC
2351 GCTAGTGGAC TGGTTTAATC CTGAGAAACG CCCAGAGGTC GTGACCATAA
2401 CCAGATGGAA GGCTCCAGTG GTATGGGAAG GCACTTACAA CAGAGCCGTC
2451 TTAGATAATT ATTATGCCAA ACAGAAAATT ACCGTGGGCT TGACGGTTTT
2501 TGCTGTCGGA AGATACATTG AGCATTACTT GGAGGAGTTC TTAATATCTG
2551 CAAATACATA CTTCATGGTT GGCCACAAAG TCATCTTTTA CATCATGGTG
```

TABLE 5-continued

Porcine α1,3 Galactosyltransferase Expression vector
(SEQ ID NO:11; 4930 nucleotides)

```
2601 GATGATATCT CCAGGATGCC TTTGATAGAG CTGGGTCCTC TGCGTTCCTT

2651 TAAAGTGTTT GAGATCAAGT CCGAGAAGAG GTGGCAAGAC ATCAGCATGA

2701 TGCGCATGAA GACCATCGGG GAGCACATCC TGGCCCACAT CCAGCACGAG

2751 GTGGACTTCC TCTTCTGCAT TGACGTGGAT CAGGTCTTCC AAAACAACTT

2801 TGGGGTGGAG ACCCTGGGCC AGTCGGTGGC TCAGCTACAG GCCTGGTGGT

2851 ACAAGGCACA TCCTGACGAG TTCACCTACG AGAGGCGGAA GGAGTCCGCA

2901 GCCTACATTC CGTTTGGCCA GGGGGATTTT TATTACCACG CAGCCATTTT

2951 TGGGGGAACA CCCACTCAGG TTCTAAACAT CACTCAGGAG TGCTTCAAGG

3001 GAATCCTCCA GGACAAGGAA AATGACATAG AAGCCGAGTG GCATGATGAA

3051 AGCCATCTAA ACAAGTATTT CCTTCTCAAC AAACCCACTA AATCTTATC

3101 CCCAGAATAC TGCTGGGATT ATCATATAGG CATGTCTGTG GATATTAGGA

3151 TTGTCAAGAT AGCTTGGCAG AAAAAAGAGT ATAATTTGGT TAGAAATAAC

3201 ATCTGAgcgg ccgcCGCAGG TAAGCCAGCC CAGGCCTCGC CCTCCAGCTC

3251 AAGGCGGGAC AGGTGCCCTA GAGTAGCCTG CATCCAGGGA CAGGCCCCAG

3301 CCGGGTGCTG ACACGTCCAC CTCCATCTCT TCCTCAGTTA ACTTGTTTAT

3351 TGCAGCTTAT AATGGTTACA AATAAAGCAA TAGCATCACA AATTTCACAA

3401 ATAAAGCATT TTTTTCACTG CATTCTAGTT GTGGTTTGTC CAAACTCATC

3451 AATGTATCTT ATCATGTCTg gatccGCTAG CGCTTTATTC CTTTGCCCTC

3501 GGACGAGTGC TGGGGCGTCG GTTTCCACTA TCGGCGAGTA CTTCTACACA

3551 GCCATCGGTC CAGACGGCCG CGCTTCTGCG GGCGATTTGT GTACGCCCGA

3601 CAGTCCCGGC TCCGGATCGG ACGATTGCGT CGCATCGACC CTGCGCCCAA

3651 GCTGCATCAT CGAAATTGCC GTCAACCAAG CTCTGATAGA GTTGGTCAAG

3701 ACCAATGCGG AGCATATACG CCCGGAGCCG CGGCGATCCT GCAAGCTCCG

3751 GATGCCTCCG CTCGAAGTAG CGCGTCTGCT GCTCCATACA AGCCAACCAC

3801 GGCCTCCAGA AGAAGATGTT GGCGACCTCG TATTGGGAAT CCCCGAACAT

3851 CGCCTCGCTC CAGTCAATGA CCGCTGTTAT GCGGCCATTG TCCGTCAGGA

3901 CATTGTTGGA GCCGAAATCC GCGTGCACGA GGTGCCGGAC TTCGGGCAG

3951 TCCTCGGCCC AAAGCATCAG CTCATCGAGA GCCTGCGCGA CGGACGCACT

4001 GACGGTGTCG TCCATCACAG TTTGCCAGTG ATACACATGG GGATCAGCAA

4051 TCGCGCATAT GAAATCACGC CATGTAGTGT ATTGACCGAT TCCTTGCGGT

4101 CCGAATGGGC CGAACCCGCT CGTCTGGCTA AGATCGGCCG CAGCGATCGC

4151 ATCCATCGCC TCCGCGACCG GCTGCAGAAC AGCGGGCAGT TCGGTTTCAG

4201 GCAGGTCTTG CAACGTGACA CCCTGTGCAC GGCGGGAGAT GCAATAGGTC

4251 AGGCTCTCGC TGAATTCCCC AATGTCAAGC ACTTCCGGAA TCGGGAGCGC

4301 GGCCGATGCA AAGTGCCGAT AAACATAACG ATCTTTGTAG AAACCATCGG

4351 CGCAGCTATT TACCCGCAGG ACATATCCAC GCCCTCCTAC ATCGAAGCTG

4401 AAAGCACGAG ATTCTTCGCC CTCCGAGAGC TGCATCAGGT CGGAGACGCT

4451 GTCGAACTTT TCGATCAGAA ACTTCTCGAC AGACGTCGCG GTGAGTTCAG
```

TABLE 5-continued

Porcine α1,3 Galactosyltransferase Expression vector
(SEQ ID NO:11; 4930 nucleotides)

```
4501  GCTTTTTCAT GGTGGCCTGC AGAGTCGCTC GGTGTTCGAG GCCACACGCG

4551  TCACCTTAAT ATGCGAAGTG GACCTGGGAC CGCGCCGCCC CGACTGCATC

4601  TGCGTGTTCG AATTCGCCAA TGACAAGACG CTGGGCGGGG TTTGTGTCAT

4651  CATAGAACTA AAGACATGCA AATATATTTC TTCCGGGGAC ACCGCCAGCA

4701  AACGCGAGCA ACGGGCCACG GGGATGAAGC AGCTGCGCCA CTCCCTGAAG

4751  ATCTCCCGCC CCTAACTCCG CCCATCCCGC CCCTAACTCC GCCCAGTTCC

4801  GCCCATTCTC CGCCCCATGG CTGACTAATT TTTTTTATTT ATGCAGAGGC

4851  CGAGGCCGCG GCCTCTGAGC TATTCCAGAA GTAGTGAGGA GGCTTTTTG

4901  GAGGCCTAGG CTTTTGCAAA AAGCTAATTC
```

TABLE 6

| Nucleic Acid | Corresponding Nucleotide position in SEQ ID NO:11 | SEQ ID NO |
|---|---|---|
| pMB1 origin (pBR322 ori) | 1-593 | 12 |
| sac2) synthetic tyrosine suppressor tRNA gene(supF gene)remnant of ASV LTR | 594-925 | 13 |
| (spe) EF1alpha prom | 926-2117 | 14 |
| (hind3) porcine alpha1,3galactosyltransferase | 2118-3206 | 15 |
| (not) IgG1 hinge/CH2 intron | 3207-3336 | 16 |
| (hpa1) SV40 poly A | 3337-3469 | 17 |
| (bamh1) hygromycin b (rev) | 3470-4503 | 18 |
| (pst) HSV1 tk promoter −215 to +19, with G to A mutation at +7 | 4517-4748 | 19 |
| (bgl2) SV40 origin (minus enhancer) | 4749-4930 | 20 |

TABLE 7

Human PSGL-1 Expression vector
(SEQ ID NO:21; 5204 nucleotides)

```
  1  GGCGTAATCT GCTGCTTGCA AACAAAAAAA CCACCGCTAC CAGCGGTGGT

51  TTGTTTGCCG GATCAAGAGC TACCAACTCT TTTTCCGAAG GAACTGGCTT

101  CAGCAGAGCG CAGATACCAA ATACTGTCCT TCTAGTGTAG CCGTAGTTAG

151  GCCACCACTT CAAGAACTCT GTAGCACCGC CTACATACCT CGCTCTGCTA

201  ATCCTGTTAC CAGTGGCTGC TGCCAGTGGC GATAAGTCGT GTCTTACCGG

251  GTTGGACTCA AGACGATAGT TACCGGATAA GGCGCAGCGG TCGGGCTGAA

301  CGGGGGGTTC GTGCACACAG CCCAGCTTGG AGCGAACGAC CTACACCGAA

351  CTGAGATACC TACAGCGTGA GCTATGAGAA AGCGCCACGC TTCCCGAAGG

401  GAGAAAGGCG GACAGGTATC CGGTAAGCGG CAGGGTCGGA ACAGGAGAGC

451  GCACGAGGGA GCTTCCAGGG GGAAACGCCT GGTATCTTTA TAGTCCTGTC

501  GGGTTTCGCC ACCTCTGACT TGAGCGTCGA TTTTTGTGAT GCTCGTCAGG

551  GGGGCGGAGC CTATGGAAAA ACGCCAGCAA CGCCGAATTA CCGCGGTCTT

601  TCGGACTTTT GAAAGTGATG GTGGTGGGGG AAGGATTCGA ACCTTCGAAG

651  TCGATGACGG CAGATTTAGA GTCTGCTCCC TTTGGCCGCT CGGGAACCCC

701  ACCACGGGTA ATGCTTTTAC TGGCCTGCTC CCTTATCGGG AAGCGGGGCG

751  CATCATATCA AATGACGCGC CGCTGTAAAG TGTTACGTTG AGAAAGCTGC
```

TABLE 7-continued

| Human PSGL-1 Expression vector |
| (SEQ ID NO:21; 5204 nucleotides) |

```
 801 TCCCTGCTTG TGTGTTGGAG GTCGCTGAGT AGTGCGCGAG TAAAATTTAA
 851 GCTACAACAA GGCAAGGCTT GACCGACAAT TGCATGAAGA ATCTGCTTAG
 901 GGTTAGGCGT TTTGCGCTGC TTCGGactag tGAGGCTCCG GTGCCCGTCA
 951 GTGGGCAGAG CGCACATCGC CCACAGTCCC CGAGAAGTTG GGGGGAGGGG
1001 TCGGCAATTG AACCGGTGCC TAGAGAAGGT GGCGCGGGGT AAACTGGGAA
1051 AGTGATGTCG TGTACTGGCT CCGCCTTTTT CCCGAGGGTG GGGGAGAACC
1101 GTATATAAGT GCAGTAGTCG CCGTGAACGT TCTTTTTCGC AACGGGTTTG
1151 CCGCCAGAAC ACAGGTAAGT GCCGTGTGTG GTTCCCGCGG GCCTGGCCTC
1201 TTTACGGGTT ATGGCCCTTG CGTGCCTTGA ATTACTTCCA CGCCCCTGGC
1251 TGCAGTACGT GATTCTTGAT CCCGAGCTTC GGGTTGGAAG TGGGTGGGAG
1301 AGTTCGAGGC CTTGCGCTTA AGGAGCCCCT TCGCCTCGTG CTTGAGTTGA
1351 GGCCTGGCCT GGGCGCTGGG GCCGCCGCGT GCGAATCTGG TGGCACCTTC
1401 GCGCCTGTCT CGCTGCTTTC GATAAGTCTC TAGCCATTTA AAATTTTTGA
1451 TGACCTGCTG CGACGCTTTT TTTCTGGCAA GATAGTCTTG TAAATGCGGG
1501 CCAAGATCTG CACACTGGTA TTTCGGTTTT TGGGGCCGCG GCGGCGACG
1551 GGGCCCGTGC GTCCCAGCGC ACATGTTCGG CGAGGCGGGG CCTGCGAGCG
1601 CGGCCACCGA GAATCGGACG GGGGTAGTCT CAAGCTGGCC GGCCTGCTCT
1651 GGTGCCTGGC CTCGCGCCGC CGTGTATCGC CCCGCCCTGG GCGGCAAGGC
1701 TGGCCCGGTC GGCACCAGTT GCGTGAGCGG AAAGATGGCC GCTTCCCGGC
1751 CCTGCTGCAG GGAGCTCAAA ATGGAGGACG CGGCGCTCGG GAGAGCGGGC
1801 GGGTGAGTCA CCCACACAAA GGAAAAGGGC CTTTCCGTCC TCAGCCGTCG
1851 CTTCATGTGA CTCCACGGAG TACCGGGCGC CGTCCAGGCA CCTCGATTAG
1901 TTCTCGAGCT TTTGGAGTAC GTCGTCTTTA GGTTGGGGGG AGGGGTTTTA
1951 TGCGATGGAG TTTCCCCACA CTGAGTGGGT GGAGACTGAA GTTAGGCCAG
2001 CTTGGCACTT GATGTAATTC TCCTTGGAAT TTGCCCTTTT TGAGTTTGGA
2051 TCTTGGTTCA TTCTCAAGCC TCAGACAGTG GTTCAAAGTT TTTTTCTTCC
2101 ATTTCAGGTG TCGTGAAaag cTTCTAGAGA TCCCTCGACC TCGAGATCCA
2151 TTGTGCTCTA AAGGAGATAC CCGGCCAGAC ACCCTCACCT GCGGTGCCCA
2201 GCTGCCCAGG CTGAGGCAAG AGAAGGCCAG AAACCATGCC CATGGGGTCT
2251 CTGCAACCGC TGGCCACCTT GTACCTGCTG GGGATGCTGG TCGCTTCCGT
2301 GCTAGCGCAG CTGTGGGACA CCTGGGCAGA TGAAGCCGAG AAAGCCTTGG
2351 GTCCCCTGCT TGCCCGGGAC CGGAGACAGG CCACCGAATA TGAGTACCTA
2401 GATTATGATT TCCTGCCAGA AACGGAGCCT CCAGAAATGC TGAGGAACAG
2451 CACTGACACC ACTCCTCTGA CTGGGCCTGG AACCCCTGAG TCTACCACTG
2501 TGGAGCCTGC TGCAAGGCGT TCTACTGGCC TGGATGCAGG AGGGGCAGTC
2551 ACAGAGCTGA CCACGGAGCT GGCCAACATG GGAACCTGT CCACGGATTC
2601 AGCAGCTATG GAGATACAGA CCACTCAACC AGCAGCCACG GAGGCACAGA
2651 CCACTCCACT GGCAGCCACA GAGGCACAGA CAACTCGACT GACGGCCACG
```

TABLE 7-continued

Human PSGL-1 Expression vector
(SEQ ID NO:21; 5204 nucleotides)

```
2701 GAGGCACAGA CCACTCCACT GGCAGCCACA GAGGCACAGA CCACTCCACC

2751 AGCAGCCACG GAAGCACAGA CCACTCAACC CACAGGCCTG GAGGCACAGA

2801 CCACTGCACC AGCAGCCATG GAGGCACAGA CCACTGCACC AGCAGCCATG

2851 GAAGCACAGA CCACTCCACC AGCAGCCATG GAGGCACAGA CCACTCAAAC

2901 CACAGCCATG GAGGCACAGA CCACTGCACC AGAAGCCACG GAGGCACAGA

2951 CCACTCAACC CACAGCCACG GAGGCACAGA CCACTCCACT GGCAGCCATG

3001 GAGGCCCTGT CCACAGAACC CAGTGCCACA GAGGCCCTGT CCATGGAACC

3051 TACTACCAAA AGAGGTCTGT TCATACCCTT TTCTGTGTCC TCTGTTACTC

3101 ACAAGGGCAT TCCCATGGCA GCCAGCAATT TGTCCGTCAA CTACCCAGTG

3151 GGGGCCCCAG ACCACATCTC TGTGAAGCAG ATCCCGAGC CCAGCGGGCC

3201 CATTTCAACA ATCAACCCCT GTCCTCCATG CAAGGAGTGT CACAAATGCC

3251 CAGCTCCTAA CCTCGAGGGT GGACCATCCG TCTTCATCTT CCCTCCAAAT

3301 ATCAAGGATG TACTCATGAT CTCCCTGACA CCCAAGGTCA CGTGTGTGGT

3351 GGTGGATGTG AGCGAGGATG ACCCAGACGT CCAGATCAGC TGGTTTGTGA

3401 ACAACGTGGA AGTACACACA GCTCAGACAC AAACCCATAG AGAGAATTAC

3451 AACAGTACTG TCCGGGTGGT CAGCACCCTC CCCATCCAGC ACCAGGACTG

3501 GATGAGTGGC AAGGAGTTCA ATGCAAGGT CAACAACAAA GACCTCCCAT

3551 CACCCATCGA GAGAACCATC TCAAAAATTA AAGGGCTAGT CAGAGCTCCA

3601 CAAGTATACA TCTTGCCGCC ACCAGCAGAG CAGTTGTCCA GGAAAGATGT

3651 CAGTCTCACT TGCCTGGTCG TGGGCTTCAA CCCTGGAGAC ATCAGTGTGG

3701 AGTGGACCAG CAATGGGCAT ACAGAGGAGA ACTATAAGGA CACCGCACCA

3751 GTCCTGGACT CTGACGGTTC TTACTTCATA TATAGCAAGC TCAATATGAA

3801 AACAAGCAAG TGGGAGAAAA CAGATTCCTT CTCATGCAAC GTGAGACACG

3851 AGGGTCTGAA AAATTACTAC CTAAAGAAGA CCATCTCCCG GTCTCCGGGT

3901 AAATGAgcgg ccgcCGCAGG TAAGCCAGCC CAGGCCTCGC CCTCCAGCTC

3951 AAGGCGGGAC AGGTGCCCTA GAGTAGCCTG CATCCAGGGA CAGGCCCCAG

4001 CCGGGTGCTG ACACGTCCAC CTCCATCTCT TCCTCAGTTA ACTTGTTTAT

4051 TGCAGCTTAT AATGGTTACA AATAAAGCAA TAGCATCACA AATTTCACAA

4101 ATAAAGCATT TTTTCACTG CATTCTAGTT GTGGTTTGTC CAAACTCATC

4151 AATGTATCTT ATCATGTCTG GATCCGCTAG CGCTTCAGGC ACCGGGCTTG

4201 CGGGTCATGC ACCAGGTCGC GCGGTCCTTC GGGCACTCGA CGTCGGCGGT

4251 GACGGTGAAG CCGAGCCGCT CGTAGAAGGG GAGGTTGCGG GGCGCGGAGG

4301 TCTCCAGGAA GGCGGGCACC CCGGCGCGCT CGGCCGCCTC CACTCCGGGG

4351 AGCACGACGG CGCTGCCCAG ACCCTTGCCC TGGTGGTCGG GCGAGACGCC

4401 GACGGTGGCC AGGAACCACG CGGGCTCCTT GGGCCGGTGC GGCGCCAGGA

4451 GGCCTTCCAT CTGTTGCTGC GCGGCCAGCC GGGAACCGCT CAACTCGGCC

4501 ATGCGCGGGC CGATCTCGGC GAACACCGCC CCCGCTTCGA CGCTCTCCGG

4551 CGTGGTCCAG ACCGCCACCG CGGCGCCGTC GTCCGCGACC CACACCTTGC
```

TABLE 7-continued

Human PSGL-1 Expression vector
(SEQ ID NO:21; 5204 nucleotides)

```
4601  CGATGTCGAG CCCGACGCGC GTGAGGAAGA GTTCTTGCAG CTCGGTGACC
4651  CGCTCGATGT GGCGGTCCGG GTCGACGGTG TGGCGCGTGG CGGGGTAGTC
4701  GGCGAACGCG GCGGCGAGGG TGCGTACGGC CCGGGGGACG TCGTCGCGGG
4751  TGGCGAGGCG CACCGTGGGC TTGTACTCGG TCATGGTGGC CTGCAGAGTC
4801  GCTCGGTGTT CGAGGCCACA CGCGTCACCT TAATATGCGA AGTGGACCTG
4851  GGACCGCGCC GCCCCGACTG CATCTGCGTG TTCGAATTCG CCAATGACAA
4901  GACGCTGGGC GGGGTTTGTG TCATCATAGA ACTAAAGACA TGCAAATATA
4951  TTTCTTCCGG GGACACCGCC AGCAAACGCG AGCAACGGGC CACGGGGATG
5001  AAGCAGCTGC GCCACTCCCT GAAGATCTCC CGCCCCTAAC TCCGCCCATC
5051  CCGCCCCTAA CTCCGCCCAG TTCCGCCCAT TCTCCGCCCC ATGGCTGACT
5101  AATTTTTTTT ATTTATGCAG AGGCCGAGGC CGCGGCCTCT GAGCTATTCC
5151  AGAAGTAGTG AGGAGGCTTT TTTGGAGGCC TAGGCTTTTG CAAAAAGCTA
5201  ATTC
```

TABLE 8

| Nucleic Acid | Corresponding Nucleotide position in SEQ ID NO:21 | SEQ ID NO |
|---|---|---|
| pMB1 origin (pBR322 ori) | 1-593 | 22 |
| (sac2) synthetic tyrosine suppressor tRNA gene(supF gene)remnant of ASV LTR | 594-925 | 23 |
| (spe) EF1alpha prom | 926-2117 | 24 |
| (hind3) human PSGL-1/mouse IgG2b | 2118-3906 | 25 |
| (not) IgG1 hinge/CH2 intron | 3907-4036 | 26 |
| (hpa1) SV40 poly A | 4037-4169 | 27 |
| (bamh1) puromycin acetyltransferase | 4170-4790 | 28 |
| (pst) HSV1 tk promoter −215 to +19, with G to A mutation at +7 | 4791-5022 | 29 |
| (bgl2) SV40 origin (minus enhancer) | 5023-5204 | 30 |

REFERENCES

Auchincloss, H., Jr., and Sachs, D. H. (1998). Xenogeneic transplantation. *Annu Rev Immunol*, 16, 433.

Bhatia, P. K., and Mukhopadhyay, A. (1998). Protein glycosylation: implications for in vivo functions and therapeutic applications. *Adv Biochem Eng Biotechnol*, 64, 155.

Bierhuizen, M. F., and Fukuda, M. (1992). Expression cloning of a cDNA encoding UDP-GlcNAc:Gal beta 1-3-GalNAc-R (GlcNAc to GalNAc) beta 1-6GlcNAc transferase by gene transfer into CHO cells expressing polyoma large tumor antigen. *Proc Natl Acad Sci USA*, 89, 9326.

Bouhours, D., Pourcel, C., and Bouhours, J. E. (1996). Simultaneous expression by porcine aorta endothelial cells of glycosphingolipids bearing the major epitope for human xenoreactive antibodies (Gal alpha 1-3Gal), blood group H determinant and N-glycolylneuraminic acid. *Glycoconj J*, 13, 947.

Boussif, O., Lezoualc'h, F., Zanta, M. A., Mergny, M. D., Scherman, D., Demeneix, B., and Behr, J. P. (1995). A versatile vector for gene and oligonucleotide transfer into cells in culture and in vivo: polyethylenimine. *Proc Natl AcadSci USA*, 92, 7297.

Cairns, T., Lee, J., Goldberg, L. C., Hakim, N., Cook, T., Rydberg, L., Samuelsson, B., and Taube, D. (1996). Thomsen-Friedenreich and PK antigens in pig-to-human xenotransplantation. *Transplant Proc*, 28, 795.

Cairns, T. D., Taube, D. H., Stevens, N., Binns, R., and Welsh, K. I. (1991). Xenografts—future prospects for clinical transplantation. *Immunol Lett*, 29, 167.

Carlstedt, I., Herrmann, A., Karlsson, H., Sheehan, J., Fransson, L. A., and Hansson, G. C. (1993). Characterization of two different glycosylated domains from the insoluble mucin complex of rat small intestine. *J Biol Chem*, 268, 18771.

Ciucanu, I., and Kerek, F. (1984). A simple and rapid method for the permethylation of carbohydrates. *Carbohydr Res*, 131, 209.

Corzana, F., Bettler, E., Herve du Penhoat, C., Tyrtysh, T. V., Bovin, N. V., and Imberty, A. (2002). Solution structure of two xenoantigens: alpha Gal-LacNAc and alpha Gal-Lewis X. *Glycobiology*, 12, 241.

Dennis, J. W. (1993). Core 2 GlcNAc-transferase and poly-lactosamine expression in O-glycans. *Glycobiology*, 3, 91.

Galili, U. (1993). Interaction of the natural anti-Gal antibody with alpha-galactosyl epitopes: a major obstacle for xenotransplantation in humans. *Immunol Today*, 14, 480.

Galili, U., Macher, B. A., Buehler, J., and Shohet, S. B. (1985). Human natural anti-alpha-galactosyl IgG. II. The specific recognition of alpha (1——3)-linked galactose residues. *J Exp Med*, 162, 573.

Gervais, A., Hammel, Y. A., Pelloux, S., Lepage, P., Baer, G., Carte, N., Sorokine, O., Strub, J. M., Koerner, R., Leize, E., and Van Dorsselaer, A. (2003). Glycosylation of human recombinant gonadotrophins: characterization and batch-to-batch consistency. *Glycobiology*, 13, 179.

Gustafsson, K., Strahan, K., and Preece, A. (1994). Alpha 1,3galactosyltransferase: a target for in vivo genetic manipulation in xenotransplantation. *Immunol Rev,* 141, 59.

Hansson, G. C., and Karlsson, H. (1993). Gas chromatography and gas chromatography-mass spectrometry of glycoprotein oligosaccharides. *Methods Mol Biol,* 14, 47.

He, Z., She, R., Sumitran-Holgersson, S., Blomberg, P., Islam, K. B., and Holgersson, J. (2001). The in vitro activity and specificity of human endothelial cell-specific promoters in porcine cells. *Xenotransplantation,* 8, 202.

Hokke, C. H., Bergwerff, A. A., Van Dedem, G. W., Kamerling, J. P., and Vliegenthart, J. F. (1995). Structural analysis of the sialylated N- and O-linked carbohydrate chains of recombinant human erythropoietin expressed in Chinese hamster ovary cells. Sialylation patterns and branch location of dimeric N-acetyllactosamine units. *Eur J Biochem,* 228, 981.

Imberty, A., Mikros, E., Koca, J., Mollicone, R., Oriol, R., and Perez, S. (1995). Computer simulation of histo-blood group oligosaccharides: energy maps of all constituting disaccharides and potential energy surfaces of 14 ABH and Lewis carbohydrate antigens. *Glycoconj J,* 12, 331.

Imberty, A., Mollicone, R., Mikros, E., Carrupt, P. A., Perez, S., and Oriol, R. (1996). How do antibodies and lectins recognize histo-blood group antigens? A 3D-QSAR study by comparative molecular field analysis (CoMFA). *Bioorg Med Chem,* 4, 1979.

Imberty, A., Perez, S., Hricovini, M., Shah, R. N., and Carver, J. P. (1993). Flexibility in a tetrasaccharide fragment from the high mannose type of N-linked oligosaccharides. *Int J Biol Macromol,* 15, 17.

Itoh, S., Kawasaki, N., Ohta, M., and Hayakawa, T. (2002). Structural analysis of a glycoprotein by liquid chromatography-mass spectrometry and liquid chromatography with tandem mass spectrometry. Application to recombinant human thrombomodulin. *J Chromatogr A,* 978, 141.

Joziasse, D. H., Shaper, J. H., Jabs, E. W., and Shaper, N. L. (1991). Characterization of an alpha 1——3-galactosyltransferase homologue on human chromosome 12 that is organized as a processed pseudogene. *J Biol Chem,* 266, 6991.

Khodadoust, M. M., Candal, F. J., and Maher, S. E. (1995). PEC-A: an immortalized porcine aortic endothelial cell. *Xenotransplantation,* 2, 79.

Kitov, P. I., Sadowska, J. M., Mulvey, G., Armstrong, G. D., Ling, H., Pannu, N. S., Read, R. J., and Bundle, D. R. (2000). Shiga-like toxins are neutralized by tailored multivalent carbohydrate ligands. *Nature,* 403, 669.

Kumar, R., Camphausen, R. T., Sullivan, F. X., and Cumming, D. A. (1996). Core2 beta-1,6-N-acetylglucosaminyltransferase enzyme activity is critical for P-selectin glycoprotein ligand-1 binding to P-selectin. *Blood,* 88, 3872.

Laemmli, U. K. (1970). Cleavage of structural proteins during the assembly of the head of bacteriophage T4. *Nature,* 227, 680.

Lee, R. T., and Lee, Y. C. (2000). Affinity enhancement by multivalent lectin-carbohydrate interaction. *Glycoconj J,* 17, 543.

Lindhorst, T. K., Kieburg, C., and Krallmann-Wenzel, U. (1998). Inhibition of the type 1 fimbriae-mediated adhesion of *Escherichia coli* to erythrocytes by multiantennary alpha-mannosyl clusters: the effect of multivalency. *Glycoconj J,* 15, 605.

Liu, J., Qian, Y., and Holgersson, J. (1997). Removal of xenoreactive human anti-pig antibodies by absorption on recombinant mucin-containing glycoproteins carrying the Gal alpha1,3Gal epitope. *Transplantation,* 63, 1673.

Liu, J., Weintraub, A., and Holgersson, J. (2003). Multivalent Galalpha1,3Gal-substitution makes recombinant mucin-immunoglobulins efficient absorbers of anti-pig antibodies. *Xenotransplantation,* 10, 149.

Lofling, J. C., Hauzenberger, E., and Holgersson, J. (2002). Absorption of anti-blood group A antibodies on P-selectin glycoprotein ligand-1/immunoglobulin chimeras carrying blood group A determinants: core saccharide chain specificity of the Se and H gene encoded alpha1,2 fucosyltransferases in different host cells. *Glycobiology,* 12, 173.

Maaheimo, H., Renkonen, R., Turunen, J. P., Penttila, L., and Renkonen, O. (1995). Synthesis of a divalent sialyl Lewis x O-glycan, a potent inhibitor of lymphocyte-endothelium adhesion. Evidence that multivalency enhances the saccharide binding to L-selectin. *Eur J Biochem,* 234, 616.

Malykh, Y. N., King, T. P., Logan, E., Kelly, D., Schauer, R., and Shaw, L. (2003). Regulation of N-glycolylneuraminic acid biosynthesis in developing pig small intestine. *Biochem J,* 370, 601.

Malykh, Y. N., Krisch, B., Shaw, L., Warner, T. G., Sinicropi, D., Smith, R., Chang, J., and Schauer, R. (2001). Distribution and localization of CMP-N-acetylneuraminic acid hydroxylase and N-glycolylneuraminic acid-containing glycoconjugates in porcine lymph node and peripheral blood lymphocytes. *Eur J Cell Biol,* 80, 48.

Mammen, M., Choi, S., and Whitesides, G. (1998). Polyvalent interactions in biological systems:implications for design and use of multivalent ligands and inhibitors. *Angew Chem Int Ed,* 37, 2754.

McEver, R. P., Moore, K. L., and Cummings, R. D. (1995). Leukocyte trafficking mediated by selectin-carbohydrate interactions. *J Biol Chem,* 270, 11025.

Mitoma, J., Petryniak, B., Hiraoka, N., Yeh, J. C., Lowe, J. B., and Fukuda, M. (2003). Extended core 1 and core 2 branched O-glycans differentially modulate sialyl Lewis X-type L-selectin ligand activity. *J Biol Chem,* 278, 9953.

Miyata, Y., and Platt, J. L. (2003). Xeno-still stuck without alphaGal. *Nat Biotechnol,* 21, 359.

Moore, K. L., Eaton, S. F., Lyons, D. E., Lichenstein, H. S., Cummings, R. D., and McEver, R. P. (1994). The P-selectin glycoprotein ligand from human neutrophils displays sialylated, fucosylated, O-linked poly-N-acetyllactosamine. *J Biol Chem,* 269, 23318.

Neethling, F. A., Koren, E., Ye, Y., Richards, S. V., Kujundzic, M., Oriol, R., and Cooper, D. K. (1994). Protection of pig kidney (PK15) cells from the cytotoxic effect of anti-pig antibodies by alpha-galactosyl oligosaccharides. *Transplantation,* 57, 959.

Oriol, R., Ye, Y., Koren, E., and Cooper, D. K. (1993). Carbohydrate antigens of pig tissues reacting with human natural antibodies as potential targets for hyperacute vascular rejection in pig-to-man organ xenotransplantation. *Transplantation,* 56, 1433.

Pascher, A., Poehlein, C., Stangl, M., Thiery, J., Mueller-Derlich, J., and Hammer, C. (1997). Immunoapheresis, an advanced technique for depleting human anti-porcine antibodies, delays hyperacute rejection of xenogeneic perfused pig livers. *Transplant Proc,* 29, 962.

Phelps, C. J., Koike, C., Vaught, T. D., Boone, J., Wells, K. D., Chen, S. H., Ball, S., Specht, S. M., Polejaeva, I. A., Monahan, J. A., Jobst, P. M., Sharma, S. B., Lamborn, A. E., Garst, A. S., Moore, M., Demetris, A. J., Rudert, W. A., Bottino, R., Bertera, S., Trucco, M., Starzl, T. E., Dai, Y., and Ayares, D. L. (2003). Production of alpha 1,3-galactosyltransferase-deficient pigs. *Science,* 299, 411.

Renkonen, O., Toppila, S., Penttila, L., Salminen, H., Helin, J., Maaheimo, H., Costello, C. E., Turunen, J. P., and Renkonen, R. (1997). Synthesis of a new nanomolar saccharide inhibitor of lymphocyte adhesion: different polylactosamine backbones present multiple sialyl Lewis x determinants to L-selectin in high-affinity mode. *Glycobiology*, 7, 453.

Rydberg, L., Holgersson, J., Samuelsson, B. E., and Breimer, M. E. (1999). alpha-Gal epitopes in animal tissue glycoproteins and glycolipids. *Subcell Biochem*, 32, 107.

Sako, D., Chang, X. J., Barone, K. M., Vachino, G., White, H. M., Shaw, G., Veldman, G. M., Bean, K. M., Ahern, T. J., Furie, B., and et al. (1993). Expression cloning of a functional glycoprotein ligand for P-selectin. *Cell*, 75, 1179.

Sako, D., Comess, K. M., Barone, K. M., Camphausen, R. T., Cumming, D. A., and Shaw, G. D. (1995). A sulfated peptide segment at the amino terminus of PSGL-1 is critical for P-selectin binding. *Cell*, 83, 323.

Schachter, H. (2000). The joys of HexNAc. The synthesis and function of N- and O-glycan branches. *Glycoconj J*, 17, 465. Sharma, A., Naziruddin, B., Cui, C., Martin, M. J., Xu, H., Wan, H., Lei, Y., Harrison, C., Yin, J., Okabe, J., Mathews, C., Stark, A., Adams, C. S., Houtz, J., Wiseman, B. S., Byrne, G. W., and Logan, J. S. (2003). Pig cells that lack the gene for alpha1-3 galactosyltransferase express low levels of the gal antigen. *Transplantation*, 75, 430.

Sheeley, D. M., Merrill, B. M., and Taylor, L. C. (1997). Characterization of monoclonal antibody glycosylation: comparison of expression systems and identification of terminal alpha-1 inked galactose. *Anal Biochem*, 247, 102.

Silverman, H. S., Sutton-Smith, M., McDermott, K., Heal, P., Leir, S. H., Morris, H. R., Hollingsworth, M. A., Dell, A., and Harris, A. (2003). The contribution of tandem repeat number to the O-glycosylation of mucins. *Glycobiology*, 13, 265.

Skrincosky, D., Kain, R., El-Battari, A., Exner, M., Kerjaschki, D., and Fukuda, M. (1997). Altered Golgi localization of core 2 beta-1,6-N-acetylglucosaminyltransferase leads to decreased synthesis of branched O-glycans. *J Biol Chem*, 272, 22695.

Ten Hagen, K. G., Fritz, T. A., and Tabak, L. A. (2003). All in the family: the UDP-GalNAc:polypeptide N-acetylgalactosaminyltransferases. *Glycobiology*, 13, 1.

Totani, K., Kubota, T., Kuroda, T., Murata, T., Hidari, K. I., Suzuki, T., Suzuki, Y., Kobayashi, K., Ashida, H., Yamamoto, K., and Usui, T. (2003). Chemoenzymatic synthesis and application of glycopolymers containing multivalent sialyloligosaccharides with a poly(L-glutamic acid) backbone for inhibition of infection by influenza viruses. *Glycobiology*, 13, 315.

Towbin, H., Staehelin, T., and Gordon, J. (1979). Electrophoretic transfer of proteins from polyacrylamide gels to nitrocellulose sheets: procedure and some applications. *Proc Natl Acad Sci USA*, 76, 4350.

Van den Nieuwenhof, I. M., Koistinen, H., Easton, R. L., Koistinen, R., Kamarainen, M., Morris, H. R., Van Die, I., Seppala, M., Dell, A., and Van den Eijnden, D. H. (2000). Recombinant glycodelin carrying the same type of glycan structures as contraceptive glycodelin-A can be produced in human kidney 293 cells but not in chinese hamster ovary cells. *Eur J Biochem*, 267, 4753.

Varki, A. (2001). N-glycolylneuraminic acid deficiency in humans. *Biochimie*, 83, 615.

Yan, S. B., Chao, Y. B., and van Halbeek, H. (1993). Novel Asn-linked oligosaccharides terminating in GalNAc beta (1->4)[Fuc alpha (1->3)]GlcNAc beta (1->.) are present in recombinant human protein C expressed in human kidney 293 cells. *Glycobiology*, 3, 597.

Yeh, J. C., Ong, E., and Fukuda, M. (1999). Molecular cloning and expression of a novel beta-1, 6-N-acetylglucosaminyltransferase that forms core 2, core 4, and I branches. *J Biol Chem*, 274, 3215.

Zhu, A., and Hurst, R. (2002). Anti-N-glycolylneuraminic acid antibodies identified in healthy human serum. *Xenotransplantation*, 9, 376.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of producing a mucin-immunoglobulin fusion polypeptide comprising:
    a) providing a cell comprising:
        i) a nucleic acid encoding a mucin polypeptide linked to a nucleic acid encoding at least a region of an immunoglobulin polypeptide;
        ii) a nucleic acid encoding an α1,3 galactosyltransferase polypeptide; and
        iii) a nucleic acid encoding a β 1,6,-N-acetylglucosaminyltransferase polypeptide;
    b) culturing the cell under conditions that permit production of said mucin-immunoglobulin fusion polypeptide wherein said fusion polypeptide is glycosylated by said α1,3 galactosyltransferase and said β 1,6,-N-acetylglucosaminyltransferase; and
    c) isolating said mucin-immunoglobulin fusion polypeptide.

2. The method of claim 1, wherein the mucin polypeptide is selected from the group consisting of PSGL-1, MUC1, MUC2, MUC3, MUC4, MUC5a, MUC5b, MUC5c, MUC6, MUC11, MUC12, CD34, CD43, CD45, CD96, GlyCAM-1, and MAdCAM 3 or fragment thereof.

3. The method of claim 1, wherein the mucin polypeptide comprises at least a region of a P-selectin glycoprotein ligand-1.

4. The method of claim 1, wherein said mucin polypeptide comprises an extracellular region of a P-selectin glycoprotein ligand-1.

5. The method of claim 1, wherein the immunoglobulin polypeptide comprises a region of a heavy chain immunoglobulin polypeptide.

6. The method of claim 1, wherein the immunoglobulin polypeptide comprises an Fc region of an immunoglobulin heavy chain.

7. The method of claim 1, wherein the cell is a eukaryotic cell, or a prokaryotic cell.

8. The method of claim 7, wherein the eukaryotic cell is a mammalian cell, an insect cell or a yeast cell.

9. The method of claim 7, wherein the prokaryotic cell is a bacterial cell.

10. The method of claim 7, wherein the eukaryotic cell is a CHO cell, a COS cell or a 293 cell.

11. A method of producing a mucin-immunoglobulin fusion polypeptide comprising:
    a) introducing into a cell
        i) a nucleic acid encoding a mucin polypeptide linked to a nucleic acid encoding at least a region of an immunoglobulin polypeptide, ii) a nucleic acid encoding an α1,3 galactosyltransferase polypeptide; and
iii) a nucleic acid encoding a β 1,6,-N-acetylglucosaminyltransferase polypeptide;
b) culturing the cell under conditions that permit production of said mucin-immunoglobulin fusion polypeptide wherein said fusion polypeptide is glycosylated by said α1,3 galactosyltransferase polypeptide and said β 1,6,-N-acetylglucosaminyltransferase; and
c) isolating said mucin-immunoglobulin fusion polypeptide.

12. A cell comprising:
a) a nucleic acid encoding a mucin polypeptide linked to a nucleic acid encoding at least a region of an immunoglobulin polypeptide,
b) a nucleic acid encoding an α1,3 galactosyltransferase polypeptide;
c) and a nucleic acid encoding a β 1,6,-N-acetylglucosaminyltransferase.

13. The cell of claim 12, wherein the cell is a CHO cell.

* * * * *

UNITED STATES PATENT AND TRADEMARK OFFICE
CERTIFICATE OF CORRECTION

PATENT NO.      : 7,638,323 B2                    Page 1 of 1
APPLICATION NO. : 10/638820
DATED           : December 29, 2009
INVENTOR(S)     : Holgersson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1484 days.

Signed and Sealed this

Twenty-first Day of December, 2010

David J. Kappos
*Director of the United States Patent and Trademark Office*